US012391719B2

(12) United States Patent
Pemberton et al.

(10) Patent No.: US 12,391,719 B2
(45) Date of Patent: *Aug. 19, 2025

(54) METHODS FOR PRODUCING STEREOISOMERICALLY ENRICHED CARBOHYDRATE-BASED SURFACTANTS

(71) Applicant: ARIZONA BOARD OF REGENTS ON BEHALF OF THE UNIVERSITY OF ARIZONA, Tucson, AZ (US)

(72) Inventors: Jeanne E. Pemberton, Tucson, AZ (US); Tyler Roberts, Tucson, AZ (US)

(73) Assignee: ARIZONA BOARD OF REGENTS ON BEHALF OF THE UNIVERSITY OF ARIZONA, Tucson, AZ (US)

( * ) Notice: Subject to any disclaimer, the term of this patent is extended or adjusted under 35 U.S.C. 154(b) by 995 days.

This patent is subject to a terminal disclaimer.

(21) Appl. No.: 17/489,477

(22) Filed: Sep. 29, 2021

(65) Prior Publication Data

US 2022/0017556 A1    Jan. 20, 2022

Related U.S. Application Data

(63) Continuation-in-part of application No. 17/473,999, filed on Sep. 13, 2021, now abandoned, which is a continuation of application No. 15/358,159, filed on Nov. 22, 2016, now Pat. No. 11,117,914, which is a continuation-in-part of application No. 14/041,251, filed on Sep. 30, 2013, now Pat. No. 9,499,575.

(60) Provisional application No. 61/796,653, filed on Nov. 16, 2012.

(51) Int. Cl.
C07H 15/04   (2006.01)
C07F 3/00    (2006.01)
C07F 9/94    (2006.01)
C07H 1/00    (2006.01)
C07H 15/06   (2006.01)
C07H 15/14   (2006.01)

(52) U.S. Cl.
CPC .......... C07H 15/14 (2013.01); C07F 3/003 (2013.01); C07F 9/94 (2013.01); C07H 1/00 (2013.01); C07H 15/04 (2013.01); C07H 15/06 (2013.01)

(58) Field of Classification Search
None
See application file for complete search history.

(56) References Cited

U.S. PATENT DOCUMENTS 5,166,337 A    11/1992  Ripke
9,499,575 B2   11/2016  Pemberton et al.
11,117,914 B2 *  9/2021  Pemberton ............... C07H 1/00
2004/0173696 A1  9/2004  Cunningham et al.

OTHER PUBLICATIONS

Ahad et al., Synthesis and Biological Activities of Flavolipids, Tetrahedron, 2010, 9107-9112, vol. 66.
Al-Tahhan, R.A.; Sandrin, T.R.; Bodour, A.A.; Maier, R.M., Rhamnolipid-Induced Removal of Lipopolysaccharide from Pseudomonas aeruginosa: Effect of Cell Surface Properties and Interaction with Hydrophobic Substrates, Applied and Environmental Microbiology, 2000, 3262-3268, vol. 66.
AN1988:201407—Matsuyama et al., Iyo Masu Kenkyukai Koenshu, 1987, vol. 12, pp. 71-76. (Year: 1987).
Bauer, J.; Brandenburg, K.; Zahringer, U.; Rademann, J., Chemical Synthesis of a Glycolipid Library by a Solid-Phase Strategy Allows Elucidation of the Structural Specificity of Immunistimulation by Rhamnolipids, Chemistry, a European Journal, 2006, 7116-7124, vol. 12.
Coss et al., Minimally Competent Lewis Acid Catalysts: Indium(III) and Bismuth(III) Salts Produce Rhamnosides (=6-Deoxymannosides) in High Yield and Purity, Helvetica Chimica Acta, 2012, 2652-2659, vol. 95.
Coss, C.S., Minimally Competent Lewis Acid Catalysts. General Methods for the Synthesis and Separation of Diastereomeric Mixtures of Monorhamnolipids of Pseudomonas aeruginosa with Peracetate Glycoside Donors, Ph.D. dissertation, 2012, 1-274, University of Arizona.
Dalhoff, W.V., Synthesis of a Series of Alkyl 1-Thio-D-Glucopyranosides and Their Regioselective Reductions to 1-Alkylthio-1-Deoxy-D-Glucitols, Liebigs Ann. Chem., 1990, 1025-1027.
Ikeda, K.; Torisawa, Y.; Nishi, T.; Minamikawa, J.; Tanaka, K.; Sato, M., Glycosylation of Sialyl Acetates with a Novel Catalyst Combination: Bismuth Triflate and BF3.OET2 System, Bioorganic & Medicinal Chemistry, 2003, 3073-3076, vol. 11.
International Search Report and Written Opinion on PCT/EP2016/058998 dated Jul. 8, 2016 (14 pages).
J. Lokesh Babu; Anakshi Khare; and Yashwant D. Vankar, "Bi(OTf)3 and Sio2-Bi(OTf)3 as Effective catalysts for the Ferrier Rearrangement#", 2005, Molecules, pp. 884-892.
Joo et al., "Cyclic Peptides as Therapeutic Agents and Biochemical Tools," Biomolecular and Therapeutics, vol. 20, No. 1, Oct. 28, 2011, pp. 19-26.
Kitamoto, D.; Hisoda, H.; Nakahara, T.J., Functions and Potential Applications of Glycolipid Biosurfactants, from Energy Saving-Materials to Gene Delivery Carriers, Journal of Bioscience and Bioengineering, 2002, 187-201, vol. 94.
Lebron-Paler, A., Solution and Interfacial Characterization of Rhamnolipid Biosurfactant from P. aeruginosa ATCC 9027, Ph.D. dissertation, 2008, 1-481, University of Arizona.
Lebron-Paler, A.; Pemberton, J.E.; Otto, W.C.; Becker, B.K.; Larive, C.K.; Maier, R.M., Determination of the Acid Dissociation Constant of the Biosurfactants Monorhamnolipid in Aqueous Solution by Potentiometric and Spectroscopic Methods, Anal. Chem., 2006, 7649-7658, vol. 78.
Lefever, M.R.; Szabo, L.; Anglin, B.; Ferracane, M.; Hogan, J.; Cooney, L.; Polt, R., Glycosylation of a-Amino Acids by Sugar Acetate Donors with InBr3. Minimally Competent Lewis Acids, Carbohydrate Research, 2012, 121-125, vol. 351.

(Continued)

Primary Examiner — Traviss C McIntosh, III
(74) Attorney, Agent, or Firm — Foley & Lardner LLP

(57) ABSTRACT

The present disclosure discusses methods for producing stereoisomerically enriched carbohydrate-based surfactants. In particular, methods of the invention include producing stereoisomerically enriched hydrophobic portion of the carbohydrate-based surfactants.

9 Claims, 6 Drawing Sheets

(56) References Cited

OTHER PUBLICATIONS

Leonard, N.M.; Weiland, L.C.; Mohan, R.S., Applications of Bismuth (III) Compounds in Organic Synthesis, Tetrahedron, 2002, 8373-8397, vol. 58.

Lindhorst, T.K.; Essential of Carbohydrate Chemistry and Biochemistry, 6 Structure and Biosynthesis of Glycoconjugates, 2007, 224-225, 2nd Ed., New York.

Nakajima, H.; Miura, Y.; Yamagata, T.J., Glycosylation of Amphipathic Lactoside Primers with Consequent Inhibition of Endogenous Glycosphingolipid Synthesis, J. Biochem., 1998, 148-156, vol. 124.

Neilson, J.W.; Zhang, L.; Veres-Schalnat, T.A.; Chandler, K.B.; Neilson, C.H.; Crispin, J.D.; Pemberton, J.E.; Maier, R.M., Cadmium Effects on Transcriptional Expression of rhIB/rhIC Genes and Congener Distribution of Monorhamnolipid and Dirhamnolipid in Pseudomonas aeruginosa IGB83, Appl. Microbial. Biotechnol., 2010, 953-963, vol. 88.

Sani, H.S.; Barragan-Huerta, B.E.; Lebron-Paler, A.; Pemberton, J.E.; Vasquez, R.R.; Burns, A.M.; Marron, M.T.; Seliga, C.J.; Gunatilaka, A.A.L.; Maier, R.M., Efficient Purification of the Biosurfactant Viscosin from Pseudomonas Libanensis Strain M9-3, and Its Physicochemical and Biological Properties, J. Nat. Prod., 2008, 1011-1015, vol. 71.

Schmidt, R.R., New Methods for the Synthesis of Glycosides and Oligosaccharides—Are There Alternatives to the Koenigs-Knorr Method?, Angew. Chem. Int. Ed. Engl., 1986, 212-235, vol. 25.

Shimoda et al., Molecules, 2011, vol. 16, pp. 6769-6777. (Year: 2011).

Takashi Yamanoi; Ryo Inoue; Sho Matsuda; and Keita Hamasaki, "Bismuth(III) Triflated-Catalyzed Dehydrative Glycosidation Using 1-Hydroxy Sugars", 2008, Letters in Organic Chemistry, vol. 5, pp. 30-33.

Tanaka et al., "Exploring Enzymatic Catalysis at a Solid Surface: A Case Study with Transglutaminase-Mediated Protein Immobilization", 2007, Organic and Biomolecular Chemistry, vol. 5, No. 11, pp. 1764-1770.

Wakao. M.; Suda. Y., Synthesis of Glycolipids, Glycoscience, 2008, 1629-1669, Kagoshima, Japan.

Wang, H.; Coss, C.S.; Mudalige, A.; Polt, R.L.; Pemberton, J.E., a PM-IRRAS Investigation of Monorhamnolipid Orientation at the Air-Water Interface, Langmuir, 2013, 4441-4450, vol. 29.

Wang, H.; Solution and Interfacial Characterization of Rhamnolipid Biosurfactants and their Synthetic Analogues, Ph.D. dissertation, 1-368, University of Arizona.

Watanabe, Y.; Nakamosto, C.; Ozaki, S., Glycosylation Based on Phosphite Chemistry, Synlett, 1993, 115-116.

Witczak, Z.J., Current Medicinal Chemistry, Thio Sugars: Biological Relevance as Potential New Therapeutics, 1999, 165-178, vol. 6.

Zang et al., "Tight-binding Streptavidin Ligands from a Cyclic Peptide Library", Sep. 8, 1998, Biorganic and Medicinal Chemistry Letters, vol. 8, No. 17, pp. 2327-2332.

Zhang, L.; Veres-Schalnat, T.A.; Somogyi, A.; Pemberton, J.E.; Maier, R.M., Fatty Acid Cosubstrate Il-Oxidation Provides Precursors for Rhamnolipid Biosynthesis in Pseudomonas aeruginosa: Evidence from Isotope Tracing and Gene Expression, Applied and Environmental Microbiology, 2012, 8611-8622, vol. 78.

\* cited by examiner

METHODS FOR PRODUCING STEREOISOMERICALLY ENRICHED CARBOHYDRATE-BASED SURFACTANTS

CROSS-REFERENCE TO RELATED APPLICATIONS

This application is a continuation-in-part of U.S. patent application Ser. No. 17/473,999, filed Sep. 13, 2021, which is continuation of U.S. patent application Ser. No. 15/358, 159, filed Nov. 22, 2016, which is a continuation-in-part application of U.S. patent application Ser. No. 14/041,251, filed Sep. 30, 2013, now U.S. Pat. No. 9,499,575, issued Nov. 22, 2016, which claims the priority benefit of U.S. Provisional Application No. 61/796,653, filed Nov. 16, 2012, all of which are incorporated herein by reference in their entirety.

STATEMENT REGARDING FEDERALLY FUNDED RESEARCH

This invention was made with government support under grant numbers CHE-1339597 and CHE-1954467 awarded by the National Science Foundation. The government has certain rights in the invention.

FIELD OF THE INVENTION

The present disclosure relates to methods for producing stereoisomerically enriched carbohydrate-based surfactants. In particular, methods of the invention include producing stereoisomerically enriched hydrophobic portion of the carbohydrate-based surfactants.

BACKGROUND OF THE INVENTION

In the chemical synthesis of carbohydrate-based biosurfactants, the lack of diastereomer control is currently one of the last major limitations. While a few synthetic approaches have been used for some "single-tailed" rhamnolipid biosurfactants, these methodologies lack general applicability and more importantly the ability to synthesize optically pure rhamnolipids.

One of the first steps in the synthesis of carbohydrate-based biosurfactants is production of an ester protected 3-hydroxyalkanoate "tail," which has previously been reported using a two-step Meldrum's acid synthesis followed by reduction. A racemic mixture of 3-hydroxyalkanoate can also be prepared using a Reformatsky condensation of an aldehyde and a bromoacetate in the presence of zinc metal catalyst in a single step. Unfortunately, both of these methods afford the tail only a racemic mixture, and ultimately, accounts for the lack of diastereomeric control.

In the synthesis of single-tail carbohydrate-based surfactants, such as a rhamnolipid (e.g., Rha-C10), two diastereomers are possible whereas in the case of two-tail carbohydrate-based surfactants, four diastereomers are possible. The racemic mixture of tails necessitates the synthesis and separation of all rhamnolipid diastereomers and the lack of diastereomeric control is not only problematic from a purity standpoint, but the separation of the diastereomers is solvent intensive and can therefore be considered to dramatically hamper the industrial applicability and environmentally friendliness (e.g., greenness) of the synthesis.

In addition, it has been shown that various carbohydrate-based surfactant diastereomers of single and two-tails feature distinct surfactant properties. Specifically, the critical micelle concentration and minimum surface tension in water is significantly different between the various carbohydrate-based surfactant diastereomers. Furthermore, it is known that native rhamnolipid products produced by *P. aeruginosa* are diastereomerically pure; the tail's carbinol position exclusively possesses the CIP (R)-configuration.

To access stereoselective carbohydrate-based surfactants, e.g., native rhamnolipids and their related structures, without the tedium and cost of microbial batch production, or other carbohydrate-based surfactant diastereomers as demanded by the application or research, an asymmetric synthetic methodology that maintains green indices is needed.

SUMMARY OF THE INVENTION

Some aspects of the invention provide methods for producing stereoisomerically enriched carbohydrate-based surfactants. In some embodiments, methods of the invention produce a carbohydrate-based surfactant of the formula: A-B, where A is a carbohydrate or a protected carbohydrate moiety and B is a hydrophobic moiety. In some embodiments, the hydrophobic moiety is a 3-hydroxy carboxylic acid or 3-hydroxy carboxylate ester moiety. Still in other embodiments, the hydrophobic moiety can include one or two hydrophobic moieties. Linkage between A and B can be either α- or β-anomeric linkage.

One particular aspect of the invention provides a stereoselective method for producing a protected carbohydrate-based surfactant of the formula:

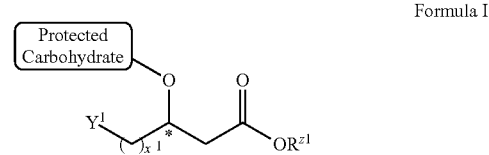

Formula I said method comprising: contacting an enantiomerically enriched alcohol compound of the formula:

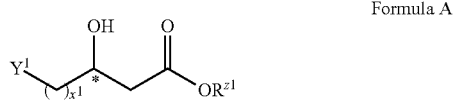

Formula A with a protected carbohydrate under conditions sufficient to form a covalent bond between said carbohydrate and said compound of Formula A to produce said protected carbohydrate-based surfactant of Formula I, wherein a carbohydrate of said protected carbohydrate is selected from the group consisting of a monosaccharide, a disaccharide, a trisaccharide and a derivative thereof, $Y^1$ is selected from the group consisting of hydrogen, ethylenyl, ethynyl, halide, —SH, —$NH_2$, and —$CO_2R^s$;

$R^{z1}$ is hydrogen, alkyl, benzyl, or a carboxylic acid protecting group;

$R^s$ is hydrogen or alkyl;

$x^1$ is an integer from 5 to 30; and

* is a chiral center.

As stated in above, it should be appreciated that the protected carbohydrate and the carboxylate moiety can be linked via an α- or β-anomeric linkage.

In some embodiments, the enantiomerically enriched alcohol compound of Formula A is produced by an enzymatic kinetic resolution, wherein said enzymatic kinetic resolution comprises contacting a compound of the formula:

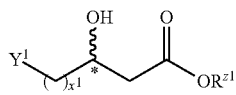

Formula A-1 with an esterase in the presence of an ester compound of the formula $R^aO$—$C(=O)$—$R^x$ under conditions sufficient to produce a mixture of an enantiomerically enriched alcohol compound of the formula:

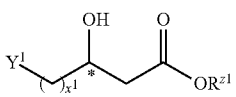

Formula A-2$^a$ and an enantiomerically enriched ester compound of the formula:

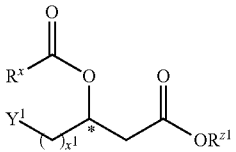

Formula A-2$^b$ wherein
  $R^a$ is methyl,
  $R^x$ is alkyl, typically methyl or ethyl, and
  $x^1$, $Y^1$, and $R^{z1}$ are those defined herein,
and wherein
  when compound of Formula A-2$^a$ has a same stereochemistry as compound of Formula A then separating said compound of Formula A-2$^a$ from said mixture to obtain said enantiomerically enriched alcohol compound of Formula A; and
  when said compound of Formula A-2$^b$ has a same stereochemistry as compound of Formula A, then:
    (i) separating compound of Formula A-2$^b$ from said mixture;
    (ii) producing said enantiomerically enriched alcohol compound of Formula A by hydrolyzing an ester group of said compound of Formula A-2$^b$.

Still in other embodiments, enzymatic kinetic resolution produces at least about 85% ee, typically at least about 90% ee, often at least about 95% ee, and most often at least about 98% ee of compound of Formula A.

Yet in other embodiments, the esterase comprises any triacylglycerol lipase (i.e., triglyceride lipase) or triacylglycerol acyl hydrolase-EC 3.1.1.3 (lipase) in the Enzyme Commission database. See, enzyme.expasy.org/cgi-bin/enzyme/enzyme-search-ec.

In further embodiment, the esterase is immobilized on a solid support.

In other embodiments, methods of the invention further include the steps of deprotecting said protected carbohydrate to produce a surfactant carbohydrate of the formula:

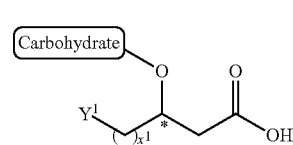

Formula I-A wherein $Y^1$, $x^1$, and * are those defined herein.

Still in further embodiments, methods of the invention further include the following steps of:
  (i) when $R^{z1}$ of said compound of Formula I is alkyl, benzyl, or a carboxylic acid protecting group, then hydrolyzing $R^{z1}$ of said compound of Formula I under conditions sufficient to produce an enantiomerically enriched carboxylic acid compound of the formula:

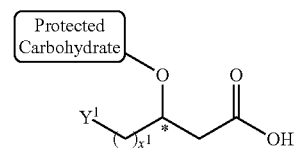

Formula I-B (ii) reacting said enantiomerically enriched carboxylic acid of Formula I-B with a lipid of the formula:

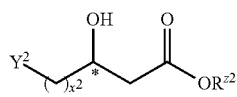

Formula B under conditions sufficient to produce a di-lipid carbohydrate of the formula:

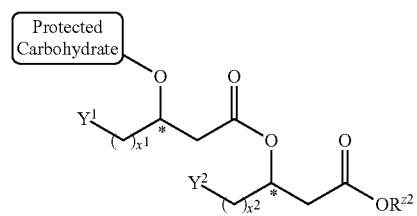

Formula II wherein
  $Y^1$, $x^1$, and * are those defined herein;
  $Y^2$ is selected from the group consisting of hydrogen, ethylenyl, ethynyl, halide, —SH, —NH$_2$, and —CO$_2$R$^{s2}$;
  $R^{z2}$ is hydrogen, alkyl, benzyl, or a carboxylic acid protecting group, typically, hydrogen or methyl;
  $R^{s2}$ is hydrogen or alkyl, typically hydrogen or methyl; and
  $x^2$ is an integer from 5 to 30.

Yet in other further embodiments, methods of the invention can further include the steps of deprotecting said protected di-lipid carbohydrate of Formula II to produce an enantiomerically enriched surfactant di-lipid carbohydrate of the formula:

Formula II-A

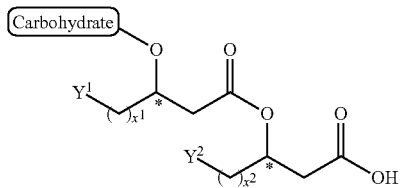

wherein
Y$^1$, x$^1$, and * are those defined herein, where each chiral center * is independent of each other;
x$^1$ is an integer from 5 to 30;
Y$^2$ is selected from the group consisting of hydrogen, ethylenyl, ethynyl, halide, —SH, —NH$_2$, and —CO$_2$H; and
x$^2$ is an integer from 5 to 30.

In some embodiments, the enantiomerically enriched alcohol compound of Formula B is produced by an enzymatic kinetic resolution. Typically, the enzymatic kinetic resolution comprises contacting a compound of the formula:

Formula B-1'

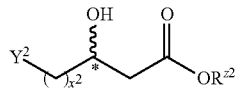

with an esterase in the presence of an ester compound of the formula R$^a$O—C(=O)—R$^x$ under conditions sufficient to produce a mixture of an enantiomerically enriched alcohol compound of the formula:

B-2$^a$

Formula B-2$^a$

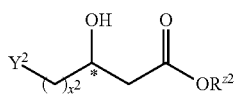

and an enantiomerically enriched ester compound of the formula:

Formula B-2$^b$

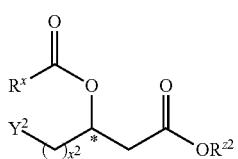

wherein
R$^x$ is alkyl, and
R$^a$, x$^2$, Y$^2$, and R$^{z2}$ are those defined herein,
and wherein
when compound of Formula B-2$^a$ has a same stereochemistry as compound of Formula B then separating said compound of Formula B-2$^a$ from said mixture to obtain said enantiomerically enriched alcohol compound of Formula B; and
when said compound of Formula B-2$^b$ has a same stereochemistry as compound of Formula B, then:

(i) separating compound of Formula B-2$^b$ from said mixture;
(ii) producing compound of Formula B by hydrolyzing an ester group of said compound of Formula B-2$^b$.

Still in other embodiments, said enzymatic kinetic resolution produces at least about 85% ee, typically at least about 90% ee, often at least about 95% ee, and most often at least about 98% ee of compound of Formula B.

DETAILED DESCRIPTION OF THE INVENTION

Figure 1:
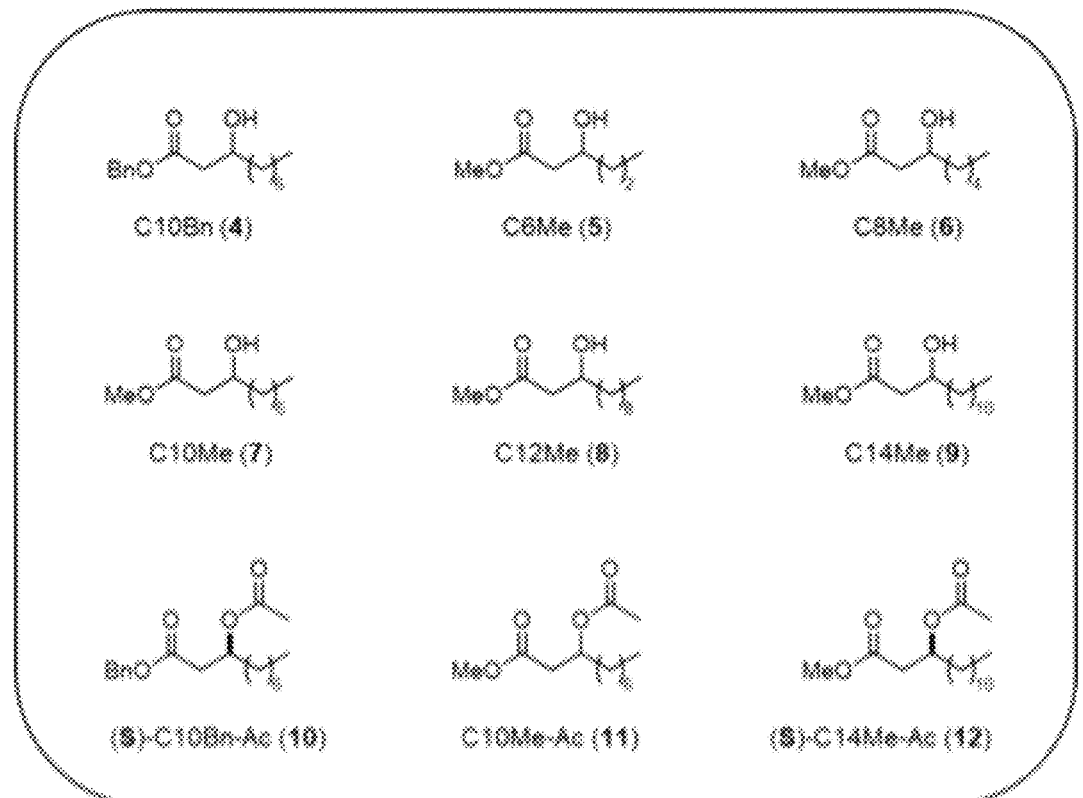
FIG. 1 shows some of the representative 3-hydroxydecanoates ("tails" or moiety "B") produced in the synthesis of carbohydrate-based biosurfactants. All entries are considered racemic unless otherwise noted in the text.

Some aspects of the present invention provide methods for producing stereoisomerically enriched carbohydrate-based surfactants. In some embodiments, methods of the invention provide stereoisomerically enriched carbohydrate-based surfactants of the formulas:

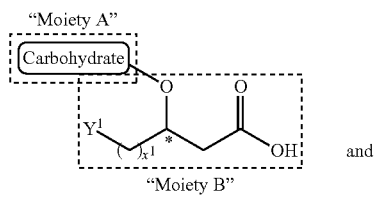

"single tail carbohydrate-based surfactant"

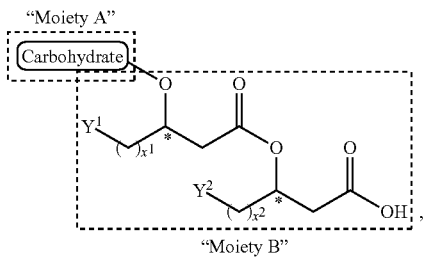

"double-tail carbohydrate-based surfactant"

where Y$^1$, x$^1$, Y$^2$, x$^2$, and * are those defined herein. It should be appreciated that the carbohydrate can optionally be a protected carbohydrate. It should also be noted that the linkage between the carbohydrate (or a protected carbohydrate) and the hydrophobic moiety (i.e., moiety B) can be α- or β-anomeric linkage.

One particular aspect of the invention provides a stereoselective method for producing a protected carbohydrate-based surfactant of the formula:

Formula I

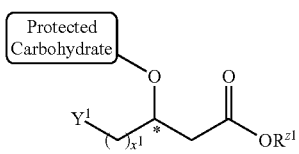

The method includes contacting an enantiomerically enriched alcohol compound of the formula:

Formula A

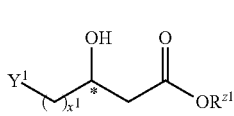

with a protected carbohydrate under conditions sufficient to form a covalent bond between said carbohydrate and said compound of Formula A to produce said protected carbohydrate-based surfactant of Formula I, wherein
a carbohydrate of said protected carbohydrate is selected from the group consisting of a monosaccharide, a disaccharide, a trisaccharide and a derivative thereof,
$Y^1$ is selected from the group consisting of hydrogen, ethylenyl, ethynyl, halide, —SH, —NH$_2$, and —CO$_2$R$^s$;
$R^{z1}$ is hydrogen, alkyl, benzyl, or a carboxylic acid protecting group;
$R^s$ is hydrogen or alkyl;
$x^1$ is an integer from 5 to 30; and
* is a chiral center.

In some embodiments, compound of Formula A has at least 85% ee, typically at least about 90% ee, often at least about 95% ee, and most often at least about 98% ee.

As used herein, the term "about" or "approximately" as used herein when referring to a numerical value refers to being within an acceptable error range for the particular value as determined by one of ordinary skill in the art, which will depend in part on how the value is measured or determined, i.e., the limitations of the measurement system, i.e., the degree of precision required for a particular purpose. For example, the term "about" can mean within 1 or more than 1 standard deviation, per the practice in the art. Alternatively, the term "about" when referring to a numerical value can mean ±20%, typically ±10%, often ±5% and more often ±1% of the numerical value. In general, however, where particular values are described in the application and claims, unless otherwise stated, the term "about" means within an acceptable error range for the particular value.

The term "sugar" and "carbohydrate" are used interchangeably herein and generally refers to a mono-, di, and/or trisaccharide or mixtures thereof. The term "monosaccharide" refers to any type of hexose of the formula $C_6H_{12}O_6$ or a derivative thereof. The ring structure (i.e., ring type) of the monosaccharide can be a pyranose or a furanose. In addition, the monosaccharides can be an α- or β-anomer. Monosaccharide can be a ketonic monosaccharide (i.e., ketose), an aldehyde monosaccharide (i.e., aldose), or any type of hexose of the formula $C_6H_{12}O_6$ or a derivative thereof. Exemplary monosaccharides of the invention include, but are not limited to, allose, altrose, arabinose, fructose, galactose, glucose, gulose, idose, lxyose, psicose, rhamnose, ribose, ribulose, sorbose, tagatose, talose, xylose, xylulose, and derivative thereof. Each monosaccharide can also be independently an (L)-isomer or a (D)-isomer. The term "disaccharide" refers to a carbohydrate composed of two monosaccharides. It is formed when two monosaccharides are covalently linked to form a dimer. The linkage can be a (1→4) bond, a (1→6) bond, a (1→2) bond, a (1→3) bond, etc. between the two monosaccharides. In addition, each of the monosaccharides can be independently an α- or β-anomer. Exemplary disaccharides that can be used in the present invention include, but are not limited to, cellobiose, chitobiose, dirhamnose, gentiobiose, isomaltose, isomaltulose, lactose, lactulose, laminaribose, leucrose, maltose, maltulose, melibiose, nigerose, sophorose, sucrose, terhalose, turanose, xylobiose, etc. Each of the monosaccharides can independently be a ketonic monosaccharide (i.e., ketose), an aldehyde monosaccharide (i.e., aldose), or any type of hexose of the formula $C_6H_{12}O_6$ or a derivative thereof. Each monosaccharide can also be independently an (L)-isomer or a (D)-isomer. The term "trisaccharide" refers to a carbohydrate composed of three monosaccharides. It is formed when three monosaccharides are covalently linked to form a trimer. Each of the linkage between monosaccharides can be independently a (1→4) bond, a (1→6) bond, a (1→2) bond, a (1→3) bond, etc. In addition, each of the monosaccharides can be independently an α- or β-anomer. Exemplary trisaccharides that can be used in the present invention include, but are not limited to, cellotriose, isomaltotriose, isopanose, laminaritriose, manninotriose, maltotriose, melezitose, nigerotriose, panose, raffinose, xylotriose, and the like. Each of the monosaccharides can independently be a ketonic monosaccharide (i.e., ketose), an aldehyde monosaccharide (i.e., aldose), or any type of hexose of the formula $C_6H_{12}O_6$ or a derivative thereof. Each monosaccharide within the trisaccharides can also be independently an (L)-isomer or a (D)-isomer.

When referring to a carbohydrate, the term "derivative thereof" refers to a derivative of a carbohydrate in which one or more of the hydroxyl groups is replaced with hydrogen (e.g., 2-deoxy glucose, 5-deoxyglucose, etc.), an amine (e.g., amino sugars), a thiol (—SH) or a halogen, such as chloro, fluoro or iodo, (e.g., 5-fluoroglucose, 2-fluoroglucose, 5-chrologlucose, 2-chloroglucose, etc.). In addition, each of the monosaccharides can be an (L)-isomer or a (D)-isomer. The term "a thiol derivative" of a sugar refers to a sugar moiety in which the hydroxyl group that links the "B" moiety is replaced with a sulfur atom, i.e., the linkage between A and B moieties is sulfur.

Generally, the carbohydrate-based surfactants of the invention comprise a carbohydrate moiety that is covalently linked to a nonpolar or hydrophobic moiety (i.e., moiety B) having a terminal carboxylic acid.

The term "alkyl" refers to a monovalent saturated linear monovalent hydrocarbon moiety or a saturated branched monovalent hydrocarbon moiety of six to thirty, typically six to twenty-two, often six to twenty and more often six to eighteen carbon atoms. Exemplary nonpolar alkyl groups include, but are not limited to, hexyl, decyl, dodecyl, tetradecyl, hexadecyl, octadecyl, and the like. The term "alkenyl" group refers to a linear monovalent hydrocarbon moiety or a branched monovalent hydrocarbon moiety having at least one carbon-carbon double bond in which the total carbon atoms is six to thirty, typically six to twenty two, often six to twenty and more often six to eighteen. Exemplary nonpolar alkenyl groups include, but are not limited to, hexenyl, decenyl, dodecenyl, hexadeca-1,3-dienyl, docosa-hexaenyl, dodeca-2,4-dienyl, and the like. The term "alkynyl" group refers to a linear monovalent hydrocarbon moiety or a branched monovalent hydrocarbon moiety having at least one carbon-carbon triple bond in which the total carbon atoms is six to thirty, typically six to twenty two, often six to twenty and more often six to eighteen. Alkynyl group can optionally have one or more alkenyl moiety (i.e., carbon-carbon double bond). Exemplary nonpolar alkynyl groups include, but are not limited to, hexynyl, decynyl, dodecynyl, hexadeca-1,3-diynyl, dodecynyl, dec-1-en-3-ynyl and the like. The terms "halo," "halogen" and "halide" are used interchangeably herein and refer to fluoro, chloro, bromo, or iodo. The term "hydrocarbon" includes alkyl, alkenyl, or alkynyl as defined herein. It should be appreciated that one or more of the hydrogens in alkyl, alkenyl, or alkynyl may be substituted with halide. Unless stated otherwise, hydrocarbon can also include a cyclic (alkyl, alkenyl or alkynyl) group or an aryl group. Preferred hydrocarbons are alkyl, alkenyl, alkynyl, cyclic alkyl, cyclic alkenyl, or cyclic alkynyl. The term "hydrophobic" group refers to any moiety having at least six carbon atoms in which in the absence of the hydrophilic portion of the surfactant is substantially immiscible or insoluble in aqueous solution. Typically, solubility of the parent hydrophobic group (i.e., where the hydrophilic portion of the surfactant is replaced with hydrogen or the corresponding functional group) in water is about 10 g/L or less, often 1 g/L or less, more often 0.5 g/L or less, and most often 0.1 g/L or less. The hydrophobic group can have other functional groups (e.g., ether, ester, halide, etc.) as long as the solubility of the parent compound satisfies the conditions set forth herein. Thus, the term hydrophobic group includes hydrocarbons defined herein as well as lipids, and other groups in which the parent compound meets the conditions set forth herein.

The term "derivative" generally refers to any chemical modification of the parent compound or a compound derived from the parent compound. For example, a derivative of a carbohydrate includes alkylated carbohydrate, replacement of one or more hydroxyl groups with hydrogen, halide, amine, or a thiol; modification of a hydroxyl group (e.g., by esterification, etherification, protection, etc.); as well as other derivatives known to one skilled in the art. The term carbohydrate includes pyranose and furanose carbohydrates. Exemplary derivatives of carbohydrates include, but are not limited to, alkylated carbohydrate (e.g., one or more hydroxyl groups that are methylated, ethylated, acetylated, or benzoylated), thiol carbohydrate (where one or more hydroxyl groups are replaced with —SH moiety), deoxy carbohydrates (where one or more —OH groups of the carbohydrate is replaced with —H), etc.

"Protecting group" refers to a moiety, except alkyl groups, that when attached to a reactive group in a molecule masks, reduces or prevents that reactivity. Examples of protecting groups can be found in T. W. Greene and P. G. M. Wuts, *Protective Groups in Organic Synthesis*, 3$^{rd}$ edition, John Wiley & Sons, New York, 1999, and Harrison and Harrison et al., *Compendium of Synthetic Organic Methods*, Vols. 1-8 (John Wiley and Sons, 1971-1996), which are incorporated herein by reference in their entirety. Representative hydroxy protecting groups include acyl groups, benzyl and trityl ethers, tetrahydropyranyl ethers, trialkylsilyl ethers and allyl ethers. Representative amino protecting groups include, formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), and the like.

"Corresponding protecting group" means an appropriate protecting group corresponding to the heteroatom (i.e., N, O, P or S) to which it is attached.

When describing a chemical reaction, the terms "treating", "contacting" and "reacting" are used interchangeably herein, and refer to adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

"Enantiomeric excess" refers to the difference between the amount of one enantiomer compared to the other enantiomer. The percentage of enantiomeric excess (% ee) can be calculated by subtracting the percentage of one enantiomer from the percentage of the other enantiomer. For example, if the % ee of (R)-enantiomer is 99% and % ee of (S)-enantiomer is 1%, the % ee of (R)-isomer is 99%-1% or 98%. Similarly, the term "diastereomeric excess" or "% de" refers to the difference between the amount of one diastereomer compared to other diastereomer(s).

For sake of brevity and clarity, the present invention will now be described with regard to stereoisomerically enriched rhamnolipids. However, it should be appreciated that this disclosure merely assists in illustrating various features of the invention. In this regard, the present invention generally relates to methods for producing stereoisomerically enriched carbohydrate-based surfactants. As stated above, methods of the invention can be used generally to synthesize or produce stereoisomerically, in particular, enantiomerically enriched carbohydrate-based surfactants. Discussion of producing enantiomerically enriched rhamnolipids is provided solely for the purpose of illustrating the practice of the invention and do not constitute limitations on the scope thereof.

In general, rhamnose used as an illustration of the invention can be replaced with any other carbohydrates. Furthermore, the hydrophobic moiety "B" can be replaced with other similar non-polar compounds having a hydroxy functional group and a terminal carboxylate moiety.

One of the steps in the synthesis of stereoisomerically enriched carbohydrate-based surfactant is production of an ester protected 3-hydroxyalkanoate tail, i.e., non-polar or hydrophobic moiety "B." The term "tail" refers to a monomeric or dimeric 3-hydroxyalkanoate moiety. In one particular embodiment, the terms "monomeric tail" and "dimeric tail" refer to a moieties of the formula:

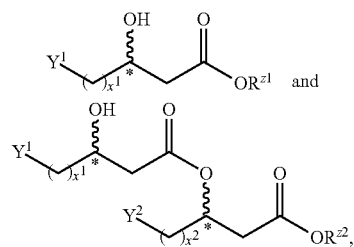

respectively, where $Y^1$, $x^1$, $R^{z1}$, $Y^2$, $x^2$, $R^{z2}$, and * are those defined herein. As used herein, the terms "those defined above" and "those defined herein" when referring to a variable incorporates by reference the broad definition of the variable as well as any narrower definition(s), if any.

In the synthesis of single-tail rhamnolipid (Rha-C10, i.e., where "A" is rhamnose and B is 3-hydroxydecanoate), two diastereomers are possible whereas in the case of two-tail monorhamnolipids (Rha-C10-C10), four diastereomers are possible. The tail racemate necessitates the synthesis and separation of all rhamnolipid diastereomers and the lack of diastereomeric control is not only problematic from a purity standpoint, but the separation of the diastereomers is solvent intensive and can therefore be considered to dramatically hamper the industrial applicability and greenness of the synthesis. Methods of the invention overcome these and other problems.

Some embodiments of the invention include producing enantiomerically enriched 3-hydroxyalkanoates. As an illustrative purposes only, the invention will be described for the production of 3-hydroxyalkanoates esters having a total chain length of 6, 8, 10, 12, and 14. See FIG. 1. In the following illustration, 3-hydroxyalkanoates of chain lengths of 10 and 14 are discussed. However, as stated above, it should be appreciated that the scope of the invention is not limited to these particular chain lengths. In fact, the scope of the invention includes 3-hydroxyalkanoates with any chain length, with a minimum being 4. In some embodiments, 3-hydroxyalkanoate has a total of 4-50, typically 6-25, and often 6-20 carbon atoms in chain length.

3-Hydroxyalkanoates can be prepared using any methods known to one skilled in the art. In particular method for producing 3-hydroxyalkanoates is using a Reformatsky reaction between an ester of bromoacetate and an aldehyde compound. A general procedure for producing 3-hydroxyalkanoate via a Reformatsky condensation was as follows: zinc metal gratings (4.0 eq., 30-40 mesh) were added to dry, refluxing tetrahydrofuran (THF) (100-200 mL dependent upon scale) and allowed to boil in a round bottom flask (RBF) for 20-30 min. Subsequently octyl aldehyde (1.0 eq.) and benzyl bromoacetate (2.0 eq.) were added simultaneously. The reaction was allowed to react for 20-30 min at 70° C. and was then brought to RT while stirring for 3-4 h. For this methodology the molar equivalents of methyl/benzyl bromoacetate and zinc metal were 2.0 and 4.0, respectively.

For methyl ester 3-hydroxyalkanoates (referred to herein as CnMe, where n is the number of carbon atoms in the chain) synthesized using the refluxing method, yields averaged around 40% for multi-gram scale reactions. Using the procedures described herein, the following methyl ester 3-hydroxyalkanoates were prepared: C6Me, C10Me, C12Me, and C14Me. FIG. 1. The Reformatsky condensation via refluxing THF is an extremely exothermic and vigorous reaction. All reagents are added quickly to refluxing. To overcome this synthetic drawback, an activation method using sonication can be used as described by Compton et al., in *ACS Sustainable Chem. Eng.* 2020, 8 (24), 8918-8927. doi.org/10.1021/acssuschemeng.0c00733. Briefly, this method consisted of sonication of zinc metal and aldehyde in dry THF typically for 10-25 min. While continuing sonication, the methyl bromoacetate (MBA) was added dropwise. Sonication usually continued for an hour or more after MBA addition and the crude product was obtained after aqueous acidic work-up. In this methodology, a vigorous reaction is observed 20-40 min after addition of all reagents. However, in contrast to the reflux method, the sonicated reaction is of considerably less volume and is not being externally heated. These two factors minimize the potential for uncontrolled reactions and significantly reduce danger. Furthermore, the sonication method is less laborious than the reflux method.

The molar ratios of aldehyde to MBA is typically from about 1 equivalent to about 2.5 equivalents, typically from about 1.1 equivalents to about 2.0 equivalents. However, it should be appreciated that the scope of the invention is not limited to these particular molar ratios, but can vary depending on a wide variety of reaction conditions including, but not limited to, aldehyde compound used, reaction temperature, intensity of sonication, concentration of the reagents, etc. Similarly, the molar ratio of aldehyde to zinc metal can range from about 1.0 equivalents to about 5.0 equivalents, typically from about 1.0 equivalent to about 4.0 equivalents. In addition, the variables of reaction scale (referencing the starting mass of aldehyde), reagent addition order, addition speed, sonication bath temperature, and zinc addition can also vary. This sonication method was used to prepare C6Me, C8Me, C10Me, and C14Me compounds under various reaction conditions. As an illustrative example, typical results of producing C10Me compound under various reaction conditions is provided in Table 1.

TABLE 1

Reaction Conditions and Yields for Sonicated C10Me Reformatsky Synthesis

| Scale of octyl aldehyde | Zinc Equiv.[a] | MBA Equiv. | MBA Addition | Zinc High-Temp. Activation[b] | Iced Sonication Bath | % Yield |
|---|---|---|---|---|---|---|
| 2 g | 2.0 | 1.2 | Slow | No | No | 46% |
| 3 g | 4.0 | 1.2 | Slow | No | No | 36% |
| 4 g | 1.0 | 1.2 | Slow | No | No | 33% |
| 4 g | 1.0 | 1.2 | Slow | No | Yes | 21% |
| 4 g | 1.24 | 1.2 | Slow | No | Yes | 33% |
| 4 g | 1.24 | 1.2 | Slow | Yes | Yes | 33% |
| 6 g | 1.5 | 1.1 | Slow | Yes | Yes | 28% |
| 6 g | 1.5 | 1.1 | Fast | Yes | Yes | 22% |
| 6 g | 1.5 + 0.33 | 1.1 | Slow | No | No | 19% |
| 6 g | 2.0 + 1.0 | 1.5 | Slow | Yes | No | 28% |

Yields of 56-60% were achieved at a 4.0 g scale of starting octyl aldehyde. Some of the representative esters of 3-hydroxyalkanoic acid of various length that were prepared using the Reformatsky reaction is shown in FIG. 1.

Generally, the variables of molar equivalency of aldehyde to MBA/zinc allow for either increase or decrease in reactivity as appropriate. The MBA addition can also be modulated to be either slow (dropwise) or fast (all-at-once addition). The zinc metal was activated by either sonication alone or was baked at 300° C. prior to sonication to remove the zinc oxide layer and thereby increase reactivity. The sonication water bath temperature can be adjusted to modulate the reaction speed. These variables can be employed alone or in combination at different scales to balance the factors influencing reactivity and to improve yields.

As can be seen in Table 1, typically the reaction yield decreases as the scale of the aldehyde is increased. It is also observed between trials of the same scale that yield generally increases with greater equivalence of zinc. The methyl bromoacetate (MBA) was generally added slowly in a dropwise fashion, but it should be appreciated that it can also be added more quickly or all-at-once. As shown in Table 1, in some experiments the sonication bath was cooled to 0° C. with ice. This condition was thought to decrease reactivity; unregulated, the sonication bath temperature rises as high as 50° C. over the course of the reaction which is greater than would be expected with sonication alone. At a 4 g scale where MBA and zinc ratios were the same, the ice bath alone caused the reaction yield to decrease from 33% to 21%. The yield could be rescued back to 33% with the ice bath by increasing the equivalency of zinc from 1.0 to 1.24. In general, fast addition of MBA was found to decrease the yield. Zinc can be added all at once or in portions. At a 6 g reaction scale of aldehyde, the two-portion methodology with greater total molar equivalence of zinc generally gave a higher yield.

In the synthesis of ester protected 3-hydroxyalkanoates, a sonication method was found to be synthetically less laborious and, in some cases, better yielding than a reflux-activation method. It was found that chain-length and scale of the aldehyde are some of the key factors determining yield where longer chain-length and smaller scale generally provided better yields.

Design of a Chemoenzymatic Method

One of the key requirements in methods of the invention is starting from an enantiomerically enriched 3-hydroxyalkanoate. As it is readily apparent, when a racemic mixture of 3-hydroxyalkanoate compound is used it is necessary to separate the resulting diastereomers to obtain stereoisomerically enriched carbohydrate-based surfactants, which is often labor intensive, costly, and time consuming. To avoid these problems, methods of the invention utilize an enantiomerically enriched 3-hydroxyalkanoate compound to link to a carbohydrate.

For a stereo-controlled synthesis of carbohydrate-based surfactants, e.g., rhamnolipids, several approaches for the production of enantiomerically enriched 3-hydroxyalkanoate tails were explored by the present inventors. Based on the extensive research, methods of the invention utilize an enzyme of a biocatalyst to produce compound of Formula A. Biocatalysts are extremely specific, often in both regio- and stereoselectivity. Biocatalysis can be used for a wide range of substrates and synthetic transformations. Often use of biocatalysts can provide enantiomerically pure compounds or compounds having at least about 85% ee, typically at least about 90% ee, often at least 95% ee, and most often at least about 98% ee.

Some methods of the invention use a racemic mixture of 3-hydroxyalkanoate ester of Formula A and an enzyme, to produce stereoisomerically or enantiomerically enriched 3-hydroxyalkanoate esters. In particular, said enantiomerically enriched alcohol compound of Formula A is produced by an enzymatic kinetic resolution. The enzymatic kinetic resolution comprises contacting a compound of the formula:

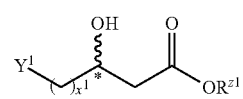

Formula A-1 with an esterase in the presence of an ester compound of the formula $R^aO-C(=O)-R^x$ under conditions sufficient to produce a mixture of an enantiomerically enriched alcohol compound of the formula:

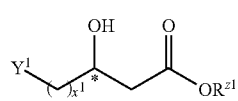

Formula A-2$^a$ and an enantiomerically enriched ester compound of the formula:

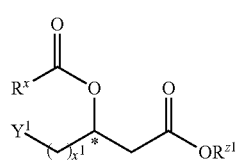

Formula A-2$^b$ wherein $R^a$, $R^x$, $x^1$, $Y^1$, and $R^{z1}$ are those defined herein.

As can be seen the esterase links the $R^a$ moiety in the ester compound of the formula $R^aO-C(=O)-R^x$ to the 3-hydroxy moiety of compound of Formula A-1. This esterification is a stereoselective process, i.e., the enzyme favors one of the stereoisomers of compound of Formula A-1 in this esterification process.

Enzymes that can be used in methods of the invention include, but are not limited to, esterases such as triacylglycerol lipase; GA 56; GEH; Meito MY 30; PPL; Takedo 1969-4-9; Tween hydrolase; Tweenase; Tweenesterase; amano AP; amano B; amano CE; amano CES; amano P; amno N-AP; butyrinase; cacordase; capalase L; glycerol ester hydrolase; glycerol-ester hydrolase; heparin releasable hepatic lipase; hepatic lipase; hepatic monoacylglycerol acyltransferase; lipase; lipazin; liver lipase; meito Sangyo OF lipase; post-heparin plasma protamine-resistant lipase; salt-resistant post-heparin lipase; steapsin; triacetinase; triacylglycerol ester hydrolase; tributyrase; tributyrin esterase; tributyrinase; triglyceridase; triglyceride hydrolase; triglyceride lipase; triolein hydrolase; and tween-hydrolyzing esterase. Typically any triacylglycerol acyl hydrolase-EC 3.1.1.3 (lipase) listed in the Enzyme Commission database (see, for example, enzyme.expasy.org/EC/3.1.1.3) or other esterases that are known to one skilled in the art can be used.

In one particular embodiment, Lipase B of the yeast *Candida antarctica* (CALB) is used in methods of the invention. It should be appreciated that other esterases disclosed herein can also be used. Use of CALB is discussed herein solely for the purpose of illustrating methods of the invention and should not be construed as limiting the scope of the invention. While one can use free form of CALB, for ease of separation, an immobilized CALB is used. CALB that is immobilized on a polymer resin is commercially available under the product name Novozym 435® (referred to herein as "N435"). CALB catalyzes the hydrolysis of triglycerides and is classified with the Enzyme Commission number 3.1.1.3, a hydrolase acting on carboxylic esters. The hydrolysis activity of CALB is its native catalytic mode and it has evolved to accept a large number of substrates due to the wide structural variability of triglyceride substrates in the cell. This catalytic promiscuity of CALB is one of its major advantages and permits substrates of both natural and unnatural origin. In nonaqueous media the native hydrolytic activity of CALB is reversed and asymmetric esterification and transesterification become possible. Transesterification of a sec-alcohol (i.e., secondary alcohol, such as 3-hydroxycarboxylate) substrate is achieved by incubation of the lipase with the substrate in the presence of an acyl donor either with or without additional organic solvent. Without being bound by any theory, it is believed that the acyl donor (e.g., an ester compound $R^aO—C(=O)—R^x$, where $R^a$ and $R^x$ are those defined herein) binds the enzyme first to give the acyl-enzyme complex that can then react with the substrate alcohol (e.g., 3-hydroxycarboxylate) to give the acetoxy product, e.g., compound of Formula A-2b. The acyl donor should be selected as to avoid product inhibition or competition. An exemplary suitable choice is vinyl acetate (VA) which upon formation of the acyl-enzyme produces an equivalent of vinyl alcohol. Vinyl alcohol rapidly and preferentially tautomerizes into acetaldehyde (bp 20° C.) which is not a substrate for CALB and is readily removed.

In some embodiments, when compound of Formula A-$2^a$ has the desired stereochemistry, i.e., has a same stereochemistry as compound of Formula A, then methods of the invention include separating said compound of Formula A-$2^a$ from said mixture to obtain said enantiomerically enriched alcohol compound of Formula A. In this manner, separated compound of Formula A-$2^a$ is used directed to link to a carbohydrate.

Yet in other embodiments, when the desired stereochemistry is present in said compound of Formula A-$2^b$ (i.e., has a same stereochemistry as compound of Formula A) then methods of the invention also include:
(i) separating compound of Formula A-$2^b$ from said mixture;
(ii) producing said enantiomerically enriched alcohol compound of Formula A by hydrolyzing an ester group of said compound of Formula A-$2^b$.

Kinetic Resolution of the Ester Protected 3-Hydroxyalkanoate System

For the kinetic resolution of ester protected 3-hydroxyalkanoates by CALB, the enantiopreference of the enzyme was first determined. Empirical rule for the prediction of lipase enantiopreference for a given substrate has been hypothesized. See, for example, Azlauskas et al., *J. Org. Chem.* 1991, 56 (8), 2656-2665. doi.org/10.1021/jo00008a016. Briefly, the preferred enantiomer is the one that when the secondary alcohol is drawn proximally, or 'up', the larger substituent is on the right-hand side. This empirical rule implies that simple CIP designation of substrate will not allow determination of enantiopreference, and a spatial analysis must be done. The rule is explained by the lipase's active site structure which is subdivided into an acyl binding pocket, a large binding pocket, and a medium binding pocket. Without being bound by any theory, it is believed that the acyl binding pocket is where the canonical serine-histidine-aspartate catalytic triad residues are located that perform hydrolysis/esterification. The large and medium binding pockets incorporate the substituents at the secondary alcohol and serve to discriminate between the two enantiomers of a given substrate. As the names imply, the large pocket binds larger substituents and comprises largely hydrophobic amino acids while the medium binding pocket is more shallow and comprises threonine, serine, and tryptophan residues. The preferred enantiomer allows for matched binding between substituent and pocket.

Figure 2:
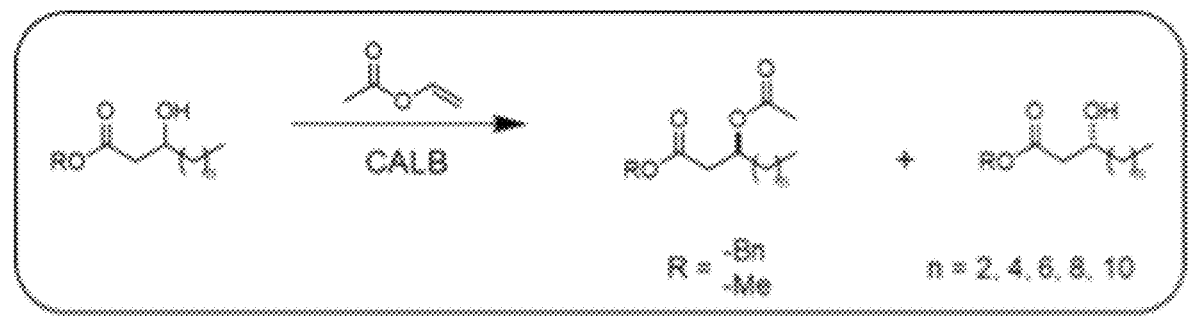
FIG. 2 illustrates a generalized scheme for the resolution of an ester 3-hydroxyalkanoate by CALB with vinyl acetate acyl donor.

In the case of ester protected 3-hydroxyalkanoates, it was hypothesized that the (S)-enantiomer would be the preferred enantiomer as shown in FIG. 2. To test this hypothesis, resolution of racemic benzyl-3-hydroxydecanoate (C10Bn) was first attempted using the following synthetic procedure: To C10Bn dissolved in 15 mL of a dry organic solvent (either ACN, hexanes, or toluene) was added an equal mass of CALB immobilized resin (Novozym® 435, Strem Chemicals) and vinyl acetate (2-11 equivalents). The reaction was allowed to proceed while covered at room temperature while agitating on an orbital shaker for 48-72 h. The reaction was monitored by TLC and/or NMR and the endpoint was determined when the conversion to product had ceased. For this substrate, it was found that conversion to the acetoxy product (C10Bn-Ac) was only achieved in poor yield. The reaction solvent had a dramatic impact on the yields with hexanes being the worst, acetonitrile being marginal, and toluene being the best. Of the solvents explored, it was found that kinetic resolutions conducted in a solvent of moderate hydrophobicity (e.g., toluene) generally gave better conversion yields under similar conditions. This result suggests that CALB transesterification is disfavored by extremely hydrophobic solvents (hexanes) and moderately polar solvents (acetonitrile, i.e., "ACN") alike, and that conversion yields are favored in hydrophobic solvents that exhibit sparing polarity.

As discussed above, the enzyme active site has steric and spatial restrictions that determine its ability to bind substrates. Researchers have found that the medium pocket has difficulty binding anything larger than an ethyl group. The benzyl protected ester of 3-hydroxyalkanoate has two groups which may be considered large, and the conversion yields suggest that, indeed, the enzyme struggles to incorporate and catalyze the transesterification reaction with this substrate.

In addition to benzyl 3-hydroxyalkonates, methyl esters of 3-hydroxyalkanoate as a kinetic resolution substrate were also studied. Racemates of methyl 3-hydroxydecanoate (C10Me, FIG. 1 compound 7) were explored. General conditions for the resolution of C10Me racemate were: methyl 3-hydroxy decanoate (500 mg, 2.471 mmol) was dissolved in 15 mL toluene and combined with an equal mass of N435 (500 mg) and an excess of vinyl acetate (2.55 g, 29.66 mmol). The reaction was allowed to proceed at room temperature for 72 h and was monitored by TLC and NMR. The results are summarized in Table 2.

TABLE 2

Kinetic Resolution of methyl 3-hydroxydecanoate with CALB

| Solvent | $C_{10}$Me Mass | CALB Mass | Vinyl Acetate Eq. | $C_{10}$Me—Ac Mass (Product) | % Conversion |
|---|---|---|---|---|---|
| Toluene | 1.0 g | 1.0 g | 12 (5.56 g) | 489 mg | 45.0% |

Figure 3:
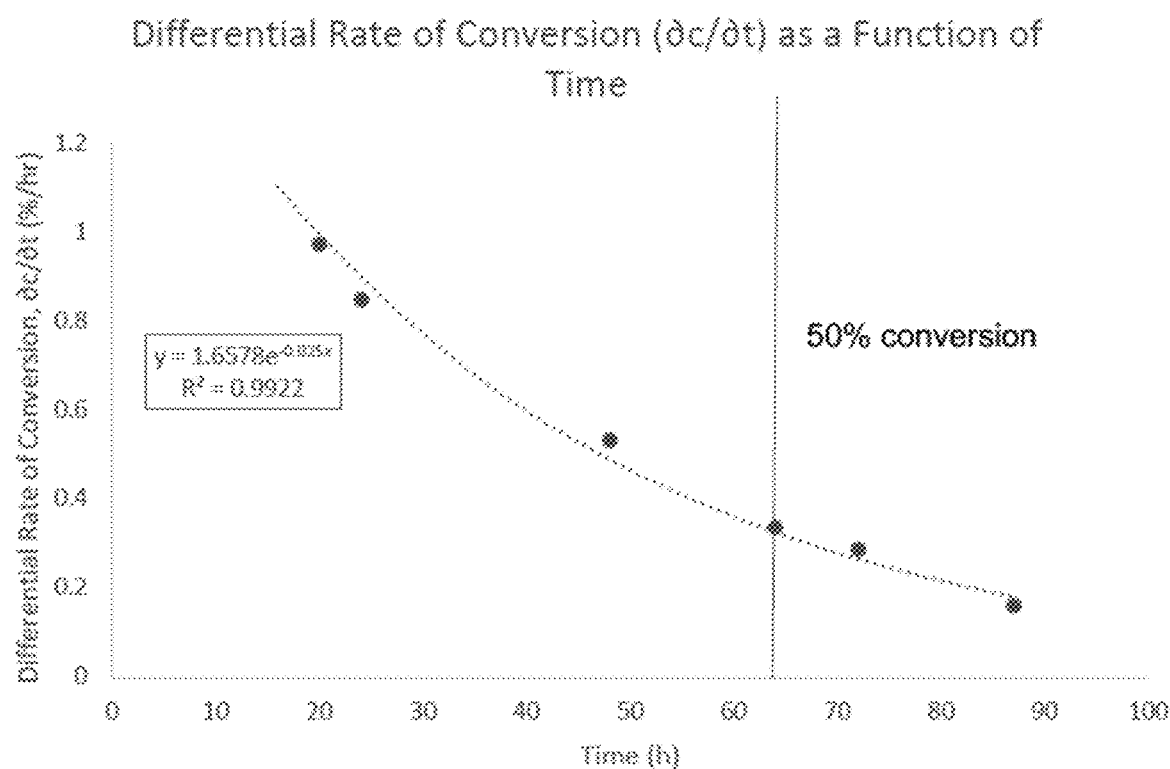
FIG. 3 is a plot of rate of conversion versus time for a kinetic resolution of C10Me by N435 with vinyl acetate acyl donor and diisopropyl ether (DIPE) reaction media. Vertical line indicates timepoint of approximately 50% conversion.

The endpoint conversion of 45% in the initial experiment suggested that the enzyme was performing an enantioselective kinetic resolution of the substrate racemate. An idealized kinetic resolution of a racemate has a maximal percent conversion of 50%. Experiments were performed to monitor the reaction progress at room temperature to better understand the resolution time course. Quantitative reaction monitoring was accomplished by NMR spectroscopy. Small (~10 µL) aliquots of the reaction mixture were removed throughout the resolution, the solvent was evaporated, and the remaining oil was dissolved in a suitable deuterated solvent (CDCl$_3$) for the acquisition of a $^1$H NMR spectrum to determine kinetic resolution ("KR") rate. Monitoring past 64 h showed that the conversion yield did not significantly increase beyond 50% and that the resolution time course in diisopropyl ether (DIPE) at room temperature is approximately 2.5 days. The differential rate of conversion over the course of the resolution can be estimated algebraically by the following equation:

$$\frac{\partial c}{\partial t} \cong \frac{c_{i+1} - c_i}{t_{i+1} - t_i}$$

where $c_i$ is the percent conversion at time $t_i$. The plot of rate of conversion versus time is given in FIG. 3.

The rate of conversion is given as the percent of the initial substrate population (C10Me) converted to product (C10Me-Ac) per hour. The rate of conversion by N435 for this system decreases exponentially with time. For a resolution with 500 mg of C10Me starting substrate mass, the rate at hour 20 is 1%/hr or approximately 6 mg of product formed per hour. By hour 20 the overall conversion yield is 28% and the reaction has passed the halfway mark for a typical kinetic resolution. This data suggests that the initial velocity of the enzyme is quite high, fed by a high substrate population, and quickly drops requiring double the time to reach completion as to meet the halfway point. Although the rate drops as the reaction nears 50% conversion, it is non-zero and even at 88 h the rate is ~0.1%/hr or 0.6 mg product/hr (for 500 mg starting C10Me).

In some embodiments, the enzyme can be recovered and reused. To understand the reusability of a portion of N435 after a KR the following procedure for the N435 reuse study was conducted: C10Me (500 mg, 2.471 mmol) was dissolved in 10 mL DIPE and was combined with vinyl acetate (2.13 g, 24.71 eq.) and an equal mass of N435 (500 mg) in a capped 250 mL RBF. The resolution was allowed to proceed at room temperature while agitating on an orbital shaker. The NMR-monitored reaction was halted at the endpoint by filtering the reaction through filter paper (Whatman), washing the enzyme 3× with ethyl acetate and hexanes, and allowing it to air dry. The dried resin was reused in a kinetic resolution identical to the above for a total of five resolutions. A summary of quantitative conversion is given in Table 3.

TABLE 3

Reuse Study for a Single Portion of N435 Resin over Three KR's

| Time (hours) | Resolution 1 | Resolution 2 | Resolution 3 |
| --- | --- | --- | --- |
| 16 | 23% | — | — |
| 20 | 28% | — | — |
| 24 | 30% | 34% | 30% |
| 48 | 44% | 46% | 42% |
| 52 | — | 49% | — |
| 64 | 49% | — | 48% |
| 72 | 51% | 56% | 52% |
| 88 | — | 55% | 55% |

As shown in Table 3, a single portion of N435 resin's ability to produce C10Me-Ac is not hindered over the course of the first three independent kinetic resolutions. In fact, the second resolution (middle column) shows somewhat accelerated conversion at individual timepoints compared to the first and third resolutions. The third resolution (last column) shows comparable conversion values to the first resolution at each timepoint. Thus, the N435 resin is able to resolve at least 3-times its mass of C10Me substrate. The reuse study also confirms that the 50% conversion mark is reached somewhere near 2.5 days.

As can be seen, N435 is able to catalyze the conversion of C10Me to C10Me-Ac in an enantioselective fashion at room temperature. The rate of kinetic resolution at higher temperature was also studied. Common temperatures in nonaqueous media range from 30-60° C. The KR of C10Me at 50° C. was conducted to determine enantioselectivity. The procedure was as follows: vinyl acetate (10 mL, 108.5 mmol) without additional solvent was placed in a 250 mL round bottom flask and brought to 50° C. on a heating mantle while shaking. To the warmed VA was added C10Me (300 mg, 1.483 mmol) and N435 (750 mg). The reaction vessel was capped and externally covered with aluminum sheet to ensure even heating and the reaction temperature was monitored with an alcohol thermometer periodically. The resolution was monitored by TLC and NMR as described above. At 50° C., it was shown that the resolution nears 50% completion at just 24 h and at 33 h the conversion has not exceeded 52%. The overall time course to completion is about 2.5 times faster than that at room temperature. The rate of reaction is dramatically improved at elevated temperature and indeed, even at t=0 (just after initial mixing) evidence of the enzyme catalyzed conversion was observed.

In some embodiments, the enzyme is recovered and reused. Typically, the enzyme (e.g., N435 CALB) is recovered by filtration and the resin was washed. The substrate (e.g., 3-hydroxyalkanoate ester) can be added batch-wise or all at once. A more facile means to introduce substrate is by resolution in batches where new (racemic) substrate is simply added to the reaction mixture at intervals. The procedure for this study was as follows: vinyl acetate (10 mL, 108.5 mmol) without additional solvent was placed in a 250 mL round bottom flask and brought to 40° C. on a heating mantle while shaking. To the warmed VA was added 7 (1.0 g, 4.943 mmol) and N435 (500 mg). The reaction vessel was capped and externally covered with aluminum sheet to ensure even heating and the reaction temperature was monitored with an alcohol thermometer periodically. After 8 h had elapsed, an additional 1.0 g of 7 was added to the reaction vessel. An analytical aliquot was taken just before and after addition. After 32 h had elapsed, another 1.0 g of 7 was added and similarly two aliquots were taken before and after addition. The reaction was allowed to proceed for a total of 120 h before it was halted. The KR was monitored by NMR was described above.

It was discovered by the present inventors that N435 CALB resin is able to resolve 6-times its mass of the C10Me substrate. This is a 2-fold increase in loading efficiency as compared to the methodology employed for the reuse study. The synthetically more facile method above allows one to resolve C10Me substrate on the multigram scale and achieve nearly 50% conversion in 5 days. This study demonstrates a methodology that can be scaled up to resolve very large amounts of C10Me substrate. The enzyme efficiency does not deteriorate after the final addition of substrate (t"=0). From the percent conversion just before the final addition (27.5%) the percent conversion at t"=0 is expected to be 18.3%. However, at t"=0 the percent conversion is 20.6%. Immediately after addition of the fresh substrate, 2.3% of the substrate pool was converted evidencing the recovery of CALB's initial high conversion rate To more fully understand the effect of substrate loading on the enzyme resin and to further expand the resolution scale, two kinetic resolutions were run in parallel where resolution A used a batch addition and resolution B had substrate added all-at-once. The procedures were as follows: resolution A, vinyl acetate (10 mL, 108.5 mmol) without additional solvent was placed in a 250 mL round bottom flask and brought to 45° C. on a heating mantle while shaking. To the warmed VA was added 2.0 g of C10Me and 1.0 g N435 resin. The reaction vessel was capped and externally covered with aluminum sheet to ensure even heating and the reaction temperature was monitored with an alcohol thermometer periodically. After 48 h had elapsed an analytical aliquot was removed and an additional 2.0 g of C10Me was added to the reaction vessel. Another analytical aliquot was removed at 72 h. The reaction was allowed to proceed for a total of 144 h before it was halted. Resolution B, vinyl acetate (10 mL, 108.5 mmol) without additional solvent was placed in a 250 mL round bottom flask and brought to 45° C. on a heating mantle while shaking. To the warmed VA was added 4.0 g of C10Me and 1.0 g N435 resin. The reaction vessel was capped and externally covered with aluminum sheet to ensure even heating and the reaction temperature was monitored with an alcohol thermometer periodically. At 48 and 72 h analytical aliquots were removed. The reaction was allowed to proceed for a total of 144 h before it was halted.

The results showed the importance of initial conditions on the CALB catalyzed kinetic resolution. In both reactions A and B, the general metrics are the same: one gram of N435 is used to resolve 4.0 grams of C10Me, the reaction is performed in 10 mL of the acyl donor, vinyl acetate, without additional solvent, and both are conducted at 45° C. The difference between the two is the mode of substrate addition. In method A, the substrate was added in batches; specifically, half the substrate mass was added at the very start of the reaction and the other half was added just after 48 h had elapsed. In method B, all 4.0 grams of C10Me were added at the very beginning. At 48 h, it was observed that method A has gone to completion and even converted 4% beyond the KR endpoint whereas method B has only reached 32% conversion. At the endpoint (144 h) A had reached 51% conversion while reaction B only reached 41.5% conversion.

Interestingly, it was found that the recovered C10Me substrate from A had a greater optical purity (ee(S)$_A$=78.6%) than that of B (ee(S)$_B$=55.0%). This finding is significant; not only does the batch addition allow for the resolution of greater amounts of substrate by the same resin mass, but it also results in a more enantioselective resolution.

Two side-by-side KRs were performed where the solvent system and equivalence of vinyl acetate were explored. The procedures were as follows: A, 10 mL of 9:1 toluene to vinyl acetate was placed in a 250 mL round bottom flask and brought to 40° C. on a heating mantle while shaking. To the warmed solvent was added 2.0 g of C10Me and 1.0 g N435 resin. The reaction vessel was capped and externally covered with aluminum sheet to ensure even heating and the reaction temperature was monitored with an alcohol thermometer periodically. After 24 h and 48 h had elapsed an analytical aliquot was removed. The reaction was halted after 48 h. B, vinyl acetate (10 mL, 108.5 mmol) was placed in a 250 mL round bottom flask and brought to 40° C. on a heating mantle while shaking. To the warmed solvent was added 2.0 g of C10Me and 1.0 g N435 resin. The reaction vessel was capped and externally covered with aluminum sheet to ensure even heating and the reaction temperature was moni- tored with an alcohol thermometer periodically. After 24 h and 48 h had elapsed an analytical aliquot was removed. The reaction was halted after 48 h.

$^1$H NMR monitoring of KR for reaction A and reaction B showed that at 24 h R×n A has a 38% conversion yield while R×n B is 45% converted. Both reactions near 49% conversion at the endpoint. The greater reaction velocity of B is likely due to the excess of acyl donor and can be explained by a Le Chatlier principle argument. More intriguing is that the ee(S) at 24 h is 63% for A and 75% for B. After completion however, the ee(S) for A is higher at 87% while that of B is 83.5%.

The following equation for E enables facile measurement and is routinely employed. E is given in terms of reaction conversion (c) and enantiomeric excess of either substrate (ee(S)) or product (ee(P)):

$$E = \frac{\ln[(1-c)(1-ee(S))]}{\ln[(1-c)(1+ee(S))]} \quad (1)$$

$$E = \frac{\ln[1-c(1+ee(P))]}{\ln[1-c(1-ee(P))]} \quad (2)$$

Equations (1) and (2) can be used interchangeably to quantify E dependent on the experimental ease of measuring the enantiomeric excess of either the substrate or product. Enantiomeric excess is given in general terms by, $$ee = \frac{A-B}{A+B} \quad (3)$$

Where A and B are two enantiomers in a non-racemic mixture of a compound enriched in enantiomer A. For example, a 90:10 ratio of A:B would give an enantiomeric excess of 80% in A. Equations (1) and (2) rely on the assumptions that the reaction is irreversible, and that the reaction is either first or pseudo-first order. These assumptions hold for many enzyme-catalyzed reactions of both biological and organic molecules. A kinetic resolution can only be successful if an enzyme is sufficiently enantioselective, or the respective rates of the product formation step are significantly different. An E value of 20 or higher is required to consider an enzyme sufficiently enantioselective for a given transformation of a chiral substrate.

From the values at the endpoint, equation (1) gives the E value for R×n A as 65 where for B it gives 44. Both of these values exceed 20 clearly indicating that the enzyme is sufficiently enantioselective toward 3-hydroxyalkanoates. Indeed, both substrate and product fractions have optical purities in excess of 90%.

From examination of the conversion values it may be supposed that A simply achieves a higher E value at the endpoint because it has a slower reaction rate; reaction B nears completion at 24 h and is thus exposed to the substrate for a longer time which would allow the slow reaction (disfavored enantiomer) to take place in sparing amounts and thereby reduce the optical purity. However, in this case it is expected that the optical purity of the product would suffer and ee(S) should improve. It is clear then that in B either reversibility or some other phenomenon is occurring to reduce the enantioselectivity of CALB. The E value can be calculated using the values at 24 h to give $E_{24}$=100 for A and =46 for B showing that the enzyme is indeed more enantioselective in A. This may arise because the large excess of acyl donor drives catalysis whereas when conversion rate is limited the discrimination between R and S is improved. A summary of reactions A & B is given in Table 4.

TABLE 4

Summary of % c, ee(S), and E for Parallel Kinetic Resolutions of C10Me Rxn

| | % Conversion | | ees(S) | | E value | |
|---|---|---|---|---|---|---|
| Time h | 24 | 48 | 24 | 48 | 24 | 48 |
| A | 39.4 | 48.7 | 62.6 | 87 | 100 | 65 |
| B | 45.4 | 48.5 | 75.4 | 83.5 | 46 | 44 |

The insights gained during the various configurations of KRs of 7 were also applied to methyl 3-hydroxytetradecanoate (C14Me, 9). The racemic compound was resolved with the following batch procedure: 10 mL of 9:1 toluene to vinyl acetate was placed in a 250 mL round bottom flask and brought to 40° C. on a heating mantle while shaking. To the warmed solvent was added 2.0 g of C14Me and 1.0 g N435 resin. The reaction vessel was capped and externally covered with aluminum sheet to ensure even heating and the reaction temperature was monitored with an alcohol thermometer periodically. After 24 h and 48 h had elapsed an analytical aliquot was removed. After 48 h an additional 2.0 g of C14Me was directly added to the flask. Analytical aliquots were again removed after 24 and 48 h and another 2.0 g of C14Me were added (total=6.0 g). The reaction was halted by filtering through filter paper (Whatman) and washing the resin several times with ethyl acetate and hexanes. Table 5 provides a summary of the percent conversion, enantiomeric excess, and E value at the endpoint for each 2.0 g batch.

TABLE 5

Batch Kinetic Resolution of C14Me

| Batch | % Conversion | ees(S) | E value |
|---|---|---|---|
| 1 | 48% | 85.2% | 68 |
| 2 | 47.6% | 74.5% | 22.5 |
| 3 | 48.9% | 45% | 4 |

As seen in Table 5, the first batch gives an E value of 68 which is slightly higher than C10Me under the same conditions. Without being bound by any theory, this slightly greater enantioselectivity of CALB toward the C14Me substrate is believed to be due to the larger aliphatic substituent which results in a greater size discrepancy between the sec-alcohol substituents and thus promotes better discrimination between enantiomers. As subsequent batches of substrate are added, however, the efficiency of the enzyme begins to fall until by the third resolution batch the E value has become too low to provide sufficiently enantiopure products. This result led to the design of iterative enzymatic resolutions where substrates already enriched in a single enantiomer (such as batch 3, Table 5) were combined with fresh N435 resin to provide products with ≥95% optical purity in large quantity. Accordingly, in some embodiments, the KR includes subjecting substrates already enriched in a single enantiomer to another KR conditions. The procedure for iterative kinetic resolution was as follows: 10 mL of 9:1 toluene to vinyl acetate was placed in a 250 mL round bottom flask and brought to 40° C. on a heating mantle while shaking. To the warmed solvent was added 2.0 g of substrate enriched in (R)-7, (R)-9, (S)-7, or (S)-9 and 1.0 g N435 resin (four independent reactions). The reaction vessel was capped and externally covered with aluminum sheet to ensure even heating and the reaction temperature was monitored with an alcohol thermometer periodically. After 24 h and 48 h had elapsed an analytical aliquot was removed. After 48 h the reaction was halted by filtering through filter paper (Whatman) and washing the resin several times with ethyl acetate and hexanes. Table 6 provides a summary of the percent conversion and enantiomeric excess for iterative enzymatic resolutions of already enantiomerically enriched substrates.

TABLE 6

Summary of Four Iterative Kinetic Resolutions

| Entry | Initial Enantiomeric Excess | % Conversion | Final Enantiomeric Excess |
|---|---|---|---|
| | C10Me | | |
| (R)-C10Me | 55% | 42% | 93% |
| (S)-C10Me | 69% | 84% | 94% |
| | C14Me | | |
| (R)-C14Me | 45% | 30% | 97% |
| (S)-C14Me | 77% | 87% | 99% |

In some embodiments, the optical purity of the tail (i.e., moiety B) used in preparation of carbohydrate-based surfactant is at least 90% ee or higher. Use of a high % ee tail allows production of carbohydrate-based surfactants having "double-tail" of high diastereomeric purity. In some embodiments, after an enzymatic resolution, substrate and product are separated via column chromatography. The recovered substrate is enriched in the (R)-enantiomer and can be directly combined with N435 and the (S)-enantiomer impurity is converted and removed. Similarly, the isolated product of a primary KR is enriched in the (S)-acetylated enantiomer and is iteratively resolved after deprotection of the acetoxy group. In this case the desired compound is the product fraction, and the substrate is left behind as impurity. The percent conversion values in Table 6 correlate to the enantiomeric excess—(R)-enriched substrates have percent conversion less than 50% because the preferred enantiomer is in the minority while the situation is reversed for (S)-enriched substrates. For the (S)-enriched substrates, the final % c matches the initial percent of (S)-enantiomer of the substrate.

Synthesis of Optically Pure Rhamnolipids

Figure 4:
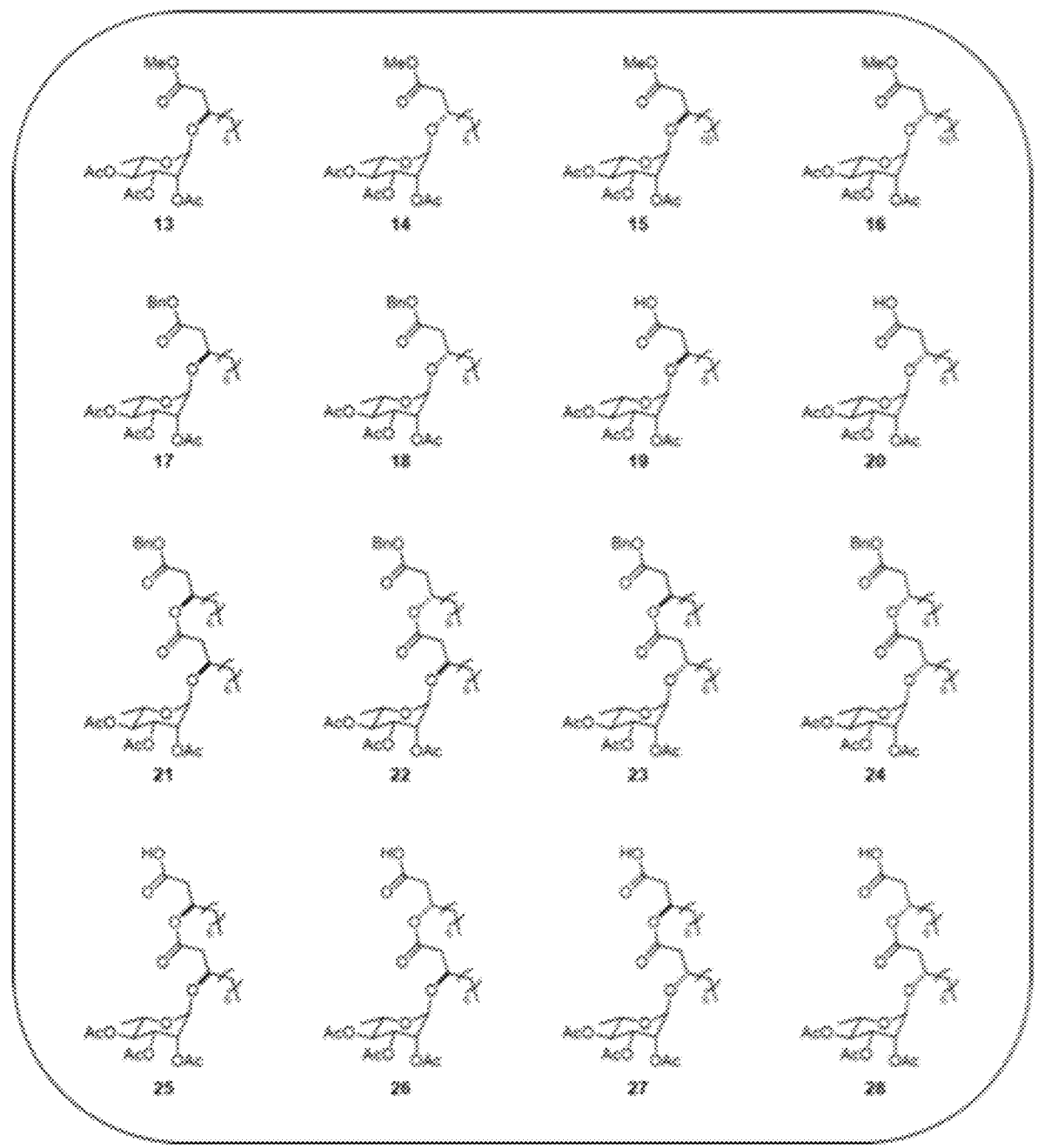
FIG. 4 shows representative protected carbohydrate-based surfactants produced using a method of the invention.

Some of the representative optically pure carbohydrate-protected rhamnolipids of the invention are shown in FIG. 4. The kinetic resolution of a methyl 3-hydroxyalkanoate provides a mixture of (R)-7/9 and (S)-11/12. After separation, the (R)-enantiomer can be directly used in subsequent steps, but the (S)-enantiomer requires a deprotection step to remove the acetoxy group and recover the sec-alcohol. Three acetoxy deprotection strategies were attempted which were CALB catalyzed deprotection, an acid catalyzed deprotection, and a base catalyzed deprotection. In the first, the native hydrolytic activity of CALB was exploited by exposing (S)-11 to N435 in aqueous media. The procedure was as follows: 10 mL of phosphate buffer solution (pH=7.4) was added to a 250 mL RBF. The flask was placed on a heating mantle while shaking and brought to 40° C. To the warmed solution was added (S)-11 (255 mg, 1.044 mmol)

and N435 (260 mg). The reaction vessel was capped and externally covered with aluminum sheet to ensure even heating and the reaction temperature was monitored with an alcohol thermometer periodically. The reaction was allowed to proceed for 24 h after which the resin was filtered and washed with ethyl acetate (EA). The aqueous phase was extracted with EA 3 times, washed with brine, and dried with $MgSO_4$. The solvent was removed under reduced pressure to give a clear oil. The crude oil was found to be a ~3:1 mixture of hydroxy:acetoxy compounds indicating that 24 h was not sufficient time to reach complete deprotection. However, it was also found that the methyl ester had been completely deprotected in both compounds to give the free acid forms. This prompted the reprotection of the free acid via Fischer esterification in acidic methanol conditions.

The crude oil was dissolved in excess methanol at reflux and a few drops of 18 M $H_2SO_4$ were added. The refluxing reaction was allowed to stir overnight and was subsequently neutralized with saturated $NaHCO_3$ and extracted. The resultant oil did indeed have its methyl ester protection back in place, but the critical discovery was that the crude compound was no longer a mixture of hydroxy/acetoxy and had been entirely converted to the hydroxy form. This finding led to the discovery that the post-resolution acetoxy products (i.e., 11 & 12) could be directly deprotected under Fischer esterification conditions (refluxing methanol with catalytic acid) to obtain their sec-alcohol (hydroxy) counterparts. This deprotection strategy is elegant in its simplicity and ease; the acyl group is removed as acetic acid while the acid methanol conditions strongly favor preservation of the methyl ester. The base catalyzed deprotection of 11 was unsuccessful and not further explored due to its tendency to give an unsaturated product via β-elimination of the alcohol.

Following from the exploratory synthetic procedures above, a direct deprotection strategy was developed as follows: (S)-11 (1.2276 g, 5.024 mmol) or (S)-12 (2.5633 g, 8.532 mmol) and 4-6 drops of 18 M $H_2SO_4$ were added to methanol (65 mL) in a 250 mL flask. The reaction vessel was attached to a condenser circulating chilled water and the mixture was brought to reflux while stirring and was allowed to proceed for 72 h. The reaction was monitored with TLC. Upon completion all but 5-10 mL of solvent were removed under reduced pressure. The concentrated reaction mixture was neutralized with saturated $NaHCO_3$ and extracted 3× with EA. The organic layer was washed with brine, dried with $MgSO_4$, and the solvent was removed under reduced pressure. (S)-7 and (S)-9 were obtained without further purification in 88% and 90% yields, respectively.

Synthesis of Single- and Dual-Tail Monorhamnolipids

Figure 5:
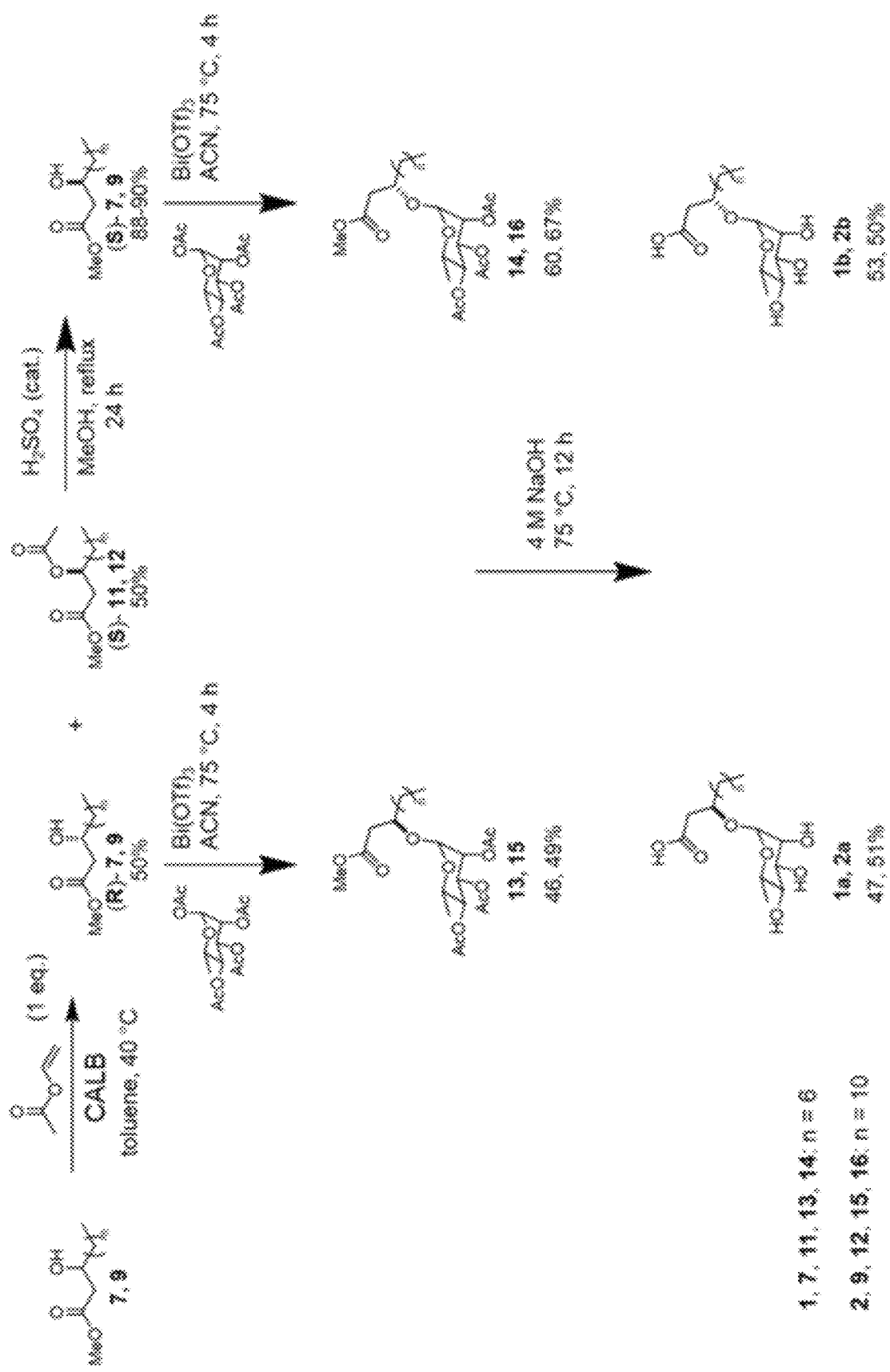
FIG. 5 illustrate a stereo-controlled synthesis of single-tail monorhamnolipids using one embodiment of the invention.

Once high optical purity methyl ester tails of both C10 and C14 were obtained, the synthesis of 1-2 (see, FIG. 5) could be achieved in 3-4 steps (3 steps for (R)- and 4 for (S)—) (FIG. 5). In particular, coupling reaction between a carbohydrate (moiety A) and the hydrophobic moiety (moiety B) can be readily achieved using the procedure disclosed in the commonly assigned U.S. Pat. No. 9,499,575, issued Nov. 22, 2016. Compounds 13-16 were isolated before deprotection, but it was found that the crude glycosylation products could be taken directly to base catalyzed deprotection eliminating one purification step and improving overall efficiency. Overall yields (beginning with enantiopure 7/9) were 22% (1a), 32% (1b), 25% (2a), and 33% (2b). It was observed in several independent syntheses that the glycosylation step provided better yields for the (S)-enantiomer for both C10 and C14, thus contributing to the slightly higher overall yields of 1b and 2b. The final deprotection step, however, did not appear to favor either diastereomer and yields of ~50% were uniform. The optical purity of final compounds 1-2 were in excess of 90%.

Figure 6:
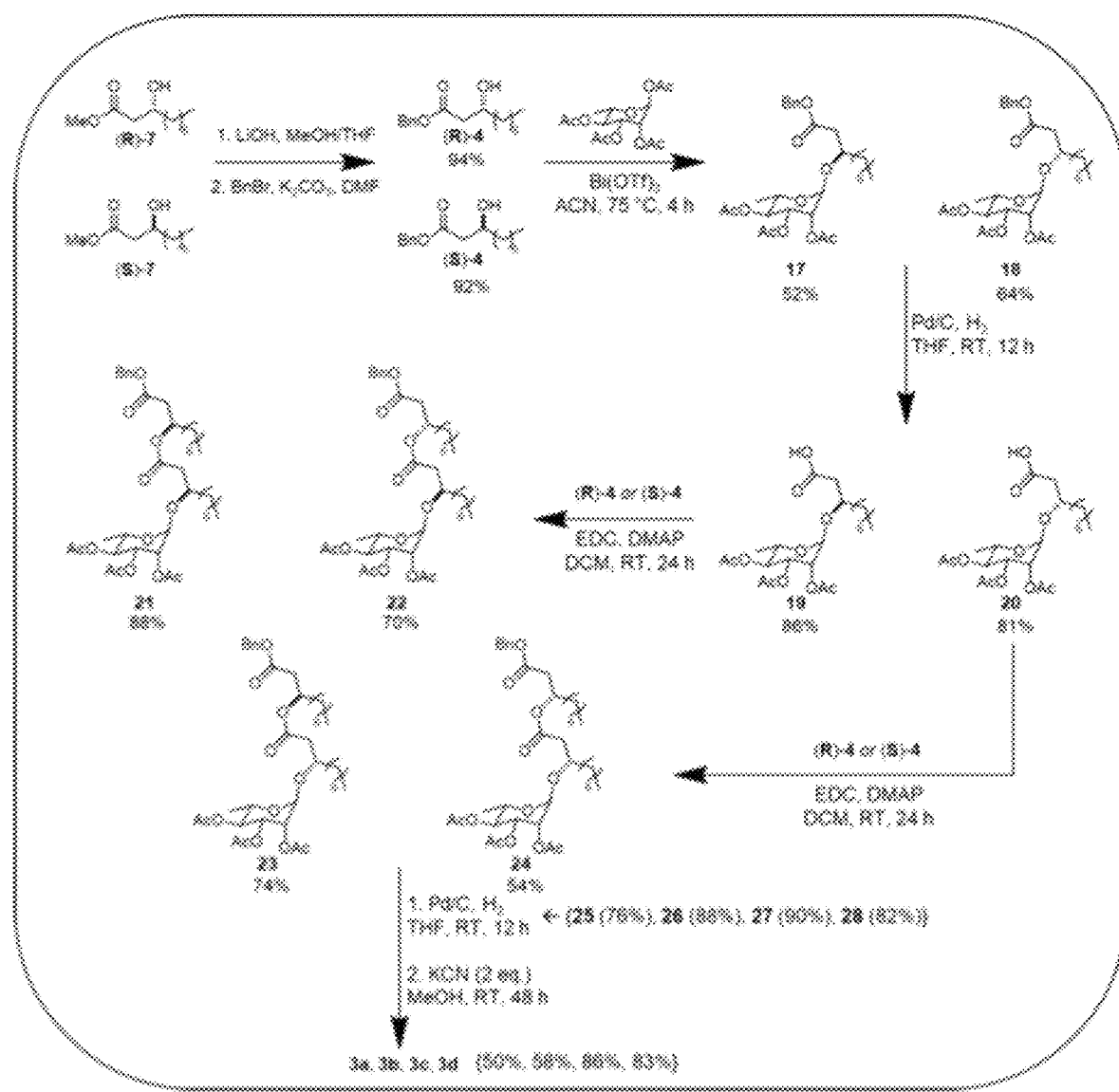
FIG. 6 illustrates stereo-controlled synthesis of dual-tail monorhamnolipids in 7 steps using one embodiment of the invention.

Dual-tail monorhamnolipids were synthesized using a procedure shown in FIG. 6. The tail coupling step proceeds via Steglich esterification and requires the rhamnoside's tail be a free acid while the sugar remains per-O-acetylated. To achieve this, the methyl ester protection was swapped for a benzyl ester protection to give an orthogonal protection to the sugar acyl groups. To give the benzyl ester, both enantiomers of 7, after enzymatic resolution, were treated with LiOH followed by BnBr in the presence of $K_2CO_3$ to conveniently arrive at enantiopure 4 in quantitative yield. Each enantiomer of 4 was then used to synthesize high optical purity diastereomers of monorhamnolipid without the tedium of chromatographic diastereomer separation. The glycosylation step with 4 gave yields of ~60% while the (R)-diastereomer gave about ~50% yield. The two debenzylation steps gave products in nearly quantitative yields.

After the first debenzylation, another equivalent of 4 (either enantiomer) is esterified at the free acid position with 1-ethyl-3-(3-dimethylaminopropyl)carbodiimide (EDC) coupling reagent in the presence of 4-dimethylaminopyridine (DMAP) catalyst. This step provided products in generally good yields ranging from 54-88%.

Figure 7:
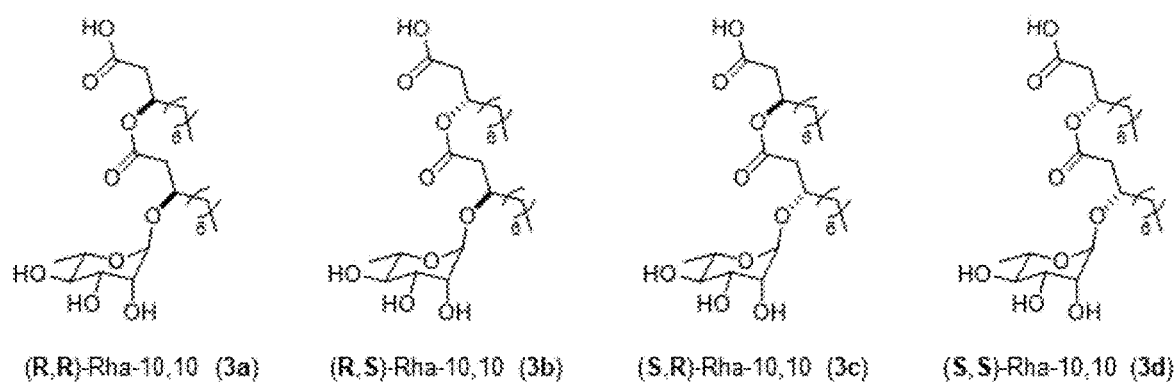
FIG. 7 shows representative double- or dual-tail carbohydrate-based surfactants of the invention.

Beginning with enantiopure 7, the final products were obtained in 7 steps and 5 chromatographic separations. The initial deprotection of the methyl ester only required a single purification after addition of the benzyl protection. Each subsequent intermediate was isolated, but the final products were given by 0-deacetylation with KCN without further purification. Compounds 25-28 were stirred with KCN (2 eq.) in methanol at RT over 48 h. The reaction was monitored by TLC and when complete the optimized procedure involved adding silica gel directly to the reaction mixture and stirring for several hours to remove excess KCN. The mixture was filtered through a silica pad and the pad was washed many times with ethyl acetate and sparing amounts of methanol to give the final products in near quantitative yield>80%). Using the procedures disclosed herein, representative examples of double- or dual-tail carbohydrates 3a, 3b, 3c and 3d were also synthesized. See, FIG. 7.

Additional objects, advantages, and novel features of this invention will become apparent to those skilled in the art upon examination of the following examples thereof, which are not intended to be limiting. In the Examples, procedures that are constructively reduced to practice are described in the present tense, and procedures that have been carried out in the laboratory are set forth in the past tense.

EXAMPLES

Peracetylated Rhamnose: L-Rhamnose (10.0 g, 55.5 mmol) and a stir bar were placed in a 250 mL round bottom flask (RBF) and the flask was placed in an ice bath to chill. Separately, acetic anhydride (31.5 mL, 333 mmol) and 0.7 M $H_2SO_4$ (4 drops) were combined and placed in an addition funnel. The acidified acetic anhydride solution was added dropwise to the L-Rhamnose with stirring. After 15 min, the flask was removed from the ice bath and submerged in a 60° C. oil bath; the reaction was allowed to proceed for 24 h. Completion was determined by TLC and the reaction was neutralized with saturated $NaHCO_3$ (150 mL) and was extracted with EA (5×35 mL). The organic fraction was washed with NaCl brine (45 mL) and the brine was back extracted with EA (lx 30 mL). The combined organic layer was dried with $MgSO_4$, filtered through Whatman filter paper (25 μm pore), and concentrated under reduced pressure to give peracetylated rhamnose as a clear, very viscous liquid; yield 62%; TLC: Rf 0.55 (50% EA:hexanes); $^1$H NMR (500 MHz, CDCl$_3$) δ 5.98 (d, J=1.9 Hz, 1H), 5.27 (dd, J=10.2, 3.5 Hz, 1H), 5.22 (dd, J=3.5, 2.0 Hz, 1H), 5.09 (t, J=10.0 Hz, 1H), 3.95-3.86 (m, 1H), 2.14 (s, 3H), 2.12 (s, 3H), 2.03 (s, 3H), 1.97 (s, 3H), 1.20 (d, J=6.3 Hz, 3H). $^{13}$C NMR (126 MHz, CDCl$_3$) δ 170.12, 169.88, 169.86, 168.43, 90.70, 70.53, 68.84, 68.78, 68.71, 20.97, 20.85, 20.82, 20.74, 17.51.

Tail Synthesis:

Benzyl 3-hydroxydecanoate (4): Zinc metal gratings (8.16 g, 125 mmol, 30-40 mesh) and dry THF (200 mL) were added to a three-necked, 250 mL RBF. A condenser circulating chilled water was attached to the central neck (the other necks were capped with rubber septa) and the mixture was brought to reflux while stirring. Octyl aldehyde (4.0 g, 31.2 mmol) and benzyl bromoacetate (14.29 g, 62.4 mmol) were added simultaneously. The violent reaction was allowed to proceed for 20-30 min at 70° C. and was brought to RT while stirring for 3-4 h. The reaction mixture was concentrated by rotary evaporation and aqueous 1 M HCl was added (150 mL) and stirred for 20 min and transferred to a separatory funnel. The reaction mixture was extracted with EA (3×25 mL). The organic fraction was washed with saturated NaCl (brine, 30 mL) and the brine was back-extracted with EA (1×20 mL). The combined organic layer was dried with MgSO$_4$, filtered through Whatman filter paper (25 μm pore), and concentrated under reduced pressure to give a crude dark-yellow/green oil. The crude product was purified by silica flash chromatography (20% EA:hexanes gradient) to give 4 as a clear oil; yield 56%; TLC: Rf 0.41 (20% EA:hexanes); $^1$H NMR (400 MHz, CDCl$_3$) δ 7.38-7.32 (m, 5H), 5.16 (s, 2H), 4.02 (s, 1H), 2.87 (s, 1H), 2.57 (dd, J=16.5, 3.2 Hz, 1H), 2.47 (dd, J=16.4, 8.9 Hz, 1H), 1.59-1.48 (m, 1H), 1.42 (td, J=13.1, 11.1, 7.0 Hz, 2H), 1.36-1.20 (m, 9H), 0.89 (t, J=7.2, 6.6 Hz, 3H). $^{13}$C NMR (101 MHz, CDCl$_3$) δ 173.00, 135.73, 128.75, 128.69, 128.56, 128.51, 128.39, 68.18, 66.61, 41.49, 36.66, 31.92, 29.60, 29.35, 25.60, 22.77, 14.22.

Benzyl (R)-3-hydroxydecanoate (R-4): R-7 (250 mg, 1.24 mmol) was placed in a 250 mL RBF and while stirring a 2.5 M solution of LiOH (2.3 mL), THF (2.5 mL), and MeOH (1.25 mL) were added. The reaction was allowed to proceed at room temperature overnight (12 h). The reaction became a white slurry which was worked up with aqueous 1 M HCl (15 mL) and extracted with EA (3×15 mL). The organic layer was washed with saturated NaCl, and the brine was back extracted with EA (1×15 mL). The combined organic layer was dried with MgSO$_4$, filtered through Whatman filter paper (25 μm pore) into a 250 mL RBF, and concentrated under reduced pressure to give a colorless, glassy solid. Dimethyl formamide (DMF, 5 mL) was added directly to the free acid and the mixture was placed on an ice bath while stirring. Once chilled K$_2$CO$_3$ (183 mg, 1.32 mmol) and BnBr (227 mg, 1.33 mmol) were added, and the stirring mixture was left overnight (12 h). The reaction was worked up by adding MilliQ water (15 mL) and extracting with diethyl ether (3×15 mL). The organic layer was washed with saturated NaCl, and the brine was back extracted with EA (1×15 mL). The combined organic layer was dried with MgSO$_4$, filtered through Whatman filter paper (25 μm pore), and concentrated under reduced pressure to give a slightly yellow oil. The crude product was purified by silica flash chromatography (20% EA:hexanes gradient) to give R-4 as a clear oil; yield 94%; TLC: Rf 0.41 (20% EA:hexanes); $^1$H NMR (500 MHz, CDCl$_3$) δ 7.33-7.16 (m, 5H), 5.04 (s, 2H), 3.90 (tt, J=7.6, 3.9 Hz, 1H), 2.73 (d, J=4.0 Hz, 1H), 2.44 (dd, J=16.5, 3.1 Hz, 1H), 2.34 (dd, J=16.5, 9.0 Hz, 1H), 1.44-1.36 (m, 1H), 1.35-1.27 (m, 2H), 1.23-1.11 (m, 9H), 0.76 (t, J=6.8 Hz, 3H). $^{13}$C NMR (126 MHz, CDCl$_3$) δ 173.01, 135.74, 128.76, 128.76, 128.51, 128.40, 128.40, 68.19, 66.62, 41.50, 36.67, 31.93, 29.61, 29.35, 25.60, 22.78, 14.23.

Benzyl (S)-3-hydroxydecanoate (S-4): S-7 (250 mg, 1.24 mmol) was placed in a 250 mL RBF and while stirring a 2.5 M solution of LiOH (2.3 mL), THF (2.5 mL), and MeOH (1.25 mL) were added. The reaction was allowed to proceed at room temperature overnight (12 h). The reaction became a yellow slurry which was worked up with aqueous 1 M HCl (15 mL) and extracted with EA (3×15 mL). The organic layer was washed with saturated NaCl, and the brine was back extracted with EA (1×15 mL). The combined organic layer was dried with MgSO$_4$, filtered through Whatman filter paper (25 μm pore) into a 250 mL RBF, and concentrated under reduced pressure to give a yellow, glassy solid. Dimethyl formamide (DMF, 5 mL) was added directly to the free acid and the mixture was placed on an ice bath while stirring. Once chilled K$_2$CO$_3$ (183 mg, 1.32 mmol) and BnBr (227 mg, 1.33 mmol) were added, and the stirring mixture was left overnight (12 h). The reaction was worked up by adding MilliQ water (15 mL) and extracting with diethyl ether (3×15 mL). The organic layer was washed with saturated NaCl, and the brine was back extracted with EA (1×15 mL). The combined organic layer was dried with MgSO$_4$, filtered through Whatman filter paper (25 μm pore), and concentrated under reduced pressure to give a slightly yellow oil. The crude product was purified by silica flash chromatography (20% EA:hexanes gradient) to give S-4 as a slightly yellow oil; yield 92%; TLC: Rf 0.41 (20% EA:hexanes); $^1$H NMR (500 MHz, CDCl$_3$) δ 7.41-7.30 (m, 5H), 5.16 (s, 2H), 4.06-3.98 (m, 1H), 2.82 (d, J=4.1 Hz, 1H), 2.56 (dd, J=16.4, 3.1 Hz, 1H), 2.46 (dd, J=16.5, 9.0 Hz, 1H), 1.54-1.47 (m, 1H), 1.47-1.37 (m, 2H), 1.27 (td, J=8.8, 8.3, 4.8 Hz, 9H), 0.88 (t, J=6.9 Hz, 3H). $^{13}$C NMR (126 MHz, CDCl$_3$) δ 173.01, 135.73, 128.76, 128.76, 128.51, 128.40, 128.40, 68.19, 66.62, 41.49, 36.67, 31.92, 29.61, 29.35, 25.60, 22.78, 14.23.

Methyl 3-hydroxyhexanoate (5): Reflux Method: Zinc metal gratings (14.51 g, 223 mmol, 30-40 mesh) and dry THF (200 mL) were added to a three-necked, 250 mL RBF. A condenser circulating chilled water was attached to the central neck (the other necks were capped with rubber septa) and the mixture was brought to reflux while stirring. Butyraldehyde (4.0 g, 55.5 mmol) and methyl bromoacetate (16.97 g, 111 mmol) were added simultaneously. The violent reaction was allowed to proceed for 20-30 min at 70° C. and was brought to RT while stirring for 3-4 h. The reaction mixture was concentrated by rotary evaporation and aqueous 1 M HCl was added (150 mL) and stirred for 20 min and transferred to a separatory funnel. The reaction mixture was extracted with EA (3×25 mL). The organic fraction was washed with saturated NaCl (brine, 30 mL) and the brine was back-extracted with EA (1×20 mL). The combined organic layer was dried with MgSO$_4$, filtered through Whatman filter paper (25 μm pore), and concentrated under reduced pressure to give a crude dark-yellow oil. The crude product was purified by silica flash chromatography (20% EA:hexanes gradient) to give 5 as a clear oil; yield 5%; TLC: Rf 0.35 (20% EA:hexanes). Sonication Method: Butyraldehyde (500 mg, 6.934 mmol), zinc metal gratings (1.814 g, 27.8 mmol, 30-40 mesh), and dry THF (5 mL) were added to a thin-walled 200 mL RBF. The flask was lowered into a sonication bath and after 20 min of sonication, methyl bromoacetate (1.273 g, 8.32 mmol) was added dropwise over 5 min and the reaction was left to sonicate 1 h. The reaction produced a cloudy, gel-like solution with a dark grey/green color. 1 M HCl was added to the mixture (15 mL) and stirred for 15 min. The reaction was extracted with EA (3×15 mL), and the organic layer was separated and washed with brine (20 mL). The brine was back extracted with EA (1×15 mL) and the combined organic layer was dried with MgSO$_4$, filtered through Whatman filter paper (25 μm pore), and concentrated under reduced pressure to give a clear oil. The crude product was purified by silica flash chromatography (20% EA:hexanes gradient) to give 5 as a clear oil; yield 42%; TLC: Rf 0.35 (20% EA:hexanes); $^1$H NMR (400 MHz, CDCl$_3$) δ 4.05-3.95 (m, 1H), 3.69 (s, 3H), 2.93 (d, J=4.0 Hz, 1H), 2.50 (dd, J=16.6, 3.3 Hz, 1H), 2.40 (dd, J=16.2, 8.9 Hz, 1H), 1.56-1.44 (m, 2H), 1.44-1.31 (m, 2H), 0.92 (t, J=7.3 Hz, 3H). $^{13}$C NMR (101 MHz, CDCl$_3$) δ 173.58, 67.85, 51.82, 41.28, 38.78, 18.78, 14.04.

Methyl 3-hydroxyoctanoate (6): Hexanal (1.0 g, 9.98 mmol), zinc metal gratings (2.611 g, 39.9 mmol, 30-40 mesh), and dry THF (7 mL) were added to a thin-walled 200 mL RBF. The flask was lowered into a sonication bath and after 20 min of sonication, methyl bromoacetate (1833 g, 11.98 mmol) was added dropwise over 5 min and the reaction was left to sonicate 1 h. The reaction produced a cloudy, gel-like solution with a dark grey/green color. 1 M HCl was added to the mixture (15 mL) and stirred for 15 min. The reaction was extracted with EA (3×15 mL), and the organic layer was separated and washed with brine (20 mL). The brine was back extracted with EA (1×15 mL) and the combined organic layer was dried with MgSO$_4$, filtered through Whatman filter paper (25 μm pore), and concentrated under reduced pressure to give a clear oil. The crude product was purified by silica flash chromatography (20% EA:hexanes gradient) to give 6 as a clear oil; yield 62%; TLC: Rf 0.38 (20% EA:hexanes); $^1$H NMR (400 MHz, CDCl$_3$) δ 4.00 (dddd, J=8.9, 7.6, 4.5, 3.3 Hz, 1H), 3.68 (s, 3H), 2.49 dd, J=16.3, 3.3 Hz, 1H), 2.39 (dd, J=16.4, 8.9 Hz, 1H), 1.75-1.15 (m, 8H), 0.91 (t, J=6.9 Hz, 3H). $^{13}$C NMR (101 MHz, CDCl$_3$) δ 173.56, 67.86, 51.81, 41.26, 38.78, 38.75, 36.24, 18.76, 14.01.

Methyl 3-hydroxydecanoate (7): Reflux Method: Zinc metal gratings (8.160 g, 125 mmol, 30-40 mesh) and dry THF (200 mL) were added to a three-necked, 250 mL RBF. A condenser circulating chilled water was attached to the central neck (the other necks were capped with rubber septa) and the mixture was brought to reflux while stirring. Octyl aldehyde (4.0 g, 31.2 mmol) and methyl bromoacetate (9.544 g, 62.4 mmol) were added simultaneously. The violent reaction was allowed to proceed for 20-30 min at 70° C. and was brought to RT while stirring for 3-4 h. The reaction mixture was concentrated by rotary evaporation and aqueous 1 M HCl was added (150 mL) and stirred for 20 min and transferred to a separatory funnel. The reaction mixture was extracted with EA (3×25 mL). The organic fraction was washed with saturated NaCl (brine, 30 mL) and the brine was back-extracted with EA (1×20 mL). The combined organic layer was dried with MgSO$_4$, filtered through Whatman filter paper (25 μm pore), and concentrated under reduced pressure to give a crude dark-green or yellow oil. The crude product was purified by silica flash chromatography (20% EA:hexanes gradient) to give 7 as a clear oil; yield 38%; TLC: Rf 0.40 (20% EA:hexanes). Sonication Method: Octyl aldehyde (1.0 g, 7.8 mmol), zinc metal gratings (2.04 g, 31.2 mmol, 30-40 mesh), and dry THF (5 mL) were added to a 20 mL scintillation vial which was placed into a sonication bath and sonicated 20 min. Methyl bromoacetate (1.432 g, 9.36 mmol) was added dropwise over 25 min and the reaction was left to sonicate an additional 1 h. An exothermic production of bubbles was observed at 20 min and the reaction produced a cloudy, gel-like solution with a dark grey/green color. 1 M HCl was added to the mixture (15 mL) and stirred for 15 min. The reaction was extracted with EA (3×15 mL), and the organic layer was separated and washed with brine (20 mL). The brine was back extracted with EA (1×15 mL) and the combined organic layer was dried with MgSO$_4$, filtered through Whatman filter paper (25 μm pore), and concentrated under reduced pressure to give a clear oil. The crude product was purified by silica flash chromatography (20% EA:hexanes gradient) to give 7 as a clear oil; yield 70%; TLC: Rf 0.40 (20% EA:hexanes); $^1$H NMR (600 MHz, CDCl$_3$) δ 4.03-3.96 (m, 1H), 3.70 (s, 3H), 2.88 (d, J=3.8 Hz, 1H), 2.50 (dd, J=16.4, 3.0 Hz, 1H), 2.40 (dd, J=16.4, 9.1 Hz, 1H), 1.57-1.47 (m, 1H), 1.45-1.39 (m, 2H), 1.33-1.22 (m, 9H), 0.87 (t, J=7.0 Hz, 3H). $^{13}$C NMR (101 MHz, CDCl$_3$) δ 173.48, 68.03, 51.71, 41.11, 36.53, 31.78, 29.46, 29.21, 25.47, 22.63, 14.06. ESI-MS (neg.): m/z: 201.25 [M-H]$^-$.

Methyl (R)-3-hydroxydecanoate (R-7): Enzymatic Resolution: 10 mL of 9:1 toluene to vinyl acetate was placed in a 250 mL round bottom flask and brought to 40° C. on a heating mantle while shaking. To the warmed solvent was added 7 (2.0 g, 9.89 mmol) and N435 resin (1.0 g). The reaction vessel was capped and externally covered with aluminum sheet to ensure even heating; the reaction temperature was monitored with an alcohol thermometer periodically. After 24 h and 48 h had elapsed an analytical aliquot was removed. The reaction was halted after 48 h and was filtered through Whatman filter paper (25 μm pore) and the resin was washed with EA (3×30 mL) and hexanes (3×30 mL). The reaction mixture was concentrated by rotary evaporation to give a slightly yellow oil. The crude product was purified by silica flash chromatography (20% EA:hexanes gradient) to give R-7 as a clear oil; yield 51%; ee=93%; E=65; TLC: Rf 0.40 (20% EA:hexanes); $^1$H NMR (400 MHz, CDCl$_3$) δ 4.09-3.96 (m, 1H), 3.73 (s, 3H), 2.96 (s, 1H), 2.54 (dd, J=16.4, 3.2 Hz, 1H), 2.43 (dd, J=16.3, 9.0 Hz, 1H), 1.59-1.50 (m, 1H), 1.45 (dq, J=6.2, 3.3, 2.6 Hz, 2H), 1.38-1.25 (m, 9H), 0.90 (t, J=6.4 Hz, 3H). $^{13}$C NMR (101 MHz, CDCl$_3$) δ 173.63, 68.17, 51.86, 41.25, 36.67, 31.93, 29.61, 29.35, 25.61, 22.77, 14.21.

Methyl (S)-3-hydroxydecanoate (S-7): (S)-11 (1.2276 g, 5.024 mmol) and 4-6 drops of 18 M H$_2$SO$_4$ were added to methanol (65 mL) in a 250 mL flask. The reaction vessel was attached to a condenser circulating chilled water and the mixture was brought to reflux while stirring and was allowed to proceed for 72 h. The reaction was monitored with TLC. Upon completion, all but 5-10 mL of solvent were removed under reduced pressure. The concentrated reaction mixture was neutralized with saturated NaHCO$_3$ and extracted with EA (3×25 mL). The organic layer was washed with brine, dried with MgSO$_4$, and the combined organic layer was concentrated by rotary evaporation. (S)-7 was obtained without further purification as a clear oil; yield 88%; ee=94%; TLC: Rf 0.40 (20% EA:hexanes); $^1$H NMR (400 MHz, CDCl$_3$) δ 4.02 (s, 1H), 3.73 (s, 3H), 2.90 (s, 1H), 2.54 (dd, J=16.4, 3.2 Hz, 1H), 2.43 (dd, J=16.4, 9.0 Hz, 1H), 1.60-1.50 (m, 1H), 1.45 (dt, J=6.2, 3.6 Hz, 2H), 1.38-1.25 (m, 9H), 0.90 (t, J=6.7 Hz, 3H). $^{13}$C NMR (101 MHz, CDCl$_3$) δ 173.63, 68.17, 51.85, 41.26, 36.68, 31.93, 29.61, 29.36, 25.62, 22.78, 14.21.

Methyl 3-hydroxydodecanoate (8): Zinc metal gratings (6.693 g, 102 mmol, 30-40 mesh) and dry THF (200 mL) were added to a three-necked, 250 mL RBF. A condenser circulating chilled water was attached to the central neck (the other necks were capped with rubber septa) and the mixture was brought to reflux while stirring. Decanal (4.0 g, 25.6 mmol) and methyl bromoacetate (7.829 g, 51.2 mmol) were added simultaneously. The violent reaction was allowed to proceed for 20-30 min at 70° C. and was brought to RT while stirring for 3-4 h. The reaction mixture was concentrated by rotary evaporation and aqueous 1 M HCl was added (150 mL) and stirred for 20 min and transferred to a separatory funnel. The reaction mixture was extracted with EA (3×25 mL). The organic fraction was washed with saturated NaCl (brine, 30 mL) and the brine was back-extracted with EA (1×20 mL). The combined organic layer was dried with MgSO$_4$, filtered through Whatman filter paper (25 μm pore), and concentrated under reduced pressure to give a crude dark-brown oil. The crude product was purified by silica flash chromatography (20% EA:hexanes gradient) to give 8 as a clear oil; yield 42%; TLC: Rf 0.41 (20% EA:hexanes); $^1$H NMR (400 MHz, CDCl$_3$) δ 4.02 (tq, J=7.4, 3.4 Hz, 1H), 3.73 (s, 3H), 2.90 (d, J=3.9 Hz, 1H), 2.53 (dd, J=16.4, 3.2 Hz, 1H), 2.43 (dd, J=16.4, 9.0 Hz, 1H), 1.60-1.50 (m, 1H), 1.50-1.42 (m, 1H), 1.37-1.24 (m, 14H), 0.90 (t, J=6.6 Hz, 3H). $^{13}$C NMR (101 MHz, CDCl$_3$) δ 173.62, 68.17, 51.85, 41.26, 36.68, 32.02, 29.70, 29.67, 29.65, 29.44, 25.62, 22.80, 14.23.

Methyl 3-hydroxytetradecanoate (9): Reflux Method: Zinc metal gratings (5.676 g, 86.8 mmol, 30-40 mesh) and dry THF (200 mL) were added to a three-necked, 250 mL RBF. A condenser circulating chilled water was attached to the central neck (the other necks were capped with rubber septa) and the mixture was brought to reflux while stirring. Dodecanal (4.0 g, 21.7 mmol) and methyl bromoacetate (3.984 g, 26.0 mmol) were added simultaneously. The violent reaction was allowed to proceed for 20-30 min at 70° C. and was brought to RT while stirring for 3-4 h. The reaction mixture was concentrated by rotary evaporation and aqueous 1 M HCl was added (150 mL) and stirred for 20 min and transferred to a separatory funnel. The reaction mixture was extracted with EA (3×25 mL). The organic fraction was washed with saturated NaCl (brine, 30 mL) and the brine was back-extracted with EA (1×20 mL). The combined organic layer was dried with MgSO$_4$, filtered through Whatman filter paper (25 μm pore), and concentrated under reduced pressure to give a crude dark-green or yellow oil. The crude product was purified by silica flash chromatography (20% EA:hexanes gradient) to give 9 as a clear oil; yield 41%; TLC: Rf 0.42 (20% EA:hexanes). Sonication Method: Dodecanal (5.3 g, 28.75 mmol), zinc metal gratings (3.76 g, 57.5 mmol, 30-40 mesh), and dry THF (10 mL) were added to a thin-walled 200 mL RBF which was placed into a sonication bath and sonicated 20 min. Methyl bromoacetate (8.8 g, 57.5 mmol) was added dropwise over 15 min and the reaction proceeded under continued sonication. Approximately 20 min after MBA addition, an exothermic production of bubbles was observed and the reaction became cloudy and gel-like, and the zinc metal was sticky and not free flowing. An additional portion of zinc (3.76 g, 57.5 mmol), which had previously been in a 350° C. furnace for 20 min, was added to the flask and the reaction was sonicated an additional 1 h. Afterwards, 1 M HCl was added to the mixture (45 mL) and stirred for 15 min. The reaction was extracted with EA (3×35 mL), and the organic layer was separated and washed with brine (40 mL). The brine was back extracted with EA (1×25 mL) and the combined organic layer was dried with MgSO$_4$, filtered through Whatman filter paper (25 μm pore), and concentrated under reduced pressure to give a clear oil. The crude product was purified by silica flash chromatography (20% EA:hexanes gradient) to give 9 as a clear oil; yield 58%; TLC: Rf 0.42 (20% EA:hexanes); $^1$H NMR (400 MHz, CDCl$_3$) δ 4.00 (td, J=8.1, 3.7 Hz, 1H), 3.71 (s, 3H), 2.89 (s, 1H), 2.52 (dd, J=16.4, 3.1 Hz, 1H), 2.41 (dd, J=16.4, 9.0 Hz, 1H), 1.59-1.48 (m, 1H), 1.46-1.39 (m, 2H), 1.36-1.22 (m, 17H), 0.88 (t, J=6.8 Hz, 3H). $^{13}$C NMR (101 MHz, CDCl$_3$) δ 173.66, 68.17, 51.87, 41.23, 36.67, 32.06, 29.79, 29.77, 29.73, 29.71, 29.66, 29.49, 25.62, 22.83, 14.26.

Methyl (R)-3-hydroxytetradecanoate (R-9): Enzymatic Resolution: 10 mL of 9:1 toluene to vinyl acetate was placed in a 250 mL round bottom flask and brought to 40° C. on a heating mantle while shaking. To the warmed solvent was added 9 (2.0 g, 7.74 mmol) and N435 resin (1.0 g). The reaction vessel was capped and externally covered with aluminum sheet to ensure even heating; the reaction temperature was monitored with an alcohol thermometer periodically. After 24 h and 48 h had elapsed an analytical aliquot was removed. The reaction was halted after 48 h and was filtered through Whatman filter paper (25 μm pore) and the resin was washed with EA (3×30 mL) and hexanes (3×30 mL). The reaction mixture was concentrated by rotary evaporation to give a slightly yellow oil. The crude product was purified by silica flash chromatography (20% EA:hexanes gradient) to give (R)-9 as a clear oil; yield 52%; ee=97%; E=68; TLC: Rf 0.42 (20% EA:hexanes); $^1$H NMR (400 MHz, CDCl$_3$) δ 4.00 (td, J=8.3, 4.3 Hz, 1H), 3.71 (s, 3H), 2.51 (dd, J=16.4, 3.2 Hz, 1H), 2.41 (dd, J=16.4, 9.0 Hz, 1H), 1.58-1.48 (m, 1H), 1.47-1.39 (m, 2H), 1.26 (d, J=7.9 Hz, 17H), 0.87 (t, J=6.7 Hz, 3H). $^{13}$C NMR (101 MHz, CDCl$_3$) δ 173.65, 68.17, 51.86, 41.23, 36.66, 32.05, 29.78, 29.76, 29.72, 29.70, 29.65, 29.48, 25.61, 22.82, 14.25.

Methyl (S)-3-hydroxytetradecanoate (S-9): (S)-12 (1.5 g, 5.0 mmol) and 4-6 drops of 18 M H$_2$SO$_4$ were added to methanol (65 mL) in a 250 mL flask. The reaction vessel was attached to a condenser circulating chilled water and the mixture was brought to reflux while stirring and was allowed to proceed for 72 h. The reaction was monitored with TLC. Upon completion, all but 5-10 mL of solvent were removed under reduced pressure. The concentrated reaction mixture was neutralized with saturated NaHCO$_3$ and extracted with EA (3×25 mL). The organic layer was washed with brine, dried with MgSO$_4$, and the combined organic layer was concentrated by rotary evaporation. (S)-9 was obtained without further purification as a clear oil; yield 91%; ee=98%; TLC: Rf 0.42 (20% EA:hexanes); $^1$H NMR (400 MHz, CDCl$_3$) δ 3.99 (tt, J=7.9, 3.6 Hz, 1H), 3.70 (s, 3H), 2.89 (s, 1H), 2.51 (dd, J=16.4, 3.2 Hz, 1H), 2.40 (dd, J=16.4, 9.0 Hz, 1H), 1.57-1.48 (m, 1H), 1.46-1.38 (m, 2H), 1.34-1.21 (m, 17H), 0.87 (t, J=6.8 Hz, 3H). $^{13}$C NMR (101 MHz, CDCl$_3$) δ 173.61, 68.16, 51.83, 41.26, 36.68, 32.04, 29.78, 29.75, 29.71, 29.70, 29.65, 29.47, 25.61, 22.81, 14.23.

Benzyl (S)-3-acetoxydecanoate (10): In a 250 mL RBF, 4 (1.0 g, 3.59 mmol; 0.70 g, 2.51 mmol; 0.70 g, 2.51 mmol) was dissolved in 15 mL of a dry organic solvent (acetonitrile; hexanes; toluene). Immobilized CALB resin (Novozym® 435 (N435), 1.0 g; 0.40 g; 1.0 g) and vinyl acetate (0.62 g, 7.20 mmol; 2.6 g, 26.7 mmol; 2.6 g, 26.7 mmol) were added to the flask which was then capped with a rubber septum and agitated on an orbital shaker for 48-72 h at room temperature. The reaction was monitored by TLC and NMR and the endpoint was determined when the conversion to product had ceased. The reaction was filtered through Whatman filter paper (25 μm pore) and the resin was washed with EA (3×20 mL) and hexanes (3×20 mL). The reaction mixture was concentrated by rotary evaporation to give a slightly yellow oil. The crude product was purified by silica flash chromatography (20% EA:hexanes gradient) to give 10 as a clear oil; yield 5%; 0%; 14%; TLC: Rf 0.63 (20% EA:hexanes); $^1$H NMR (400 MHz, CDCl$_3$) δ 7.45-7.31 (m, 5H), 5.25 (tt, J=7.3, 5.5 Hz, 1H), 5.14 (s, 2H), 2.70-2.56 (m, 2H), 1.98 (s, 3H), 1.68-1.56 (m, 2H), 1.29 (d, J=9.4 Hz, 10H), 0.91 (t, J=6.8 Hz, 3H). $^{13}$C NMR (101 MHz, CDCl$_3$) δ 170.52, 170.43, 135.89, 128.69, 128.52, 128.52, 128.44, 128.44, 70.71, 66.61, 39.41, 34.17, 31.88, 29.44, 29.25, 25.25, 22.76, 21.16, 14.22.

Methyl 3-acetoxydecanoate (11): Racemic Standard: Acetic anhydride (4.63 g, 45.3 mmol) and 7 (500 mg, 2.47 mmol) were added to a 20 mL scintillation vial. The vial was buried (up to the liquid level) in a sand bath at 55° C. and left to stir overnight (12 h). The reaction was neutralized with saturated NaHCO$_3$ and extracted with EA (3×15 mL). The combined organic fraction was dried with MgSO$_4$ and concentrated by rotary evaporation to give a crude slightly yellow oil. The crude product was purified by silica flash chromatography (20% EA:hexanes gradient) to give rac-11 as a clear oil; yield 58%; TLC: Rf 0.58 (20% EA:hexanes); $^1$H NMR (400 MHz, CDCl$_3$) δ 5.22 (tt, J=7.2, 5.5 Hz, 1H), 3.70 (s, 3H), 2.67-2.46 (m, 2H), 2.06 (s, 3H), 1.70-1.51 (m, 2H), 1.42-1.20 (m, 10H), 0.90 (t, J=6.9 Hz, 3H). $^{13}$C NMR (101 MHz, CDCl$_3$) δ 171.06, 170.56, 70.70, 51.89, 39.21, 34.17, 31.88, 29.44, 29.27, 25.27, 22.76, 21.24, 14.21.

Methyl (S)-3-acetoxydecanoate (S-11): Enzymatic Resolution: 10 mL of 9:1 toluene to vinyl acetate was placed in a 250 mL round bottom flask and brought to 40° C. on a heating mantle while shaking. To the warmed solvent was added 7 (2.0 g, 9.89 mmol) and N435 resin (1.0 g). The reaction vessel was capped and externally covered with aluminum sheet to ensure even heating; the reaction temperature was monitored with an alcohol thermometer periodically. After 24 h and 48 h had elapsed an analytical aliquot was removed. The reaction was halted after 48 h and was filtered through Whatman filter paper (25 μm pore) and the resin was washed with EA (3×30 mL) and hexanes (3×30 mL). The reaction mixture was concentrated by rotary evaporation to give a slightly yellow oil. The crude product was purified by silica flash chromatography (20% EA:hexanes gradient) to give S-11 as a clear oil; yield 49%; E=65; TLC: Rf 0.58 (20% EA:hexanes); $^1$H NMR (400 MHz, CDCl$_3$) δ 5.23 (tt, J=7.2, 5.6 Hz, 1H), 3.70 (s, 3H), 2.67-2.51 (m, 2H), 2.06 (s, 3H), 1.70-1.54 (m, 2H), 1.30 (d, J=8.0 Hz, 10H), 0.90 (t, J=6.8 Hz, 3H). $^{13}$C NMR (101 MHz, CDCl$_3$) δ 171.07, 170.57, 70.70, 51.90, 39.21, 34.17, 31.88, 29.44, 29.27, 25.27, 22.76, 21.24, 14.22.

Methyl (S)-3-acetoxytetradecanoate (12): Enzymatic Resolution: 10 mL of 9:1 toluene to vinyl acetate was placed in a 250 mL round bottom flask and brought to 40° C. on a heating mantle while shaking. To the warmed solvent was added 9 (2.0 g, 7.74 mmol) and N435 resin (1.0 g). The reaction vessel was capped and externally covered with aluminum sheet to ensure even heating; the reaction temperature was monitored with an alcohol thermometer periodically. After 24 h and 48 h had elapsed an analytical aliquot was removed. The reaction was halted after 48 h and was filtered through Whatman filter paper (25 μm pore) and the resin was washed with EA (3×30 mL) and hexanes (3×30 mL). The reaction mixture was concentrated by rotary evaporation to give a slightly yellow oil. The crude product was purified by silica flash chromatography (20% EA:hexanes gradient) to give 12 as a clear oil; yield 48%; E=68; TLC: Rf 0.62 (20% EA:hexanes); 1H NMR (400 MHz, CDCl3) δ 5.22 (tt, J=7.2, 5.5 Hz, 1H), 3.70 (s, 3H), 2.69-2.50 (m, 2H), 2.06 (s, 3H), 1.65-1.58 (m, 2H), 1.28 (s, 18H), 0.90 (t, J=6.7 Hz, 3H).

Single-Tail Rhamnolipids:

Methyl (R)-3-O-(2,3,4-tri-O-acetyl-α-L-rhamnopyranosyl)decanoate (13): A clean and dry RBF (two-necked, 50 mL, 14/20), Liebig condenser (100 mm, 14/20), and ground glass adapter (24/40 female to 14/20 male) were placed in a 350° C. furnace for 30 min. The glassware was removed, cooled, and assembled such that the condenser was fitted to the RBF, the adapter to the condenser, and a 24/40 three-way valve to adapter. To the valve's inlet was attached a balloon filled with N$_2$ gas and the glass assembly was purged by breaching the rubber septum capping the RBF's second neck with a hypodermic needle. Each joint was sealed with Teflon tape and secured with a Keck clip. Under positive pressure of N$_2$, R-7 (1.0 g, 4.94 mmol), peracetylated rhamnose (2.46 g, 7.42 mmol), bismuth(III) trifluoromethanesulfonate (Bi(OTf)$_3$) (240 mg, 0.37 mmol), and a Teflon stir bar were quickly added to the RBF through the second neck which was immediately re-capped with a rubber septum. The assembly was subjected to three cycles of pump (0.1 torr) and purge (N$_2$) by alternatively turning the valve between N$_2$ balloon and vacuum line leading to a rotary vane pump. Light heating delivered by heat gun was applied to the RBF during the pumping phases. After a final pump of 20 min, the assembly was filled with N$_2$, and the vacuum line was disconnected. Dry acetonitrile (5 mL) was added to the reaction through the septum via syringe. The flask was secured and lowered into an oil bath at 80° C. and was allowed to react while stirring for 4 h. The reaction was periodically monitored by removing small aliquots (via syringe) and performing TLC. The reaction was quenched by added saturated NaHCO$_3$ solution (15 mL) at which point a thick, intractable precipitate crashes out. The mixture was filtered through Whatman filter paper (25 μm pore) and extracted with EA (5×25 mL). The organic layer was separated and washed with brine (40 mL). The brine was back extracted with EA (1×25 mL) and the combined organic layer was dried with MgSO$_4$, filtered through Whatman filter paper (25 μm pore), and concentrated under reduced pressure to give viscous brown liquid. The crude product was purified by silica flash chromatography (20% EA:hexanes gradient) to give 13 as a clear oil; yield 46%; TLC: Rf 0.42 (30% EA:hexanes); $^1$H NMR (500 MHz, CDCl$_3$) δ 5.24 (dd, J=10.1, 3.4 Hz, 1H), 5.13 (ddd, J=17.4, 3.5, 1.9 Hz, 1H), 5.04 (td, J=9.9, 6.0 Hz, 1H), 4.85 (dd, J=17.0, 1.8 Hz, 1H), 4.13-4.07 (m, 1H), 3.96-3.84 (m, 1H), 3.69 (s, 3H), 2.64-2.44 (m, 2H), 2.14 (s, 3H), 2.03 (s, 3H), 1.97 (s, 3H), 1.61-1.44 (m, 2H), 1.34-1.23 (m, 10H), 1.19 (d, J=6.3 Hz, 3H), 0.87 (t, J=7.0 Hz, 3H). $^{13}$C NMR (101 MHz, CDCl$_3$) δ 171.93, 170.30, 170.14, 170.07, 96.12, 75.09, 71.25, 70.43, 69.17, 66.81, 51.80, 40.11, 33.49, 31.87, 29.62, 29.24, 24.88, 22.73, 21.16, 20.94, 20.86, 17.39, 14.31.

Methyl (S)-3-O-(2,3,4-Tri-O-acetyl-α-L-rhamnopyranosyl)decanoate (14): A clean and dry RBF (two-necked, 50 mL, 14/20), Liebig condenser (100 mm, 14/20), and ground glass adapter (24/40 female to 14/20 male) were placed in a 350° C. furnace for 30 min. The glassware was removed, cooled, and assembled such that the condenser was fitted to the RBF, the adapter to the condenser, and a 24/40 three-way valve to adapter. To the valve's inlet was attached a balloon filled with N$_2$ gas and the glass assembly was purged by breaching the rubber septum capping the RBF's second neck with a hypodermic needle. Each joint was sealed with Teflon tape and secured with a Keck clip. Under positive pressure of N$_2$, S-7 (0.80 g, 3.95 mmol), peracetylated rhamnose (1.97 g, 5.93 mmol), bismuth(III) trifluoromethanesulfonate (Bi(OTf)$_3$) (190 mg, 0.30 mmol), and a Teflon stir bar were quickly added to the RBF through the second neck which was immediately re-capped with a rubber septum. The assembly was subjected to three cycles of pump (0.1 torr) and purge ($N_2$) by alternatively turning the valve between $N_2$ balloon and vacuum line leading to a rotary vane pump. Light heating delivered by heat gun was applied to the RBF during the pumping phases. After a final pump of 20 min, the assembly was filled with $N_2$, and the vacuum line was disconnected. Dry acetonitrile (4 mL) was added to the reaction through the septum via syringe. The flask was secured and lowered into an oil bath at 80° C. and was allowed to react while stirring for 4 h. The reaction was periodically monitored by removing small aliquots (via syringe) and performing TLC. The reaction was quenched by added saturated $NaHCO_3$ solution (15 mL) at which point a thick, intractable precipitate crashes out. The mixture was filtered through Whatman filter paper (25 μm pore) and extracted with EA (5×25 mL). The organic layer was separated and washed with brine (40 mL). The brine was back extracted with EA (1×25 mL) and the combined organic layer was dried with $MgSO_4$, filtered through Whatman filter paper (25 μm pore), and concentrated under reduced pressure to give viscous brown liquid. The crude product was purified by silica flash chromatography (20% EA:hexanes gradient) to give 13 as a clear oil; yield 60%; TLC: Rf 0.40 (30% EA:hexanes); $^1$H NMR (500 MHz, $CDCl_3$) δ 5.23 (dd, J=10.1, 3.4 Hz, 1H), 5.16-5.09 (m, 1H), 5.04 (t, J=9.9 Hz, 1H), 4.87 (d, J=1.8 Hz, 1H), 4.08-4.00 (m, 1H), 3.97-3.89 (m, 1H), 3.68 (s, 3H), 2.54 (dd, J=15.5, 7.5 Hz, 1H), 2.46 (dd, J=15.5, 5.1 Hz, 1H), 2.13 (s, 3H), 2.03 (s, 3H), 1.96 (s, 3H), 1.64-1.48 (m, 2H), 1.34-1.23 (m, 10H), 1.19 (d, J=6.3 Hz, 3H), 0.87 (t, J=6.7 Hz, 3H). $^{13}$C NMR (126 MHz, $CDCl_3$) δ 171.88, 170.27, 170.23, 170.17, 97.75, 76.55, 71.37, 70.44, 69.31, 66.95, 51.85, 39.46, 35.20, 31.82, 29.49, 29.19, 25.23, 22.66, 20.92, 20.80, 20.73, 17.35, 14.06.

Methyl (R)-3-O-(2,3,4-tri-O-acetyl-α-L-rhamnopyranosyl)tetradecanoate (15): A clean and dry RBF (two-necked, 50 mL, 14/20), Liebig condenser (100 mm, 14/20), and ground glass adapter (24/40 female to 14/20 male) were placed in a 350° C. furnace for 30 min. The glassware was removed, cooled, and assembled such that the condenser was fitted to the RBF, the adapter to the condenser, and a 24/40 three-way valve to adapter. To the valve's inlet was attached a balloon filled with $N_2$ gas and the glass assembly was purged by breaching the rubber septum capping the RBF's second neck with a hypodermic needle. Each joint was sealed with Teflon tape and secured with a Keck clip. Under positive pressure of $N_2$, R-9 (1.0 g, 3.87 mmol), peracetylated rhamnose (1.93 g, 5.80 mmol), bismuth(III) trifluoromethanesulfonate ($Bi(OTf)_3$) (190 mg, 0.29 mmol), and a Teflon stir bar were quickly added to the RBF through the second neck which was immediately re-capped with a rubber septum. The assembly was subjected to three cycles of pump (0.1 torr) and purge ($N_2$) by alternatively turning the valve between $N_2$ balloon and vacuum line leading to a rotary vane pump. Light heating delivered by heat gun was applied to the RBF during the pumping phases. After a final pump of 20 min, the assembly was filled with $N_2$, and the vacuum line was disconnected. Dry acetonitrile (5 mL) was added to the reaction through the septum via syringe. The flask was secured and lowered into an oil bath at 80° C. and was allowed to react while stirring for 4 h. The reaction was periodically monitored by removing small aliquots (via syringe) and performing TLC. The reaction was quenched by added saturated $NaHCO_3$ solution (15 mL) at which point a thick, intractable precipitate crashes out. The mixture was filtered through Whatman filter paper (25 μm pore) and extracted with EA (5×25 mL). The organic layer was separated and washed with brine (40 mL). The brine was back extracted with EA (1×25 mL) and the combined organic layer was dried with $MgSO_4$, filtered through Whatman filter paper (25 μm pore), and concentrated under reduced pressure to give viscous brown liquid. The crude product was purified by silica flash chromatography (20% EA:hexanes gradient) to give 13 as a clear oil; yield 49%; TLC: Rf 0.45 (30% EA:hexanes); $^1$H NMR (500 MHz, $CDCl_3$) δ 5.20 (dd, J=10.1, 3.4 Hz, 1H), 5.11 (dd, J=3.5, 1.8 Hz, 1H), 5.00 (t, J=10.0 Hz, 1H), 4.80 (d, J=1.8 Hz, 1H), 4.07 (ddt, J=10.4, 8.1, 5.1 Hz, 1H), 3.86 (dq, J=9.7, 6.2 Hz, 1H), 3.66 (s, 3H), 2.54 (dd, J=15.3, 8.1 Hz, 1H), 2.45 (dd, J=15.4, 4.5 Hz, 1H), 2.10 (s, 3H), 2.00 (s, 3H), 1.94 (s, 3H), 1.55 (ddt, J=14.8, 10.0, 5.9 Hz, 1H), 1.45 (ddd, J=14.7, 9.1, 6.1 Hz, 1H), 1.28-1.19 (m, 18H), 1.15 (d, J=6.3 Hz, 3H), 0.84 (t, J=6.9 Hz, 3H). $^{13}$C NMR (126 MHz, $CDCl_3$) δ 171.85, 170.21, 170.06, 169.99, 96.05, 75.01, 71.19, 70.39, 69.12, 66.75, 51.72, 40.05, 33.44, 31.96, 29.67, 29.66, 29.61, 29.61, 29.53, 29.39, 24.84, 22.74, 21.00, 20.86, 20.78, 17.33, 14.17.

Methyl (S)-3-O-(2,3,4-tri-O-acetyl-α-L-rhamnopyranosyl)tetradecanoate (16): A clean and dry RBF (two-necked, 50 mL, 14/20), Liebig condenser (100 mm, 14/20), and ground glass adapter (24/40 female to 14/20 male) were placed in a 350° C. furnace for 30 min. The glassware was removed, cooled, and assembled such that the condenser was fitted to the RBF, the adapter to the condenser, and a 24/40 three-way valve to adapter. To the valve's inlet was attached a balloon filled with $N_2$ gas and the glass assembly was purged by breaching the rubber septum capping the RBF's second neck with a hypodermic needle. Each joint was sealed with Teflon tape and secured with a Keck clip. Under positive pressure of $N_2$, S-9 (1.5 g, 5.80 mmol), peracetylated rhamnose (2.89 g, 8.71 mmol), bismuth(III) trifluoromethanesulfonate ($Bi(OTf)_3$) (290 mg, 0.435 mmol), and a Teflon stir bar were quickly added to the RBF through the second neck which was immediately re-capped with a rubber septum. The assembly was subjected to three cycles of pump (0.1 torr) and purge ($N_2$) by alternatively turning the valve between $N_2$ balloon and vacuum line leading to a rotary vane pump. Light heating delivered by heat gun was applied to the RBF during the pumping phases. After a final pump of 20 min, the assembly was filled with $N_2$, and the vacuum line was disconnected. Dry acetonitrile (7.5 mL) was added to the reaction through the septum via syringe. The flask was secured and lowered into an oil bath at 80° C. and was allowed to react while stirring for 4 h. The reaction was periodically monitored by removing small aliquots (via syringe) and performing TLC. The reaction was quenched by added saturated $NaHCO_3$ solution (15 mL) at which point a thick, intractable precipitate crashes out. The mixture was filtered through Whatman filter paper (25 μm pore) and extracted with EA (5×25 mL). The organic layer was separated and washed with brine (40 mL). The brine was back extracted with EA (1×25 mL) and the combined organic layer was dried with $MgSO_4$, filtered through Whatman filter paper (25 μm pore), and concentrated under reduced pressure to give viscous brown liquid. The crude product was purified by silica flash chromatography (20% EA:hexanes gradient) to give 13 as a clear oil; yield 67%; TLC: Rf 0.43 (30% EA:hexanes); $^1$H NMR (500 MHz, $CDCl_3$) δ 5.24 (dd, J=10.1, 3.4 Hz, 1H), 5.12 (dd, J=3.4, 1.8 Hz, 1H), 5.05 (t, J=9.9 Hz, 1H), 4.88 (d, J=1.8 Hz, 1H), 4.05 (dq, J=7.5, 6.0 Hz, 1H), 3.94 (dq, J=9.8, 6.3 Hz, 1H), 3.69 (s, 3H), 2.58-2.52 (m, 1H), 2.47 (dd, J=15.5, 5.1 Hz, 1H), 2.14 (s, 3H), 2.04 (s, 3H), 1.98 (s, 3H), 1.67-1.58 (m, 1H), 1.55-1.49 (m, 1H), 1.35-1.23 (m, 18H), 1.20 (d, J=6.3 Hz, 3H), 0.88 (t, J=6.9 Hz, 3H). $^{13}$C NMR (126 MHz, CDCl$_3$) δ 171.91, 170.29, 170.26, 170.19, 97.80, 76.61, 71.42, 70.48, 69.35, 66.98, 51.88, 39.51, 35.24, 31.99, 29.73, 29.70, 29.66, 29.58, 29.40, 25.29, 22.74, 20.95, 20.83, 20.75, 17.38, 14.12.

(R)-3-O-(α-L-rhamnopyranosyl)decanoic acid (1a): 13 (1.0 g, 2.99 mmol) and 4 M NaOH (10 mL) were placed in a 50 mL RBF. The RBF was lowered into a 75° C. oil bath and the mixture was stirred at the stir plate's maximum setting. A high stir speed was critical for the success of the reaction; at sufficient stir speeds, the reaction began to foam. The reaction was left 12-24 h and care was taken to ensure the oil bath temperature did not exceed 80° C. The reaction was monitored by TLC and upon completion was acidified (pH≤3) with 1 M HCl and then extracted with EA (4×15 mL). The organic layer was separated and washed with brine (20 mL). The brine was back extracted with EA (1×15 mL) and the combined organic layer was dried with MgSO$_4$, filtered through Whatman filter paper (25 μm pore), and concentrated under reduced pressure to give viscous brown liquid. The crude product was purified by silica flash chromatography (20% MeOH:DCM, 0.1% AcOH gradient) and after coevaporation with toluene (3×20 mL) and DCM (3×20 mL) 1a was obtained as white crystalline solid; yield 47%; TLC: Rf 0.35-0.45 (20% MeOH:DCM, 0.1% AcOH); $^1$H NMR (500 MHz, MeOD) δ 4.80 (d, J=1.6 Hz, 1H), 4.08 (dq, J=7.6, 5.6 Hz, 1H), 3.76 (dd, J=3.4, 1.8 Hz, 1H), 3.66 (dq, J=9.4, 6.2 Hz, 1H), 3.61 (dd, J=9.5, 3.4 Hz, 1H), 3.36 (t, J=9.5 Hz, 1H), 2.59-2.40 (m, 2H), 1.63-1.51 (m, 2H), 1.39-1.28 (m, 10H), 1.24 (d, J=6.2 Hz, 3H), 0.91 (t, J=6.7 Hz, 3H). $^{13}$C NMR (126 MHz, MeOD) δ 175.27, 100.45, 75.66, 73.89, 72.69, 72.35, 70.22, 41.26, 34.53, 32.98, 30.71, 30.35, 25.91, 23.71, 17.86, 14.42.

(S)-3-O-(α-L-rhamnopyranosyl)decanoic acid (1b): 14 (1.0 g, 2.99 mmol) and 4 M NaOH (10 mL) were placed in a 50 mL RBF. The RBF was lowered into a 75° C. oil bath and the mixture was stirred at the stir plate's maximum setting. A high stir speed was critical for the success of the reaction; at sufficient stir speeds, the reaction began to foam. The reaction was left 12-24 h and care was taken to ensure the oil bath temperature did not exceed 80° C. The reaction was monitored by TLC and upon completion was acidified (pH≤3) with 1 M HCl and then extracted with EA (4×15 mL). The organic layer was separated and washed with brine (20 mL). The brine was back extracted with EA (1×15 mL) and the combined organic layer was dried with MgSO$_4$, filtered through Whatman filter paper (25 μm pore), and concentrated under reduced pressure to give viscous brown liquid. The crude product was purified by silica flash chromatography (20% MeOH:DCM, 0.1% AcOH gradient) and after coevaporation with toluene (3×20 mL) and DCM (3×20 mL) 1b was obtained as a white crystalline solid; yield 53%; TLC: Rf 0.10-0.40 (20% MeOH:DCM, 0.1% AcOH); $^1$H NMR (500 MHz, CDCl$_3$) δ 4.85 (s, 1H), 4.03 (p, J=6.3 Hz, 1H), 3.78-3.72 (m, 1H), 3.70-3.63 (m, 1H), 3.60 (dd, J=9.5, 3.2 Hz, 1H), 3.34 (t, J=9.5 Hz, 1H), 2.40 (dd, J=14.2, 7.2 Hz, 1H), 2.25 (dd, J=14.3, 5.7 Hz, 1H), 1.54 (q, J=7.1 Hz, 2H), 1.42-1.23 (m, 10H), 1.21 (d, J=6.3 Hz, 3H), 0.87 (t, J=6.7 Hz, 3H). $^{13}$C NMR (126 MHz, CDCl$_3$) δ 180.22, 101.28, 77.57, 73.99, 72.78, 72.39, 70.10, 43.99, 36.70, 33.01, 30.74, 30.38, 26.52, 23.67, 17.90, 14.37.

(R)-3-O-(α-L-rhamnopyranosyl)tetradecanoic acid (2a): 15 (1.0 g, 2.56 mmol) and 4 M NaOH (10 mL) were placed in a 50 mL RBF. The RBF was lowered into a 75° C. oil bath and the mixture was stirred at the stir plate's maximum setting. A high stir speed was critical for the success of the reaction; at sufficient stir speeds, the reaction began to foam. The reaction was left 12-24 h and care was taken to ensure the oil bath temperature did not exceed 80° C. The reaction was monitored by TLC and upon completion was acidified (pH≤3) with 1 M HCl and then extracted with EA (4×15 mL). The organic layer was separated and washed with brine (20 mL). The brine was back extracted with EA (1×15 mL) and the combined organic layer was dried with MgSO$_4$, filtered through Whatman filter paper (25 μm pore), and concentrated under reduced pressure to give viscous brown liquid. The crude product was purified by silica flash chromatography (20% MeOH:DCM, 0.1% AcOH gradient) and after coevaporation with toluene (3×20 mL) and DCM (3×20 mL) 2a was obtained as a white crystalline solid; yield 51%; TLC: Rf 0.37-0.58 (20% MeOH:DCM, 0.1% AcOH); $^1$H NMR (500 MHz, MeOD) δ 4.79 (d, J=1.6 Hz, 1H), 4.12-4.04 (m, 1H), 3.79-3.72 (m, 1H), 3.66 (dq, J=9.4, 6.2 Hz, 1H), 3.61 (dd, J=9.5, 3.4 Hz, 1H), 3.36 (t, J=9.5 Hz, 1H), 2.58-2.42 (m, 2H), 1.63-1.49 (m, 2H), 1.37-1.26 (m, 18H), 1.24 (d, J=6.1 Hz, 3H), 0.90 (t, J=6.8 Hz, 3H). $^{13}$C NMR (126 MHz, MeOD) δ 175.26, 100.40, 75.62, 73.88, 72.68, 72.34, 70.20, 41.26, 34.52, 33.07, 30.78, 30.75, 30.75, 30.73, 30.68, 30.48, 25.92, 23.73, 17.86, 14.45.

(S)-3-O-(α-L-rhamnopyranosyl)tetradecanoic acid (2b): 16 (1.0 g, 2.56 mmol) and 4 M NaOH (10 mL) were placed in a 50 mL RBF. The RBF was lowered into a 75° C. oil bath and the mixture was stirred at the stir plate's maximum setting. A high stir speed was critical for the success of the reaction; at sufficient stir speeds, the reaction began to foam. The reaction was left 12-24 h and care was taken to ensure the oil bath temperature did not exceed 80° C. The reaction was monitored by TLC and upon completion was acidified (pH≤3) with 1 M HCl and then extracted with EA (4×15 mL). The organic layer was separated and washed with brine (20 mL). The brine was back extracted with EA (1×15 mL) and the combined organic layer was dried with MgSO$_4$, filtered through Whatman filter paper (25 μm pore), and concentrated under reduced pressure to give viscous brown liquid. The crude product was purified by silica flash chromatography (20% MeOH:DCM, 0.1% AcOH gradient) and after coevaporation with toluene (3×20 mL) and DCM (3×20 mL) 2b was obtained a white crystalline solid; yield 50%; TLC: Rf 0.10-0.44 (20% MeOH:DCM, 0.1% AcOH); $^1$H NMR (500 MHz, MeOD) δ 4.85 (d, J=1.6 Hz, 1H), 4.03 (p, J=6.1 Hz, 1H), 3.75 (dd, J=3.4, 1.6 Hz, 1H), 3.66 (dq, J=9.7, 6.3 Hz, 1H), 3.60 (dd, J=9.5, 3.3 Hz, 1H), 3.34 (t, J=9.5 Hz, 1H), 2.41 (dd, J=14.4, 7.3 Hz, 1H), 2.28 (dd, J=14.4, 5.7 Hz, 1H), 1.55 (dtd, J=8.4, 5.8, 2.3 Hz, 2H), 1.27 (d, J=7.2 Hz, 18H), 1.22 (d, J=6.3 Hz, 3H), 0.87 (t, J=6.9 Hz, 3H). $^{13}$C NMR (126 MHz, MeOD) δ 179.07, 101.32, 77.39, 73.91, 72.70, 72.34, 70.09, 43.32, 36.65, 33.06, 30.80, 30.78, 30.74, 30.74, 30.47, 26.51, 23.72, 17.97, 17.94, 14.46.

Dual-Tail Rhamnolipids:

Benzyl (R)-3-O-(2,3,4-tri-O-acetyl-α-L-rhamnopyranosyl)decanoate (17): A clean and dry RBF (two-necked, 50 mL, 14/20), Liebig condenser (100 mm, 14/20), and ground glass adapter (24/40 female to 14/20 male) were placed in a 350° C. furnace for 30 min. The glassware was removed, cooled, and assembled such that the condenser was fitted to the RBF, the adapter to the condenser, and a 24/40 three-way valve to adapter. To the valve's inlet was attached a balloon filled with N$_2$ gas and the glass assembly was purged by breaching the rubber septum capping the RBF's second neck with a hypodermic needle. Each joint was sealed with Teflon tape and secured with a Keck clip. Under positive pressure of N$_2$, R-4 (0.72 g, 2.59 mmol), peracetylated rhamnose (1.29 g, 3.88 mmol), bismuth(III) trifluoromethanesulfonate (Bi(OTf)$_3$) (127 mg, 0.19 mmol), and a Teflon stir bar were quickly added to the RBF through the second neck which was immediately re-capped with a rubber septum. The assembly was subjected to three cycles of pump (0.1 torr) and purge (N$_2$) by alternatively turning the valve between N$_2$ balloon and vacuum line leading to a rotary vane pump. Light heating delivered by heat gun was applied to the RBF during the pumping phases. After a final pump of 20 min, the assembly was filled with N$_2$, and the vacuum line was disconnected. Dry acetonitrile (5 mL) was added to the reaction through the septum via syringe. The flask was secured and lowered into an oil bath at 80° C. and was allowed to react while stirring for 4 h. The reaction was periodically monitored by removing small aliquots (via syringe) and performing TLC. The reaction was quenched by added saturated NaHCO$_3$ solution (15 mL) at which point a thick, intractable precipitate crashes out. The mixture was filtered through Whatman filter paper (25 μm pore) and extracted with EA (5×25 mL). The organic layer was separated and washed with brine (40 mL). The brine was back extracted with EA (1×25 mL) and the combined organic layer was dried with MgSO$_4$, filtered through Whatman filter paper (25 μm pore), and concentrated under reduced pressure to give viscous brown liquid. The crude product was purified by silica flash chromatography (20% EA:hexanes gradient) to give 17 as a clear oil; yield 52%; TLC: Rf 0.52 (30% EA:hexanes); $^1$H NMR (500 MHz, MeOD) δ 7.41-7.28 (m, 5H), 5.19-5.16 (m, 1H), 5.14 (ddd, J=8.4, 4.2, 2.5 Hz, 3H), 4.98 (t, J=9.9 Hz, 1H), 4.89 (d, J=1.7 Hz, 1H), 4.14 (p, J=6.0 Hz, 1H), 3.97-3.88 (m, 1H), 2.68-2.56 (m, 2H), 2.12 (s, 3H), 2.02 (s, 3H), 1.96 (s, 3H), 1.66-1.57 (m, 1H), 1.58-1.49 (m, 1H), 1.36-1.27 (m, 10H), 1.11 (d, J=6.2 Hz, 3H), 0.90 (t, J=6.8 Hz, 3H). $^{13}$C NMR (126 MHz, MeOD) δ 173.00, 171.87, 171.85, 171.73, 137.52, 129.72, 129.72, 129.44, 129.44, 129.37, 97.43, 76.39, 72.15, 71.50, 70.68, 68.05, 67.52, 41.05, 34.19, 32.88, 30.53, 30.22, 25.73, 23.64, 20.67, 20.63, 20.56, 17.60, 14.38.

Benzyl (S)-3-O-(2,3,4-tri-O-acetyl-α-L-rhamnopyranosyl)decanoate (18): A clean and dry RBF (two-necked, 50 mL, 14/20), Liebig condenser (100 mm, 14/20), and ground glass adapter (24/40 female to 14/20 male) were placed in a 350° C. furnace for 30 min. The glassware was removed, cooled, and assembled such that the condenser was fitted to the RBF, the adapter to the condenser, and a 24/40 three-way valve to adapter. To the valve's inlet was attached a balloon filled with N$_2$ gas and the glass assembly was purged by breaching the rubber septum capping the RBF's second neck with a hypodermic needle. Each joint was sealed with Teflon tape and secured with a Keck clip. Under positive pressure of N$_2$, S-4 (1.03 g, 3.70 mmol), peracetylated rhamnose (1.84 g, 5.54 mmol), bismuth(III) trifluoromethanesulfonate (Bi(OTf)$_3$) (182 mg, 0.28 mmol), and a Teflon stir bar were quickly added to the RBF through the second neck which was immediately re-capped with a rubber septum. The assembly was subjected to three cycles of pump (0.1 torr) and purge (N$_2$) by alternatively turning the valve between N$_2$ balloon and vacuum line leading to a rotary vane pump. Light heating delivered by heat gun was applied to the RBF during the pumping phases. After a final pump of 20 min, the assembly was filled with N$_2$, and the vacuum line was disconnected. Dry acetonitrile (5 mL) was added to the reaction through the septum via syringe. The flask was secured and lowered into an oil bath at 80° C. and was allowed to react while stirring for 4 h. The reaction was periodically monitored by removing small aliquots (via syringe) and performing TLC. The reaction was quenched by added saturated NaHCO$_3$ solution (15 mL) at which point a thick, intractable precipitate crashes out. The mixture was filtered through Whatman filter paper (25 μm pore) and extracted with EA (5×25 mL). The organic layer was separated and washed with brine (40 mL). The brine was back extracted with EA (1×25 mL) and the combined organic layer was dried with MgSO$_4$, filtered through Whatman filter paper (25 μm pore), and concentrated under reduced pressure to give viscous brown liquid. The crude product was purified by silica flash chromatography (20% EA:hexanes gradient) to give 18 as a clear oil; yield 64%; TLC: Rf 0.52 (30% EA:hexanes); $^1$H NMR (500 MHz, CDCl$_3$) δ 7.42-7.32 (m, 5H), 5.28 (dd, J=10.1, 3.5 Hz, 1H), 5.19-5.14 (m, 3H), 5.08 (t, J=9.9 Hz, 1H), 4.92 (d, J=1.8 Hz, 1H), 4.13-4.07 (m, 1H), 4.02-3.89 (m, 1H), 2.63 (dd, J=15.6, 7.3 Hz, 1H), 2.53 (dd, J=15.7, 5.3 Hz, 1H), 2.16 (s, 3H), 2.07 (s, 3H), 2.00 (s, 3H), 1.68-1.60 (m, 1H), 1.60-1.51 (m, 1H), 1.38-1.24 (m, 10H), 1.22 (d, J=6.3 Hz, 3H), 0.90 (t, J=6.9 Hz, 3H). $^{13}$C NMR (126 MHz, CDCl$_3$) δ 174.33, 171.27, 170.29, 170.21, 136.01, 128.76, 128.76, 128.63, 128.63, 128.46, 97.65, 76.29, 71.28, 70.35, 69.25, 66.88, 66.67, 39.55, 35.11, 31.82, 29.48, 29.19, 25.19, 22.67, 20.99, 20.86, 20.79, 17.34, 14.11.

(R)-3-O-(2,3,4-tri-O-acetyl-α-L-rhamnopyranosyl)decanoic acid (19): A clean and dry RBF (two-necked, 50 mL, 14/20) and ground glass adapter (24/40 female to 14/20 male) were placed in a 350° C. furnace for 30 min. The glassware was removed, cooled, and assembled such that the adapter was attached to the RBF's central neck and a 24/40 three-way valve was attached to adapter. To the valve's inlet was attached a balloon filled with Ar gas and the glass assembly was purged by breaching the rubber septum capping the RBF's second neck with a hypodermic needle. Each joint was sealed with Teflon tape and secured with a Keck clip. Under positive pressure of Ar, 17 (710 mg, 1.29 mmol), Pd/C (71 mg, 10% Pd), 5 mL of dry THF, and a Teflon stir bar were quickly added to the RBF through the second neck which was immediately re-capped with a rubber septum. The assembly was closed, the balloon was filled with H$_2$ gas, and the assembly was purged once with H$_2$ and then kept under 1 atm of H$_2$. The reaction was allowed to proceed 12-24 h at RT and was periodically monitored by removing small aliquots (via syringe) and performing TLC. The reaction was quenched by filtering through a 12 mm Celite pad under light vacuum (25 torr) and the pad was washed with DCM (3×15 mL) and EA (3×15 mL). The combined organic layer was dried with MgSO$_4$, filtered through Whatman filter paper (25 μm pore), and concentrated under reduced pressure to give a clear oil. The crude product was purified by silica flash chromatography (20% MeOH:DCM, 0.1% AcOH gradient) and after coevaporation with toluene (3×20 mL) and DCM (3×20 mL) 19 was obtained as a clear oil; yield 86%; TLC: Rf 0.70 (20% MeOH:DCM, 0.1% AcOH); $^1$H NMR (500 MHz, CDCl$_3$) δ 5.26 (dd, J=10.1, 3.5 Hz, 1H), 5.17 (dd, J=3.4, 1.8 Hz, 1H), 5.05 (t, J=9.9 Hz, 1H), 4.85 (d, J=1.8 Hz, 1H), 4.09 (dq, J=7.6, 5.8 Hz, 1H), 3.96 (dq, J=9.7, 6.2 Hz, 1H), 2.65 (dd, J=15.9, 7.6 Hz, 1H), 2.54 (dd, J=15.9, 4.8 Hz, 1H), 2.15 (s, 3H), 2.05 (s, 3H), 1.99 (s, 3H), 1.62-1.49 (m, 2H), 1.37-1.22 (m, 10H), 1.19 (d, J=6.3 Hz, 3H), 0.88 (t, J=7.0 Hz, 3H). $^{13}$C NMR (126 MHz, CDCl$_3$) δ 176.09, 170.34, 170.18, 170.12, 96.60, 75.27, 71.24, 70.44, 69.20, 66.92, 39.91, 33.74, 31.88, 29.61, 29.25, 24.94, 22.74, 21.17, 20.94, 20.87, 17.32, 14.32.

(S)-3-O-(2,3,4-tri-O-acetyl-α-L-rhamnopyranosyl)decanoic acid (20): A clean and dry RBF (two-necked, 50 mL, 14/20) and ground glass adapter (24/40 female to 14/20 male) were placed in a 350° C. furnace for 30 min. The glassware was removed, cooled, and assembled such that the adapter was attached to the RBF's central neck and a 24/40 three-way valve was attached to adapter. To the valve's inlet was attached a balloon filled with Ar gas and the glass assembly was purged by breaching the rubber septum capping the RBF's second neck with a hypodermic needle. Each joint was sealed with Teflon tape and secured with a Keck clip. Under positive pressure of Ar, 18 (946 mg, 1.72 mmol), Pd/C (95 mg, 10% Pd), 5 mL of dry THF, and a Teflon stir bar were quickly added to the RBF through the second neck which was immediately re-capped with a rubber septum. The assembly was closed, the balloon was filled with $H_2$ gas, and the assembly was purged once with $H_2$ and then kept under 1 atm of $H_2$. The reaction was allowed to proceed 12-24 h at RT and was periodically monitored by removing small aliquots (via syringe) and performing TLC. The reaction was quenched by filtering through a 12 mm Celite pad under light vacuum (25 torr) and the pad was washed with DCM (3×15 mL) and EA (3×15 mL). The combined organic layer was dried with $MgSO_4$, filtered through Whatman filter paper (25 μm pore), and concentrated under reduced pressure to give a clear oil. The crude product was purified by silica flash chromatography (20% MeOH:DCM, 0.1% AcOH gradient) and after coevaporation with toluene (3×20 mL) and DCM (3×20 mL) 20 was obtained as a clear oil; yield 81%; TLC: Rf 0.70 (20% MeOH:DCM, 0.1% AcOH); $^1$H NMR (500 MHz, $CDCl_3$) δ 5.24 (dd, J=10.1, 3.4 Hz, 1H), 5.13 (dd, J=3.5, 1.8 Hz, 1H), 5.04 (t, J=9.9 Hz, 1H), 4.89 (d, J=1.8 Hz, 1H), 4.04 (dq, J=7.4, 5.8 Hz, 1H), 3.93 (dq, J=10.2, 6.3 Hz, 1H), 2.58 (dd, J=15.9, 7.5 Hz, 1H), 2.50 (dd, J=15.8, 5.2 Hz, 1H), 2.12 (s, 3H), 2.03 (s, 3H), 1.96 (s, 3H), 1.67-1.49 (m, 2H), 1.36-1.24 (m, 10H), 1.19 (d, J=6.3 Hz, 3H), 0.87 (t, J=6.9 Hz, 3H). $^{13}$C NMR (126 MHz, $CDCl_3$) δ 175.97, 170.26, 170.18, 170.16, 97.58, 76.22, 71.31, 70.45, 69.26, 66.97, 39.36, 35.18, 31.88, 29.54, 29.26, 25.27, 22.74, 21.03, 20.91, 20.83, 17.42, 14.18.

Benzyl (R)-3-O—[(R)-(3'-O-decyl)2,3,4-tri-O-acetyl-α-L-rhamnopyranosyl]decanoate (21): 19 (250 mg, 0.543 mmol) was dissolved in 11.25 mL dichloromethane (DCM) and placed in a 250 mL RBF. To the stirring mixture was added EDC (208 mg, 1.09 mmol) and DMAP (99.5 mmg, 0.814 mmol). After 10 min, R-4 (227 mg, 0.814 mmol, dissolved in 1.5 mL DCM) was added. The reaction was covered and allowed to proceed at RT while stirring for 24 h. The reaction was quenched with saturated $NaHCO_3$ (15 mL) and NaCl brine (10 mL). The mixture was extracted with DCM (3×20 mL) and the combined organic layer was dried with $MgSO_4$, filtered through Whatman filter paper (25 μm pore), and concentrated under reduced pressure to give a clear oil. The crude product was purified by silica flash chromatography (30% EA:hexanes gradient) to give 21 as a clear oil; yield 88%; TLC: Rf 0.60 (30% EA:hexanes); $^1$H NMR (500 MHz, $CDCl_3$) δ 7.37-7.32 (m, 5H), 5.26 (dd, J=10.1, 3.5 Hz, 1H), 5.17 (dd, J=3.5, 1.8 Hz, 1H), 5.14 (s, 2H), 5.12 (d, J=1.2 Hz, 1H), 5.05 (t, J=10.0 Hz, 1H), 4.84 (d, J=1.7 Hz, 1H), 4.09-3.92 (m, 2H), 2.74-2.36 (m, 4H), 2.13 (s, 3H), 1.98 (s, 3H), 1.96 (s, 3H), 1.61 (qd, J=8.4, 7.7, 5.1 Hz, 1H), 1.51 (qd, J=10.7, 9.3, 3.6 Hz, 2H), 1.42 (ddd, J=7.9, 4.9, 2.9 Hz, 2H), 1.32-1.22 (m, 19H), 1.20 (d, J=6.2 Hz, 3H), 0.88 (t, J=6.9 Hz, 6H). $^{13}$C NMR (126 MHz, $CDCl_3$) δ 172.80, 170.52, 170.17, 170.12, 170.05, 169.87, 135.69, 128.63, 128.58, 128.37, 128.33, 128.28, 96.37, 75.11, 71.20, 70.94, 70.33, 69.15, 66.72, 66.45, 40.18, 39.07, 33.86, 33.35, 31.83, 29.59, 29.52, 29.33, 29.26, 29.19, 29.16, 25.51, 25.15, 24.75, 20.96, 20.76, 20.74, 17.34, 14.13, 14.12.

Benzyl (R)-3-O—[(S)-(3'-O-decyl)2,3,4-tri-O-acetyl-α-L-rhamnopyranosyl]decanoate (22): 19 (208 mg, 0.452 mmol) was dissolved in 9 mL dichloromethane (DCM) and placed in a 250 mL RBF. To the stirring mixture was added EDC (116 mg, 0.603 mmol) and DMAP (36.8 mmg, 0.301 mmol). After 10 min, S-4 (83.9 mg, 0.301 mmol, dissolved in 1 mL DCM) was added. The reaction was covered and allowed to proceed at RT while stirring for 24 h. The reaction was quenched with saturated $NaHCO_3$ (15 mL) and NaCl brine (10 mL). The mixture was extracted with DCM (3×20 mL) and the combined organic layer was dried with $MgSO_4$, filtered through Whatman filter paper (25 μm pore), and concentrated under reduced pressure to give a clear oil. The crude product was purified by silica flash chromatography (30% EA:hexanes gradient) to give 22 as a clear oil; yield 70%; TLC: Rf 0.61 (30% EA:hexanes); $^1$H NMR (500 MHz, $CDCl_3$) δ 7.36-7.30 (m, 5H), 5.25-5.17 (m, 2H), 5.14 (dd, J=3.5, 1.8 Hz, 1H), 5.09 (d, J=1.4 Hz, 2H), 5.03 (t, J=9.9 Hz, 1H), 4.81 (d, J=1.7 Hz, 1H), 4.08-4.01 (m, 1H), 3.92 (dq, J=9.8, 6.3 Hz, 1H), 2.70-2.25 (m, 4H), 2.12 (s, 3H), 2.00 (s, 3H), 1.95 (s, 3H), 1.64-1.54 (m, 2H), 1.52-1.44 (m, 2H), 1.31-1.20 (m, 20H), 1.18 (d, J=6.2 Hz, 3H), 0.91-0.81 (m, 6H). $^{13}$C NMR (126 MHz, $CDCl_3$) δ 170.59, 170.25, 170.20, 170.03, 169.88, 135.81, 128.66, 128.60, 128.41, 128.36, 128.31, 96.20, 74.84, 71.16, 70.95, 70.35, 69.22, 68.10, 66.74, 66.50, 40.08, 39.10, 33.99, 33.28, 31.87, 31.84, 29.62, 29.39, 29.22, 29.14, 25.22, 24.78, 22.69, 22.68, 21.00, 20.84, 20.76, 17.33, 14.14.

Benzyl (S)-3-O—[(R)-(3'-O-decyl)2,3,4-tri-O-acetyl-α-L-rhamnopyranosyl]decanoate (23): 20 (410 mg, 0.890 mmol) was dissolved in 19 mL dichloromethane (DCM) and placed in a 250 mL RBF. To the stirring mixture was added EDC (341 mg, 1.78 mmol) and DMAP (163 mmg, 1.34 mmol). After 10 min, R-4 (372 mg, 1.34 mmol, dissolved in 1.5 mL DCM) was added. The reaction was covered and allowed to proceed at RT while stirring for 24 h. The reaction was quenched with saturated $NaHCO_3$ (15 mL) and NaCl brine (10 mL). The mixture was extracted with DCM (3×20 mL) and the combined organic layer was dried with $MgSO_4$, filtered through Whatman filter paper (25 μm pore), and concentrated under reduced pressure to give a clear oil. The crude product was purified by silica flash chromatography (30% EA:hexanes gradient) to give 23 as a clear oil; yield 70%; TLC: Rf 0.58 (30% EA:hexanes); $^1$H NMR (500 MHz, $CDCl_3$) δ 7.37-7.32 (m, 5H), 5.29-5.20 (m, 2H), 5.13 (dd, J=3.5, 1.8 Hz, 1H), 5.10 (d, J=1.4 Hz, 2H), 5.05 (t, J=9.9 Hz, 1H), 4.88 (d, J=1.8 Hz, 1H), 4.01 (p, J=6.1 Hz, 1H), 3.93 (dq, J=9.8, 6.2 Hz, 1H), 2.67-2.54 (m, 2H), 2.48 (dd, J=15.7, 7.0 Hz, 1H), 2.32 (dd, J=15.6, 5.7 Hz, 1H), 2.13 (s, 3H), 2.04 (d, J=1.3 Hz, 3H), 1.96 (s, 3H), 1.66-1.47 (m, 4H), 1.31-1.23 (m, 20H), 1.20 (d, J=6.3 Hz, 3H), 0.93-0.82 (m, 6H). $^{13}$C NMR (126 MHz, $CDCl_3$) δ 170.52, 170.31, 170.10, 169.98, 169.96, 135.88, 128.63, 128.63, 128.45, 128.45, 128.37, 97.33, 75.79, 71.27, 71.07, 70.29, 69.26, 66.84, 66.51, 39.41, 39.13, 35.04, 33.98, 31.89, 31.89, 29.57, 29.36, 29.29, 29.17, 25.27, 25.22, 22.75, 22.71, 21.02, 20.91, 20.81, 17.41, 14.19, 14.19.

Benzyl (S)-3-O—[(S)-(3'-O-decyl)2,3,4-tri-O-acetyl-α-L-rhamnopyranosyl]decanoate (24): 20 (392 mg, 0.851 mmol) was dissolved in 18 mL dichloromethane (DCM) and placed in a 250 mL RBF. To the stirring mixture was added EDC (218 mg, 1.14 mmol) and DMAP (104 mg, 0.851 mmol). After 10 min, S-4 (158 mg, 1.34 mmol, dissolved in 1.6 mL DCM) was added. The reaction was covered and allowed to proceed at RT while stirring for 24 h. The reaction was quenched with saturated $NaHCO_3$ (15 mL) and NaCl brine (10 mL). The mixture was extracted with DCM (3×20 mL) and the combined organic layer was dried with $MgSO_4$, filtered through Whatman filter paper (25 μm pore), and concentrated under reduced pressure to give a clear oil. The crude product was purified by silica flash chromatography (30% EA:hexanes gradient) to give 24 as a clear oil; yield 54%; TLC: Rf 0.57 (30% EA:hexanes); $^1$H NMR (500 MHz, CDCl$_3$) δ 7.38-7.28 (m, 5H), 5.29-5.21 (m, 2H), 5.18 (dd, J=3.5, 1.8 Hz, 1H), 5.11 (s, 2H), 5.06 (t, J=9.9 Hz, 1H), 4.87 (d, J=1.7 Hz, 1H), 4.03 (p, J=6.1 Hz, 1H), 3.93 (dq, J=9.7, 6.4 Hz, 1H), 2.65 (dd, J=15.5, 7.4 Hz, 1H), 2.58 (dd, J=15.5, 5.5 Hz, 1H), 2.46 (dd, J=15.5, 6.5 Hz, 1H), 2.38 (dd, J=15.6, 6.0 Hz, 1H), 2.12 (s, 3H), 2.04 (s, 3H), 1.95 (s, 3H), 1.66-1.49 (m, 4H), 1.35-1.22 (m, 20H), 1.21 (d, J=6.3 Hz, 3H), 0.93-0.83 (m, 6H). $^{13}$C NMR (126 MHz, CDCl$_3$) δ 170.40, 170.12, 169.95, 169.89, 169.84, 135.88, 128.52, 128.50, 128.38, 128.34, 128.21, 96.93, 75.33, 71.15, 70.95, 70.20, 69.17, 66.76, 66.37, 39.17, 38.99, 34.87, 33.87, 31.78, 31.74, 29.45, 29.25, 29.17, 29.12, 25.15, 25.15, 22.64, 22.61, 20.88, 20.78, 20.68, 17.31, 14.08, 14.08.

(R)-3-(((R)-3-[2,3,4-Tri-O-acetyl-α-L-rhamnopyranosyl]decanoyl)oxy)decanoic acid (25): A clean and dry RBF (two-necked, 50 mL, 14/20) and ground glass adapter (24/40 female to 14/20 male) were placed in a 350° C. furnace for 30 min. The glassware was removed, cooled, and assembled such that the adapter was attached to the RBF's central neck and a 24/40 three-way valve was attached to adapter. To the valve's inlet was attached a balloon filled with Ar gas and the glass assembly was purged by breaching the rubber septum capping the RBF's second neck with a hypodermic needle. Each joint was sealed with Teflon tape and secured with a Keck clip. Under positive pressure of Ar, 21 (342 mg, 0.474 mmol), Pd/C (34.2 mg, 10% Pd), 5 mL of dry THF, and a Teflon stir bar were quickly added to the RBF through the second neck which was immediately re-capped with a rubber septum. The assembly was closed, the balloon was filled with H$_2$ gas, and the assembly was purged once with H$_2$ and then kept under 1 atm of H$_2$. The reaction was allowed to proceed 12-24 h at RT and was periodically monitored by removing small aliquots (via syringe) and performing TLC. The reaction was quenched by filtering through a 12 mm Celite pad under light vacuum (25 torr) and the pad was washed with DCM (3×15 mL) and EA (3×15 mL). The combined organic layer was dried with MgSO$_4$, filtered through Whatman filter paper (25 μm pore), and concentrated under reduced pressure to give a clear oil. The crude product was purified by silica flash chromatography (20% MeOH:DCM, 0.1% AcOH gradient) and after coevaporation with toluene (3×20 mL) and DCM (3×20 mL) 25 was obtained as a clear oil; yield 76%; TLC: Rf 0.70 (20% MeOH:DCM, 0.1% AcOH); $^1$H NMR (500 MHz, CDCl$_3$) δ 5.18 (ddd, J=14.7, 11.2, 4.8 Hz, 2H), 5.07 (dd, J=3.4, 1.8 Hz, 1H), 4.99 (t, J=9.9 Hz, 1H), 4.83 (d, J=1.8 Hz, 1H), 3.98 (p, J=6.1 Hz, 1H), 3.88 (dq, J=9.9, 6.3 Hz, 1H), 2.57-2.36 (m, 4H), 2.08 (s, 3H), 1.99 (s, 3H), 1.91 (s, 3H), 1.54 (dtd, J=29.9, 16.1, 14.3, 6.9 Hz, 4H), 1.27-1.18 (m, 20H), 1.14 (d, J=6.3 Hz, 3H), 0.82 (td, J=6.8, 4.2 Hz, 6H). $^{13}$C NMR (126 MHz, CDCl$_3$) δ 175.00, 170.41, 170.27, 170.10, 170.06, 97.23, 76.05, 71.16, 70.85, 70.31, 69.21, 66.74, 39.36, 38.68, 34.84, 33.85, 31.77, 31.74, 29.44, 29.26, 29.17, 29.08, 25.18, 25.12, 22.63, 22.61, 20.92, 20.77, 20.69, 17.27, 14.07, 14.07.

(R)-3-(((S)-3-[2,3,4-Tri-O-acetyl-α-L-rhamnopyranosyl]decanoyl)oxy)decanoic acid (26): A clean and dry RBF (two-necked, 50 mL, 14/20) and ground glass adapter (24/40 female to 14/20 male) were placed in a 350° C. furnace for 30 min. The glassware was removed, cooled, and assembled such that the adapter was attached to the RBF's central neck and a 24/40 three-way valve was attached to adapter. To the valve's inlet was attached a balloon filled with Ar gas and the glass assembly was purged by breaching the rubber septum capping the RBF's second neck with a hypodermic needle. Each joint was sealed with Teflon tape and secured with a Keck clip. Under positive pressure of Ar, 22 (152 mg, 0.211 mmol), Pd/C (25.6 mg, 10% Pd), 5 mL of dry THF, and a Teflon stir bar were quickly added to the RBF through the second neck which was immediately re-capped with a rubber septum. The assembly was closed, the balloon was filled with H$_2$ gas, and the assembly was purged once with H$_2$ and then kept under 1 atm of H$_2$. The reaction was allowed to proceed 12-24 h at RT and was periodically monitored by removing small aliquots (via syringe) and performing TLC. The reaction was quenched by filtering through a 12 mm Celite pad under light vacuum (25 torr) and the pad was washed with DCM (3×15 mL) and EA (3×15 mL). The combined organic layer was dried with MgSO$_4$, filtered through Whatman filter paper (25 μm pore), and concentrated under reduced pressure to give a clear oil. The crude product was purified by silica flash chromatography (20% MeOH:DCM, 0.1% AcOH gradient) and after coevaporation with toluene (3×20 mL) and DCM (3×20 mL) 26 was obtained as a clear oil; yield 88%; TLC: Rf 0.70 (20% MeOH:DCM, 0.1% AcOH); $^1$H NMR (500 MHz, CDCl$_3$) δ 5.25-5.19 (m, 2H), 5.17 (dd, J=3.5, 1.8 Hz, 1H), 5.05 (t, J=10.0 Hz, 1H), 4.85 (d, J=1.8 Hz, 1H), 4.09 (dt, J=11.0, 5.6 Hz, 1H), 3.97 (dq, J=9.7, 6.2 Hz, 1H), 2.69-2.56 (m, 3H), 2.48 (dd, J=15.7, 5.1 Hz, 1H), 2.15 (s, 3H), 2.04 (s, 3H), 1.98 (s, 3H), 1.70-1.49 (m, 4H), 1.28 (t, J=9.7 Hz, 20H), 1.20 (d, J=6.2 Hz, 3H), 0.92-0.83 (m, 6H). $^{13}$C NMR (126 MHz, CDCl$_3$) δ 175.65, 170.74, 170.42, 170.25, 170.20, 96.22, 74.92, 71.16, 70.67, 70.34, 69.25, 66.73, 40.01, 38.61, 33.83, 33.13, 31.76, 31.72, 29.47, 29.28, 29.09, 29.04, 25.10, 24.74, 22.55, 22.55, 20.84, 20.69, 20.63, 17.17, 13.98, 13.98.

(S)-3-(((R)-3-[2,3,4-Tri-O-acetyl-α-L-rhamnopyranosyl]decanoyl)oxy)decanoic acid (27): A clean and dry RBF (two-necked, 50 mL, 14/20) and ground glass adapter (24/40 female to 14/20 male) were placed in a 350° C. furnace for 30 min. The glassware was removed, cooled, and assembled such that the adapter was attached to the RBF's central neck and a 24/40 three-way valve was attached to adapter. To the valve's inlet was attached a balloon filled with Ar gas and the glass assembly was purged by breaching the rubber septum capping the RBF's second neck with a hypodermic needle. Each joint was sealed with Teflon tape and secured with a Keck clip. Under positive pressure of Ar, 23 (473 mg, 0.656 mmol), Pd/C (47.3 mg, 10% Pd), 5 mL of dry THF, and a Teflon stir bar were quickly added to the RBF through the second neck which was immediately re-capped with a rubber septum. The assembly was closed, the balloon was filled with H$_2$ gas, and the assembly was purged once with H$_2$ and then kept under 1 atm of H$_2$. The reaction was allowed to proceed 12-24 h at RT and was periodically monitored by removing small aliquots (via syringe) and performing TLC. The reaction was quenched by filtering through a 12 mm Celite pad under light vacuum (25 torr) and the pad was washed with DCM (3×15 mL) and EA (3×15 mL). The combined organic layer was dried with MgSO$_4$, filtered through Whatman filter paper (25 μm pore), and concentrated under reduced pressure to give a clear oil. The crude product was purified by silica flash chromatography (20% MeOH:DCM, 0.1% AcOH gradient) and after coevaporation with toluene (3×20 mL) and DCM (3×20 mL) 27 was obtained as a clear oil; yield 90%; TLC: Rf 0.70 (20% MeOH:DCM, 0.1% AcOH); $^1$H NMR (500 MHz, CDCl$_3$) δ 5.27-5.19 (m, 2H), 5.14 (dd, J=3.4, 1.8 Hz, 1H), 5.05 (t, J=10.0 Hz, 1H), 4.89 (d, J=1.8 Hz, 1H), 4.07-4.00

(m, 1H), 3.94 (dq, J=9.9, 6.2 Hz, 1H), 2.66-2.42 (m, 4H), 2.15 (s, 3H), 2.05 (d, J=2.0 Hz, 3H), 1.98 (s, 3H), 1.72-1.53 (m, 4H), 1.32-1.23 (m, 20H), 1.20 (d, J=6.3 Hz, 3H), 0.92-0.80 (m, 6H). $^{13}$C NMR (126 MHz, CDCl$_3$) δ 174.37, 170.42, 170.40, 170.16, 170.15, 97.25, 76.13, 71.21, 70.97, 70.40, 69.27, 66.79, 39.42, 38.74, 34.88, 33.93, 31.83, 31.79, 29.51, 29.33, 29.23, 29.15, 25.25, 25.18, 22.69, 22.66, 21.00, 20.84, 20.77, 17.33, 14.23, 14.13.

(S)-3-(((S)-3-[2,3,4-Tri-O-acetyl-α-L-rhamnopyranosyl] decanoyl)oxy)decanoic acid (28): A clean and dry RBF (two-necked, 50 mL, 14/20) and ground glass adapter (24/40 female to 14/20 male) were placed in a 350° C. furnace for 30 min. The glassware was removed, cooled, and assembled such that the adapter was attached to the RBF's central neck and a 24/40 three-way valve was attached to adapter. To the valve's inlet was attached a balloon filled with Ar gas and the glass assembly was purged by breaching the rubber septum capping the RBF's second neck with a hypodermic needle. Each joint was sealed with Teflon tape and secured with a Keck clip. Under positive pressure of Ar, 24 (222 mg, 0.308 mmol), Pd/C (46 mg, 10% Pd), 5 mL of dry THF, and a Teflon stir bar were quickly added to the RBF through the second neck which was immediately re-capped with a rubber septum. The assembly was closed, the balloon was filled with H$_2$ gas, and the assembly was purged once with H$_2$ and then kept under 1 atm of H$_2$. The reaction was allowed to proceed 12-24 h at RT and was periodically monitored by removing small aliquots (via syringe) and performing TLC. The reaction was quenched by filtering through a 12 mm Celite pad under light vacuum (25 torr) and the pad was washed with DCM (3×15 mL) and EA (3×15 mL). The combined organic layer was dried with MgSO$_4$, filtered through Whatman filter paper (25 μm pore), and concentrated under reduced pressure to give a clear oil. The crude product was purified by silica flash chromatography (20% MeOH:DCM, 0.1% AcOH gradient) and after coevaporation with toluene (3×20 mL) and DCM (3×20 mL) 28 was obtained as a clear oil; yield 82%; TLC: Rf 0.70 (20% MeOH:DCM, 0.1% AcOH); $^1$H NMR (500 MHz, CDCl$_3$) δ 5.38 (tt, J=7.4, 5.6 Hz, 1H), 5.22 (dd, J=3.4, 1.8 Hz, 1H), 5.19 (dd, J=10.0, 3.4 Hz, 1H), 5.05 (t, J=9.9 Hz, 1H), 4.91 (d, J=1.8 Hz, 1H), 4.12-4.05 (m, 1H), 3.94 (dq, J=9.8, 6.2 Hz, 1H), 2.63-2.40 (m, 4H), 2.14 (s, 3H), 2.05 (s, 3H), 1.99 (s, 3H), 1.70-1.50 (m, 4H), 1.33-1.24 (m, 20H), 1.20 (d, J=6.3 Hz, 3H), 0.91-0.83 (m, 6H). $^{13}$C NMR (126 MHz, CDCl$_3$) δ 172.41, 171.52, 171.20, 171.01, 170.26, 99.22, 77.91, 71.10, 70.97, 70.35, 70.18, 66.72, 39.66, 39.32, 35.28, 34.43, 31.80, 31.79, 29.62, 29.35, 29.19, 29.16, 25.22, 25.13, 22.67, 22.65, 21.06, 20.97, 20.83, 17.31, 14.22, 14.08.

(R)-3-(((R)-3-[α-L-rhamnopyranosyl]decanoyl)oxy)decanoic acid (3a): To 25 (229 mg, 0.363 mmol) in a 20 mL scintillation vial, HPLC grade MeOH (5 mL) was added and to the stirring mixture was added KCN (11.8 mg, 0.181 mmol). Prior to use, the KCN crystals were ground with a mortar and pestle and were subjected to high vacuum (0.1 torr) for 1 h. The mixture was allowed to stir at RT for 24 h and qualitative TLC showed that the reaction was incomplete. Another portion of KCN was added (23.6 mg. 0.363 mmol) and the reaction was allowed to proceed at RT for another 24 h. Upon completion, the reaction was filtered through a 12 mm Celite pad under light vacuum (25 torr) and the pad was washed with excess EA (6×15 mL). The combined organic layer was filtered through silica gel in a Whatman filter paper, and the gel was washed with additional EA. The combined organic layer was dried with MgSO$_4$, filtered through Whatman filter paper (25 μm pore), and concentrated under reduced pressure to give a 3a as an extremely viscous and sticky oil or glassy amorphous solid without further purification. 3a was lyophilized (17 mtorr, 24 h) before use in analytical measurements; yield 50%; TLC: Rf 0.52 (20% MeOH:DCM, 0.1% AcOH); $^1$H NMR (500 MHz, MeOD) δ 5.26 (dt, J=7.9, 5.7 Hz, 1H), 4.83 (d, J=1.7 Hz, 1H), 4.00 (t, J=6.1 Hz, 1H), 3.77 (dd, J=3.4, 1.7 Hz, 1H), 3.64 (dd, J=9.4, 6.2 Hz, 1H), 3.60 (dd, J=9.6, 3.4 Hz, 1H), 3.37 (t, J=9.5 Hz, 1H), 2.51-2.41 (m, 3H), 2.36 (dd, J=14.5, 5.4 Hz, 1H), 1.67-1.50 (m, 4H), 1.29 (q, J=7.3, 5.8 Hz, 20H), 1.24 (d, J=6.2 Hz, 3H), 0.91-0.85 (m, 6H). $^{13}$C NMR (126 MHz, MeOD) δ 178.92, 172.67, 101.80, 76.73, 74.66, 73.78, 72.45, 72.21, 70.23, 43.87, 41.13, 36.41, 35.45, 33.01, 32.97, 30.70, 30.61, 30.35, 30.33, 26.38, 26.34, 23.71, 23.69, 17.96, 14.49, 14.48.

(R)-3-(((S)-3-[α-L-rhamnopyranosyl]decanoyl)oxy)decanoic acid (3$^b$): To 26 (115 mg, 0.182 mmol) in a 20 mL scintillation vial, HPLC grade MeOH (5 mL) was added and to the stirring mixture was added KCN (5.9 mg, 0.091 mmol). Prior to use, the KCN crystals were ground with a mortar and pestle and were subjected to high vacuum (0.1 torr) for 1 h. The mixture was allowed to stir at RT for 24 h and qualitative TLC showed that the reaction was incomplete. Another portion of KCN was added (11.8 mg. 0.182 mmol) and the reaction was allowed to proceed at RT for another 24 h. Upon completion, the reaction was filtered through a 12 mm Celite pad under light vacuum (25 torr) and the pad was washed with excess EA (6×15 mL). The combined organic layer was filtered through silica gel in a Whatman filter paper, and the gel was washed with additional EA. The combined organic layer was dried with MgSO$_4$, filtered through Whatman filter paper (25 μm pore), and concentrated under reduced pressure to give a 3b as an extremely viscous and sticky oil or glassy amorphous solid without further purification. 3b was lyophilized (17 mtorr, 24 h) before use in analytical measurements; yield 58%; TLC: Rf 0.48 (20% MeOH:DCM, 0.1% AcOH); $^1$H NMR (500 MHz, MeOD) δ 5.24 (p, J=6.2 Hz, 1H), 4.80 (d, J=1.7 Hz, 1H), 4.02 (p, J=6.1 Hz, 1H), 3.77 (dd, J=3.4, 1.7 Hz, 1H), 3.71-3.66 (m, 1H), 3.63 (dd, J=9.7, 3.4 Hz, 1H), 3.35 (t, J=9.6 Hz, 1H), 2.61 (dd, J=15.2, 6.3 Hz, 1H), 2.53-2.42 (m, 2H), 2.36 (dd, J=14.4, 6.1 Hz, 1H), 1.68-1.53 (m, 4H), 1.38-1.27 (m, 20H), 1.25 (d, J=6.2 Hz, 3H), 0.93-0.79 (m, 6H). $^{13}$C NMR (126 MHz, MeOD) δ 178.82, 172.57, 101.07, 75.94, 74.51, 73.92, 72.60, 72.25, 70.23, 43.88, 41.65, 35.39, 34.70, 32.99, 32.99, 30.72, 30.64, 30.40, 30.36, 26.43, 26.15, 23.71, 23.71, 17.97, 14.47, 14.46.

(S)-3-(((R)-3-[α-L-rhamnopyranosyl]decanoyl)oxy)decanoic acid (3c): To 27 (426 mg, 0.675 mmol) in a 20 mL scintillation vial, HPLC grade MeOH (5 mL) was added and to the stirring mixture was added KCN (88 mg, 1.35 mmol). Prior to use, the KCN crystals were ground with a mortar and pestle and were subjected to high vacuum (0.1 torr) for 1 h. The mixture was allowed to stir at RT for 24 h and qualitative TLC showed that the reaction was complete. The volume of methanol was reduced by 90% by blowing pressurized air across the top of the solvent. To the concentrated mixture were added EA (4 mL) and silica gel (~1 g) and the mixture was sonicated to dissolve all compounds and was allowed to stir for 30 min. The mixture was filtered through a 5 mm silica pad in a sintered glass funnel under light vacuum (25 torr). The pad was washed with excess EA (8×10 mL) and sparing amounts of methanol. The combined organic layer was dried with MgSO$_4$, filtered through Whatman filter paper (25 μm pore), and concentrated under reduced pressure to give a 3c as an extremely viscous and sticky oil or glassy amorphous solid without further purification. 3c was lyophilized (17 mtorr, 24 h) before use in analytical measurements; yield 86%; TLC: Rf 0.47 (20% MeOH:DCM, 0.1% AcOH); $^1$H NMR (500 MHz, MeOD) δ 5.24 (p, J=6.1 Hz, 1H), 4.84 (d, J=1.6 Hz, 1H), 4.01 (p, J=6.1 Hz, 1H), 3.75 (dd, J=3.4, 1.7 Hz, 1H), 3.67-3.63 (m, 1H), 3.60 (dd, J=9.5, 3.4 Hz, 1H), 3.38 (t, J=9.5 Hz, 1H), 2.57-2.44 (m, 4H), 1.67-1.52 (m, 4H), 1.37-1.26 (m, 20H), 1.25 (d, J=6.2 Hz, 3H), 0.94-0.80 (m, 6H). $^{13}$C NMR (126 MHz, MeOD) δ 177.43, 172.53, 101.63, 76.46, 73.88, 73.86, 72.51, 72.31, 70.22, 42.51, 40.76, 36.31, 35.27, 33.03, 32.99, 30.70, 30.57, 30.37, 30.32, 26.35, 26.35, 23.73, 23.70, 17.95, 14.46, 14.44.

(S)-3-(((S)-3-[α-L-rhamnopyranosyl]decanoyl)oxy)decanoic acid (3d): To 27 (158 mg, 0.250 mmol) in a 20 mL scintillation vial, HPLC grade MeOH (5 mL) was added and to the stirring mixture was added KCN (16.3 mg, 0.250 mmol). Prior to use, the KCN crystals were ground with a mortar and pestle and were subjected to high vacuum (0.1 torr) for 1 h. The mixture was allowed to stir at RT for 24 h and qualitative TLC showed that the reaction was incomplete. Another portion of KCN was added (8.2 mg. 0.125 mmol) and the reaction was allowed to proceed at RT for another 24 h. Upon completion, the volume of methanol was reduced by 90% by blowing pressurized air across the top of the solvent. To the concentrated mixture were added EA (4 mL) and silica gel (~1 g) and the mixture was sonicated to dissolve all compounds and was allowed to stir for 30 min. The mixture was filtered through a 5 mm silica pad in a sintered glass funnel under light vacuum (25 torr). The pad was washed with excess EA (8×10 mL) and sparing amounts of methanol. The combined organic layer was dried with MgSO$_4$, filtered through Whatman filter paper (25 μm pore), and concentrated under reduced pressure to give a 3d as an extremely viscous and sticky oil or glassy amorphous solid without further purification. 3d was lyophilized (17 mtorr, 24 h) before use in analytical measurements; yield 83%; TLC: Rf 0.50 (20% MeOH:DCM, 0.1% AcOH); $^1$H NMR (500 MHz, MeOD) δ 5.27 (dq, J=7.7, 5.9 Hz, 1H), 4.81 (d, J=1.7 Hz, 1H), 4.03 (p, J=6.1 Hz, 1H), 3.76 (dd, J=3.4, 1.7 Hz, 1H), 3.66 (dt, J=9.5, 6.3 Hz, 1H), 3.60 (dd, J=9.5, 3.4 Hz, 1H), 3.37 (t, J=9.6 Hz, 1H), 2.56-2.41 (m, 4H), 1.67-1.53 (m, 4H), 1.37-1.26 (m, 20H), 1.24 (d, J=6.2 Hz, 3H), 0.93-0.86 (m, 6H). $^{13}$C NMR (126 MHz, MeOD) δ 176.90, 172.84, 101.21, 75.99, 73.72, 73.41, 72.39, 72.19, 70.22, 42.01, 40.66, 36.33, 35.27, 33.00, 32.93, 30.63, 30.48, 30.33, 30.32, 26.31, 26.31, 23.71, 23.68, 17.96, 14.47, 14.47.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter. All references cited herein are incorporated by reference in their entirety.

What is claimed is:

1. A stereoselective method for producing a protected carbohydrate-based surfactant of the formula:

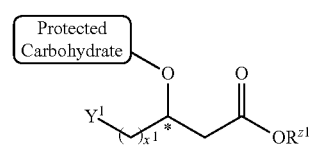

Formula I said method comprising: contacting an enantiomerically enriched alcohol compound of the formula:

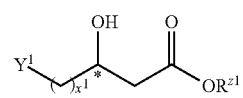

Formula A with a protected carbohydrate under conditions sufficient to form a covalent bond between said carbohydrate and said compound of Formula A to produce said protected carbohydrate-based surfactant of Formula I, wherein a carbohydrate of said protected carbohydrate is selected from the group consisting of a monosaccharide, a disaccharide, and a trisaccharide;

$Y^1$ is selected from the group consisting of hydrogen, ethylenyl, ethynyl, halide, —SH, —NH$_2$, and —CO$_2$R$^s$;

$R^{z1}$ is hydrogen, alkyl, benzyl, or a carboxylic acid protecting group;

$R^s$ is hydrogen or alkyl;

$x^1$ is an integer from 5 to 30; and

* is a chiral center.

2. The stereoselective method according to claim 1, wherein said enantiomerically enriched alcohol compound of Formula A is produced by an enzymatic kinetic resolution, wherein said enzymatic kinetic resolution comprises contacting a compound of the formula:

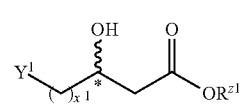

Formula A-1 with an esterase in the presence of an ester compound of the formula R$^a$O—C(=O)—R$^x$ under conditions sufficient to produce a mixture of an enantiomerically enriched alcohol compound of the formula:

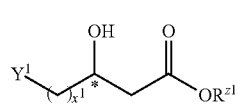

Formula A-2$^a$ and an enantiomerically enriched ester compound of the formula:

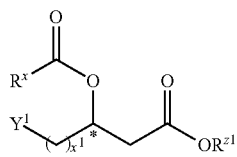
Formula A-2$^b$ wherein
R$^s$ is methyl,
R$^x$ is alkyl, typically methyl or ethyl, and
x$^1$, Y$^1$, and R$^{z1}$ are those defined in claim 1,
and wherein
  when compound of Formula A-2$^a$ has a same stereochemistry as compound of Formula A then separating said compound of Formula A-2$^a$ from said mixture to obtain said enantiomerically enriched alcohol compound of Formula A; and
  when said compound of Formula A-2$^b$ has a same stereochemistry as compound of Formula A, then:
    (i) separating compound of Formula A-2$^b$ from said mixture;
    (ii) producing said enantiomerically enriched alcohol compound of Formula A by hydrolyzing an ester group of said compound of Formula A-2$^b$.

3. The stereoselective method according to claim 2, wherein said enzymatic kinetic resolution produces at least 90% ee enriched compound of Formula A.

4. The stereoselective method according to claim 2, wherein said esterase comprises a triacylglycerol acyl hydrolase-EC 3.1.1.3 (lipase).

5. The stereoselective method according to claim 1 further comprising the steps of deprotecting said protected carbohydrate to produce a surfactant carbohydrate of the formula:

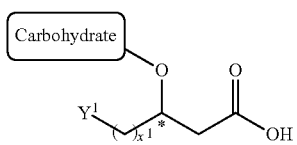
Formula I-A wherein Y$^1$, x$^1$, and * are those defined in claim 1.

6. The stereoselective method according to claim 1 further comprising the steps of:
  (i) when R$^{z1}$ of said compound of Formula I is alkyl, benzyl, or a carboxylic acid protecting group, then hydrolyzing R$^{z1}$ of said compound of Formula I under conditions sufficient to produce an enantiomerically enriched carboxylic acid compound of the formula:

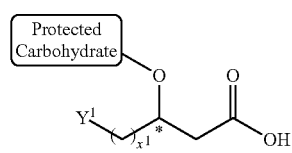
Formula I-B (ii) reacting said enantiomerically enriched carboxylic acid of Formula I-B with a lipid of the formula:

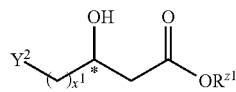
Formula B under conditions sufficient to produce a di-lipid carbohydrate of the formula:

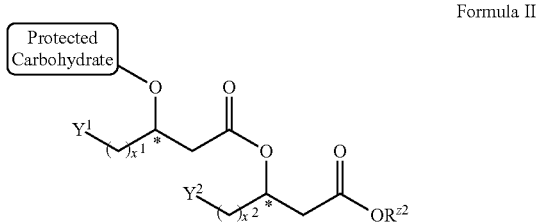
Formula II wherein
Y$^1$, x$^1$, and * are those defined in claim 1;
Y$^2$ is selected from the group consisting of hydrogen, ethylenyl, ethynyl, halide, —SH, —NH$_2$, and —CO$_2$R$^{s2}$;
R$^{z2}$ is hydrogen, alkyl, benzyl, or a carboxylic acid protecting group;
R$^{s2}$ is hydrogen or alkyl; and
x$^2$ is an integer from 5 to 30.

7. The stereoselective method according to claim 6 further comprising the steps of deprotecting said protected di-lipid carbohydrate of Formula II to produce an enantiomerically enriched surfactant di-lipid carbohydrate of the formula:

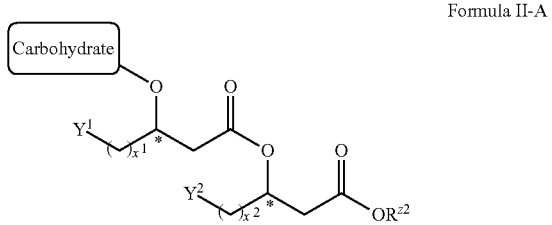
Formula II-A wherein
Y$^1$ is selected from the group consisting of hydrogen, ethylenyl, ethynyl, halide, —SH, —NH$_2$, and —CO$_2$H;
x$^1$ is an integer from 5 to 30;
* is a chiral center;
Y$^2$ is selected from the group consisting of hydrogen, ethylenyl, ethynyl, halide, —SH, —NH$_2$, and —CO$_2$H; and
x$^2$ is an integer from 5 to 30.

8. The stereoselective method according to claim 6, wherein said enantiomerically enriched alcohol compound of Formula B is produced by an enzymatic kinetic resolution, wherein said enzymatic kinetic resolution comprises contacting a compound of the formula:

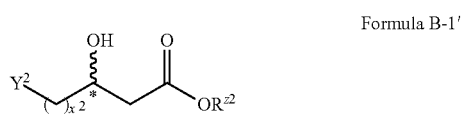
Formula B-1' with an esterase in the presence of an ester compound of the formula $R^a$—$O$—$C(=O)$—$R^x$ under conditions sufficient to produce a mixture of an enantiomerically enriched alcohol compound of the formula:

Formula B-2$^a$

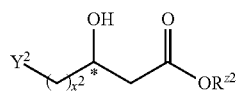

and an enantiomerically enriched ester compound of the formula:

Formula B-2$^b$

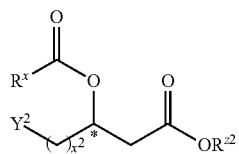

wherein $R^a$ is methyl, $R^x$ is alkyl, typically methyl or ethyl, and $x^2$, $Y^2$, and $R^{z2}$ are those defined in claim 6, and wherein when compound of Formula B-2$^a$ has a same stereochemistry as compound of Formula B then separating said compound of Formula B-2$^a$ from said mixture to obtain said enantiomerically enriched alcohol compound of Formula B; and when said compound of Formula B-2$^b$ has a same stereochemistry as compound of Formula B, then:

(i) separating compound of Formula B-2$^b$ from said mixture;

(ii) producing compound of Formula B by hydrolyzing an ester group of said compound of Formula B-2$^b$.

9. The stereoselective method according to claim 8, wherein said enzymatic kinetic resolution produces at least 90% ee of compound of Formula B.

\* \* \* \* \*

UNITED STATES PATENT AND TRADEMARK OFFICE
CERTIFICATE OF CORRECTION

| | |
|---|---|
| PATENT NO. | : 12,391,719 B2 |
| APPLICATION NO. | : 17/489477 |
| DATED | : August 19, 2025 |
| INVENTOR(S) | : Pemberton et al. |

Page 1 of 2

It is certified that error appears in the above-identified patent and that said Letters Patent is hereby corrected as shown below:

In the Claims

Column 46, Claim 1, Line 39:
"is a chiral center."

Should read:
-- * is a chiral center. --.

Column 48, Claim 6, Lines 1-9:

Should read:

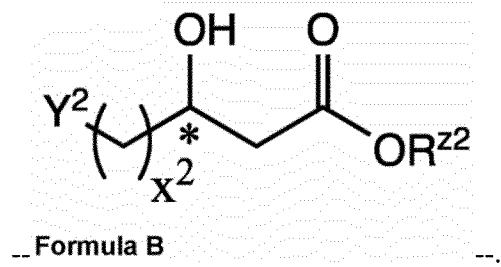

--.

Signed and Sealed this
Second Day of December, 2025

John A. Squires
*Director of the United States Patent and Trademark Office*

CERTIFICATE OF CORRECTION (continued)
U.S. Pat. No. 12,391,719 B2

Column 48, Claim 7, Lines 36-45:

" 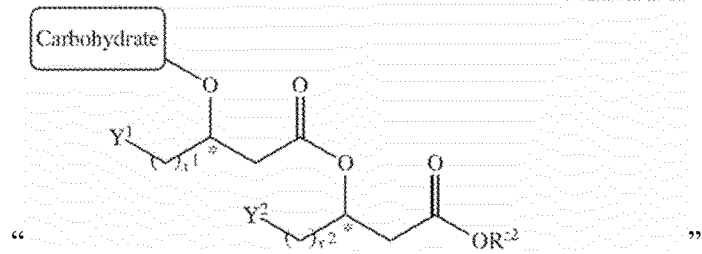 "

Should read:

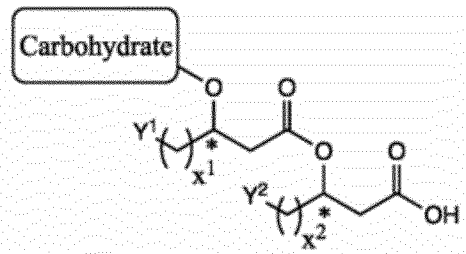

-- Formula II-A --.